(12) United States Patent
Heinrich et al.

(10) Patent No.: US 7,615,676 B2
(45) Date of Patent: Nov. 10, 2009

(54) TRANSGENIC SCREEN AND METHOD FOR SCREENING MODULATORS OF BRAIN-DERIVED NEUROTROPHIC FACTOR (BDNF) PRODUCTION

(75) Inventors: Gerhard Heinrich, Pleasant Hill, CA (US); Gigi Huynh, Vallejo, CA (US)

(73) Assignee: U.S. Department of Veterans Affairs, Washington, DC (US)

( * ) Notice: Subject to any disclaimer, the term of this patent is extended or adjusted under 35 U.S.C. 154(b) by 367 days.

(21) Appl. No.: 10/742,828

(22) Filed: Dec. 23, 2003

(65) Prior Publication Data

US 2004/0157294 A1 Aug. 12, 2004

Related U.S. Application Data

(63) Continuation-in-part of application No. 10/306,737, filed on Nov. 29, 2002, now Pat. No. 7,491,810.

(60) Provisional application No. 60/334,079, filed on Nov. 30, 2001.

(51) Int. Cl.
*C07H 21/04* (2006.01)
*C12N 5/00* (2006.01)
*C12N 5/02* (2006.01)

(52) U.S. Cl. .................. 800/3; 536/23.4; 536/24.1; 435/325

(58) Field of Classification Search .................. 800/8, 800/25; 435/325; 514/311, 312
See application file for complete search history.

(56) References Cited

U.S. PATENT DOCUMENTS

| 5,869,250 | A  | 2/1999  | Cheng et al.   |
| 6,380,458 | B1 | 4/2002  | Lin            |
| 6,465,715 | B1 | 10/2002 | Zwaal et al.   |
| 6,632,671 | B2 | 10/2003 | Unger          |
| 6,673,600 | B2 | 1/2004  | Peraus et al.  |
| 6,689,936 | B1 | 2/2004  | Burgeson et al.|

FOREIGN PATENT DOCUMENTS

| EP | 1050309 A1   | 11/2000 |
| JP | 5317049      | 3/1993  |
| JP | 725777       | 1/1995  |
| WO | WO 91/03568  | 3/1991  |
| WO | WO 99/38534  | 8/1999  |
| WO | WO 9964586 A2| 12/1999 |

OTHER PUBLICATIONS

Huynh et al, Int J Neuroscience, 19: 663-673, 2001.*
Timmusk et al, Neurn, 10: 475-489, 1993.*
Williams et al, J Appl Physiol, 88: 119-1126, 2000.*
Deiters et al, Zebrafish, 3(4): 415-429, 2006.*

Alderson, R.F., Alterman, A.L., Barde, Y.A. and Lindsay, R.M., (1990) Brain-derived neurotrophic factor increases survival and differentiated functions of rat septal cholinergic neurons in culture. Neuron, 5: 297-306.

Amgen-Regeneron Partners. (2001) Intrathecal and Subcutaneous BDNF not shown effective in ALS. MDA Research. Web site: http://www.mdausa.org/research/ct-alsbdnfit.html. (Jan. 11, 2002.).

Balbes, L.M., M. Cline, and D.D. Beusen. (2001) From target to drug in the virtual discovery lab. Drug Discovery and Development. Apr. 2001.

Biffo, S., Dechant, G., Okazawa, H. and Barde, Y.A., (1994) Molecular control of neuronal survival in the chick embryo. EXS, 71:39-48.

Binder, D.K., S. D. Croll, C. M. Gall, and H. E. Scharfman. (2001) BDNF and epilepsy: too much of a good thing? Trends in Neurosciences, 24(1):47-53.

Bishop, J.F., Joshi, G., Mueller, G.P. and Mouradian, M.M., (1997) Localization of putative calcium-responsive regions in the rat BDNF gene. Brain Res Mol Brain Res 50 IP, 1-2:154-164.

Bishop, J.F., Mueller, G.P. and Mouradian, M.M., (1994) Alternate 5' exons in the rat brain-derived neurotrophic factor gene: differential patterns of expression across brain regions. Brain Res Mol Brain Res 26 IP, 1-2:225-232.

Cockett, M., N. Dracopoli, and E. Sigal. (2000) Applied genomics: integration of the technology within pharmaceutical research and development. Current Opinion in Biotechnology, 11:602-609.

Cohen, N., Abramov, S., Dror, Y., and Freeman, A. (2001) In vitro enzyme evolution: the screening challenge of isolating the one in a million. Trends in Biotechnology, 19(12):507-510.

Davies, A.M., Thoenen, H. and Barde, Y.A., (1986) The response of chick sensory neurons to brain-derived neurotrophic factor. J Neurosci, 6:1897-904.

Department of Neurology, Baylor College of Medicine. (2001) Brain-Derived Neurotrophic Factor (BDNF). Web site: http://www.bcm.tmc.edu/neurol/struct/als/als8c.html. (Jan. 11, 2002.).

Dodd, A., P.M.Curtis, L.C Williams, and D.R Love. (2000) Zebrafish: bridging the gap between development and disease. Human Molecular Genetics. 9(16):Review, 2443-2449.

Finkbeiner, S., (2000) Calcium regulation of the brain-derived neurotrophic factor gene. Cell Mol Life Sci 57 IP, 3:394-401.

Fox, S.J., M.A. Yund, and S. Farr-Jones. (2000) Assay innovations vital to improving HTS. Drug Discovery and Development. Mar. 2000.

(Continued)

*Primary Examiner*—Anne-Marie Falk
*Assistant Examiner*—Magdalene K. Sgagias
(74) *Attorney, Agent, or Firm*—Dinesh Agarwal, P.C.

(57) ABSTRACT

A transgenic screen and method for screening biological and chemical test substances or molecules for their ability to influence or modulate the production of BDNF in cells, includes a fusion gene having a zebrafish BDNF gene fragment (promoter) and a fluorescent marker gene inserted downstream of the BDNF gene fragment. When the fusion gene is injected into a zebrafish embryo, the BDNF promoter causes the production of fluorescent protein in various cell types. The embryo is exposed to a test substance for determining the effect thereof on the production of the fluorescent marker protein.

5 Claims, 29 Drawing Sheets

OTHER PUBLICATIONS

Frade, J.M., Bovolenta, P., Martinez-Morales, J.R., Arribas, A., Barbas, J.A. and Rodriguez-Tebar, A., (1997) Control of early cell death by BDNF in the chick retina. Development, 124:3313-20.

Gotz, R., Koster, R., Winkler, C., Raulf, F., Lottspeich, F., Schartl, M. and Thoenen, H., (1994) Neurotrophin-6 is a new member of the nerve growth factor family. Nature, 372:266-9.

Guillemot, F., Auffray, C. and Devignes, M.D., (1999) Detailed transcript map of a 810-kb region at 11p14 involving identification of 10 novel human 3' exons. Eur J Hum Genet 7 IP, 4:487-495.

Harvey, K.J., Lukovic, D. and Ucker, D.S., (2001) Membrane-targeted green fluorescent protein reliably and uniquely marks cells through apoptotic death. Cytometry, 43:273-8.

Hashimoto, M. and Heinrich, G., (1997) Brain-derived neurotrophic factor gene expression in the developing zebrafish. Int J Dev Neurosci, 15:983-97.

Haupts, U., M. Rudiger. and A.J. Pope. (2000) Macroscopic versus microscopic fluorescence techniques in (ultra)-high throughput screening. Drug Discovery Today: HTS Supplement, 1 (1). Jun. 2000.

Hayes, V.Y., Towner, M.D. and Isackson, P.J., (1997) Organization, sequence and functional analysis of a mouse BDNF promoter. Brain Res Mol Brain Res 45 IP, 2:189-198.

Herzog, K.H., Bailey, K. and Barde, Y.A., (1994) Expression of the BDNF gene in the developing visual system of the chick. Development, 120:1643-9.

Hyman, C., Hofer, M., Barde, Y.A., Juhasz, M., Yancopoulos, G.D., Squinto, S.P. and Lindsay, R.M., (1991) BDNF is a neurotrophic factor for dopaminergic neurons of the substantia nigra. Nature, 350:230-2.

Huynh, G. and G. Heinrich. (2001) Brain-derived neurotrophic factor gene organization and transcription in the zebrafish embryo. International Journal of Developmental Neuroscience,19:663-673.

Inoue, A., Takahashi, M., Hatta, K., Hotta, Y. and Okamoto, H., (1994) Developmental regulation of islet-1 mRNA expression during neuronal differentiation in embryonic zebrafish. Dev Dyn, 199:1-11.

Ip, N. Y., Ibanez, C.F., Nye, S.H., McClain, J., Jones, P.F., Gies, D.R., Belluscio, L., Le Beau, M.M., Espinosa R, 3.r., Squinto, S.P. and et, a.l., (1992) Mammalian neurotrophin-4: structure, chromosomal localization, tissue distribution, and receptor specificity. Proc Natl Acad Sci U S A, 89:3060-4.

Johnson, J.E., Barde, Y.A., Schwab, M. and Thoenen, H., (1986) Brain-derived neurotrophic factor supports the survival of cultured rat retinal ganglion cells. J Neurosci, 6:3031-8.

Levi-Montalcini, R., Dal Toso, R., della Valle, F., Skaper, S.D. and Leon, A., (1995) Update of the NGF saga. J Neurol Sci, 130:119-27.

Levi-Montalcini, R., (1998) The saga of the nerve growth factor. Neuroreport, 9:R71-83.

Lum, T., G. Huynh, and G. Heinrich. (2001) Brain-derived neurotrophic factor and TrkB tyrosine kinase receptor gene expression in zebrafish embryo and larva. International Journal of Developmental Neuroscience, 19:569-587.

Maisonpierre, P.C., Belluscio, L., Squinto, S., Ip, N.Y., Furth, M.E., Lindsay, R.M. and Yancopoulos, G.D., (1990) Neurotrophin-3: a neurotrophic factor related to NGF and BDNF. Science, 247:1446-51.

Maisonpierre, P.C., Le Beau, M.M., Espinosa R, 3.r., Ip, N.Y., Belluscio, L., de la, M.o.S., Squinto, S., Furth, M.E. and Yancopoulos, G.D., (1991) Human and rat brain-derived neurotrophic factor and neurotrophin-3: gene structures, distributions, and chromosomal localizations. Genomics, 10:558-68.

Marmigere, F., Rage, F., Tapia-Arancibia, L. and Arancibia, S., (1998) Expression of mRNAs encoding BDNF and its receptor in adult rat hypothalamus. Neuroreport 9 IP, 6:1159-1163.

Martin, S.C., Sandell, J.H. and Heinrich, G., (1998) Zebrafish TrkC1 and TrkC2 receptors define two different cell populations in the nervous system during the period of axonogenesis. Dev Biol, 195:114-30.

Metsis, M., Timmusk, T., Arenas, E. and Persson, H., (1993) Differential usage of multiple brain-derived neurotrophic factor promoters in the rat brain following neuronal activation. Proc Natl Acad Sci U S A 90 IP, 19:8802-8806.

Nanda, S. and Mack, K.J., (1998) Multiple promoters direct stimulus and temporal specific expression of brain-derived neurotrophic factor in the somatosensory cortex. Brain Res Mol Brain Res 62 IP, 2:216-219.

Nature America Inc. (2000) Targeting zebrafish. nature genetics, 26(2):129-130.

Nasevicius, A., and Ekker, S. (2000) Effective targeted gene 'knockdown' in zebrafish. nature genetics, 26:216-220.

Nilsson, A.S., Fainzilber, M., Falck, P. and Ibanez, C.F., (1998) Neurotrophin-7: a novel member of the neurotrophin family from the zebrafish. FEBS Lett, 424:285-90.

Pickering, L. (2001) Developing Drugs to Counter Disease. Medical Chemistry, 44-47.

Reiss, T. (2001) Drug discovery of the future: the implications of the human genome project. Trends in Biotechnology, 19(12):496-499.

Rodriguez-Tebar, A. and Barde, Y.A., (1988) Binding characteristics of brain-derived neurotrophic factor to its receptors on neurons from the chick embryo. J Neurosci, 8:3337-42.

Rodriguez-Tebar, A., Jeffrey, P.L., Thoenen, H. and Barde, Y.A., (1989) The survival of chick retinal ganglion cells in response to brain-derived neurotrophic factor depends on their embryonic age. Dev Biol, 136:296-303.

Russo-Neustadt A, T. Ha, R. Ramirez , and J.P. Kesslak. (2001) Physical activityantidepressant treatment combination: impact on brain-derived neurotrophic factor and behavior in an animal model. Behaviour Brain Research, 120(1):87-95. BLTC Research. Web site: http://biopsychiatry.com/bdnf.htm. (Jan. 11, 2002.) (Abstract—2 pages).

Sano, K., Nanba, H., Tabuchi, A., Tsuchiya, T. and Tsuda, M., (1996) BDNF gene can Be activated by Ca2+ signals without involvement of de novo AP-1 synthesis. Biochem Biophys Res Commun 229 IP, 3:788-793.

Sendtner, M., Holtmann, B., Kolbeck, R., Thoenen, H. and Barde, Y.A., (1992) Brain-derived neurotrophic factor prevents the death of motoneurons in newborn rats after nerve section. Nature, 360:757-9.

Shieh, P.B. and Ghosh, A., (1999) Molecular mechanisms underlying activity-dependent regulation of BDNF expression. J Neurobiol 41 IP, 1:127-134.

Shieh, P.B., Hu, S.C., Bobb, K., Timmusk, T. and Ghosh, A., (1998) Identification of a signaling pathway involved in calcium regulation of BDNF expression. Neuron, 20:727-40.

Shintani, A., Ono, Y., Kaisho, Y. and Igarashi, K., (1992) Characterization of the 5'-flanking region of the human brain-derived neurotrophic factor gene. Biochem Biophys Res Commun 182 IP, 1:325-332.

Stainier, D. (2001) Zebrafish Genetics and Vertebrate Heart Formation. Nature Reviews, 2:39-48.

Tao, X., Finkbeiner, S., Arnold, D.B., Shaywitz, A.J. and Greenberg, M.E., (1998) Ca2+ influx regulates BDNF transcription by a CREB family transcription factor-dependent mechanism. Neuron 20 IP, 4:709-726.

Timmusk, T., Belluardo, N., Persson, H. and Metsis, M., (1994a) Developmental regulation of brain-derived neurotrophic factor messenger RNAs transcribed from different promoters in the rat brain. Neuroscience 60 IP, 2:287-291.

Timmusk, T., Lendahl, U., Funakoshi, H., Arenas, E., Persson, H. and Metsis, M., (1995) Identification of brain-derived neurotrophic factor promoter regions mediating tissue-specific, axotomy-, and neuronal activity-induced expression in transgenic mice. J Cell Biol, 128:185-99.

Timmusk, T., Palm, K., Metsis, M., Reintam, T., Paalme, V., Saarma, M. and Persson, H., (1993) Multiple promoters direct tissue-specific expression of the rat BDNF gene. Neuron 10 IP, 3:475-489.

Timmusk, T., Persson, H. and Metsis, M., (1994b) Analysis of transcriptional initiation and translatability of brain-derived neurotrophic factor mRNAs in the rat brain. Neurosci Lett 177 IP, 1-2:27-31.

Vente, A., Korn, B., Zehetner, G., Poustka, A. and Lehrach, H., (1999) Distribution and early development of microarray technology in Europe. Nat Genet , 22:22.

Wixon, J. (2000) Danio rerio, the zebrafish. Yeast, 17:225-231. Web site: http://www.zolodex.com/tests/. (Sep. 19, 2001.).

Zehetner, G. and Lehrach, H., (1994) The Reference Library System—sharing biological material and experimental data. Nature, 367:489-491.

Schug, J., Overton, G.C., (1997) 'TESS: Transcription Element Search Software on the WWW', Technical Report CBIL-TR-1997-1001-v0.0, of the Computational Biology and Informatics Laboratory, School of Medicine, University of Pennsylvania, URL: http://www.cbil.upenn.edu/tess/index.html.

Heinrich, G. and Huynh, G. (Nov. 6, 2000) Genetic Analysis of Progressive Restriction of BDNF Gene Expression During Zebrafish Embryo Development. Annual Meeting of the Society for Neuroscience, New Orleans, Louisiana (Poster Presentation) 4 pages.

Huynh, G. and Heinrich, G. (Jul. 22-23, 2001) Regulation of Zebrafish BDNF Gene Expression Involves Both 5' and 3' Flanks. The 1st Bi-Annual West-Coast Regional Zebrafish Meeting, University of Washington, Seattle, Washington (18 pages).

Miles, C.G., Rankin, L, Smith, S.I., Niksic, M., Elgar, G., and Hastie, N.D. (2003) Faithful expression of a tagged Fugu WT1 protein from a genomic transgene in zebrafish: efficient splicing of pufferfish genes in zebrafish but not mice. Nucleic Acids Research; 31(11): 2795-2802.

Stuart, G.W., Vielkind, J.R., McMurray, J.V., and Westerfield, M. (1990) Stable lines of transgenic zebrafish exhibit reproducible patterns of transgene expression. Development, 109(3): 577-584.

Heinrich, G., (2003) A novel BDNF gene promoter directs expression to skeletal muscle, BMC Neuroscience 2003, 4:11, 1-14.

Heinrich, G., and Pagtakhan C.J. (2004) Both 5' and 3' flanks regulate Zebrafish brain-derived neurotrophic factor gene expression, BMC Neuroscience 2004, 5:19, 20 pages (http://www.biomedcentral.com/1471-2202/5/19).

Zhong TP, Kaphingst K, Akella U, Haldi M, Lander ES, Fishman MC. 1998. Zebrafish Genomic Library in Yeast Artificial Chromosomes. Genomics. Feb. 15;48(1):136-8.

Amemiya CT, Zon LI, 1999. Generation of a zebrafish P1 artificial chromosome library. Genomics. Jun. 1;58(2):211-3.

Cormack BP, Valdivia RH, Falkow S. FACS-optimized mutants of the green fluorescent protein (GFP). Gene. 1996;173(1 Spec No.):33-8.

Schaefer, BC. Revolutions in Rapid Amplification of cDNA Ends: New Strategies for Polymerase Chain Reaction Cloning of Full-Length cDNA Ends. Analytical Biochemistry 227, 255-273 (1995).

Office Action dated Aug. 31, 2005, in U.S. Appl. No. 10/306,737, filed Nov. 29, 2002.

Office Action dated Mar. 14, 2006, in U.S. Appl. No. 10/306,737, filed Nov. 29, 2002.

Office Action dated Dec. 1, 2006, in U.S. Appl. No. 10/306,737, filed Nov. 29, 2002.

Office Action dated Aug. 24, 2007, in U.S. Appl. No. 10/306,737, filed Nov. 29, 2002.

Office Action dated Jun. 11, 2008, in U.S. Appl. No. 10/306,737. filed Nov. 29, 2002.

Notice of Allowance dated Nov. 3, 2008, in U.S. Appl. No. 10/306,737, filed Nov. 29, 2002.

Office Communication dated Nov. 10, 2008, in U.S. Appl. No. 10/306,737, filed Nov. 29, 2002.

* cited by examiner

Zebrafish BDNF Genomic Subclones

```
                                    Isl-1
00001    ATGGGATCCATGTTGTTTTTGTGCTCCTAATGAGAAGCAGAGTGATTTAT
                    <----- CCWTNTTNNNW  YY1
                            -----> TGTTGT  GR

PTF-1 beta              Isl-1              MEP-1
00051    TTATGGGATTACCTAGCTGGAACAGCCCTAATGCACAGTGTGAGAGTGTG Zeste           HNF-1
00101    CATGAGTGTATGTGTGTGTGTGCGCGCGCCTGTGTGTGTGTTTTACCT AP-1       Zeste
00151    CTCTTGGAGTCATGTCGCTCAGTAATTGCTGATGCAACTCTTTGTCATCC AP-3                    PTF-1 beta
00201    AGGGTTTGCCCTCTCCTCCTGTGAACCTATGGGATGAGTTATATTCATCT
                                        ----->TGAGTTA  AP-1
            GR        PU.1
00251    TGGCTTGTCCCTATAGGAGAGAGGAAGGGGACTGTAAGTGCGAGTATGTC Zeste  PRDI-BF1
00301    AAAATGAGTGAAGGTGAAAGTATATTTGTATAATTTTATATTTGAAAGTG

IRF-1
00351    TTCATGTGTAGCAGTGCAAAAAGGTTGAAGATGAGGTGACAAAGAAACAG

GATA-1              PU.1              HNF-1
00401    AAAGGTGGAGATGGAAATAAGTAAAGAAAGAGGAAGTTTGTGTGTGTATG
         <----- TGTGCC  GR
                                                        p300
00451    TGTGCCAAGTGTGTGTATGTGTGTGTGAGAAGGCAAGGTGTTAGCATCCA

PR                Sp1                    EF-2
00501    CTCCCATGCTGGGAACAGCTAGGTTTGAAACCGCTCCACCTCATTACCTT
            -----> TCCCAT  PTF-1 beta
                                            Pit-1A
00551    ATGCAGGGAATAATCATCATCACTATACATAAAACTCATCAATATAAATC
                            <----- YTWWAaATAR  CTF-1

GATA -1
00601    TTGCACTGGACAAAATCCAAAAGCACTTGCAGCTTGGTGAAAGTATGGGG
                    <----- YGGMNNNNNgCCAA  CTF-1

Isl-1                   PR,GR
00651    CTAATGATGTGGTGAAGCATAGGGTGAAAGAACAAGGAATGCTTTCGCTA
                                        -----> AGGAATG  MCBF

PPARalpha                              c-Myc
00701    AACTTCTCCAGGAAGGTCACGTTAAATAAGAATTAAACAATAAAGCCGCA
00751    GTTGAAGAGCAACATTATATCACCTCTATGTTTTTAAACATGTTTGACCA
00801    TTTACAAAAATTAAACAAACCACTCCCAGTTATCAGAGGAATAGAACTGA
                    -----> ATTAAACAAg  C/EBPbeta GR,PR                       NF-1
00851    CACCGGAAGAACAATGAATAGTATTAAAATCAATGAACCAGCCAACATCT
                        -----> ATGAATA  Pit-1a GR                      Zeste              Pit-1a
00901    GGCACATAAGCTCCTTTGGCAGACGGGGGGCTCAAACCTGACAATAGTTT CR                  ELP
00951    AAAATATCACATACAGAGAAGACTAGGGAATAATAGGACCTTGATGTGGT
                    -----> ATCACA  GCR
```

FIG. 5A

```
                        SRY                 AP-1
01001  GGGAGCAAGGAGTGAGCTCTTTACTTTGAAGCTACCTTTGTGGAGTCACA
01051  ATTGCAAATATCAATTTCAGCAGATGATCTATAGTCTTGTCACAAAAAGG

HNF-1 Isl-1      Isl-1
01101  TGTTTCAGATTAACCTAATGGCTGTCCATTAGGATGCTGGTGCAGCATTT

Oct-1
01151  GTTCGCAGCTAAGACAGTGAATTTAAAGTGATTTAGATGGCAAATGTAAT
                           <----- AAGTGA IRF-1

IRF-1
01201  AACTTAAAACCATAATTTACAGTTTTACAGGCAAGTGAAATAACATATAA

NF-1/L
01251  ATTATAATTTTGCCAATTATACACAGCTGTAGCTACGTGAAACAAAACAG

GR/PR                        Oct-1
01301  GTGTTCACTAGAGCTAGGCTAATTTCTCATGTCTTTATACAAATAGTCAT
                   <----- KRGGCKRRK Sp-1
                        -----> ATTWNNNATK Oct-3

GR                  c-Ets-1
01351  GGAAAACAACACGAAACATCAAACCAAACGGATATATACATGAAACAGCA
            <----- ACAACA
                              <----- MRMMGGAWRY Elk-1

IRF-1       Hinf-3
01401  CAAGCATACGCATAAGCGTATGAGATTCACTTTGTATCAGCACACAAAGG
                            GC,PR ACAgAGGAAT ----->
                              c-Ets-2 AAGGAA ----->

01451  AATCGTATTTTATATATACCTTCATCAGTAATGACGAAGAATGTGAACAA

AP-1
01501  AAATGTCAAAAGCCCACACTAACTCAGTGGTCGTCAGGAGAAGCCTGCTC

Sp1      Pit-1A
01551  GAGAAAAGAATGCGATGATTTAAAAATCGATGGGCGTTTAAAATCACCCC
                     -----> YtATTTWWAR MEF-2
                           AP-3 <----- GGgGTTTAAA
                       SREBP-1 ATCACCCCAc <-----

MEF-2
01601  AAGCCTCTATATGTCCAGGAATTAAAATAGGTTTCTGTCATATGTTGCTC
                       <----- MATNNWAAT Oct-3
                       <----- TAAAAT Pit-1a

NF-1
01651  GGTAAACGCCATAATAACACACTTTCCGGTTATTCGTTAGGAATAAGCAT c-Jun/ AP-1     CREB
01701  CTGAGGCTTCACTTGGTTGGCGCTCGCGCTTGAGTCACATGTTGCAACGT
                                  -----> CACATG USF
                          C/EBPalpha -----> CAaGTTGCAAC
                                c-Jun <----- ACGTCA 01751  CACGGCAGTAGTTAGTTACTGTAGTCGCGAGGAATGAAGCCGTCATTTCA
                              -----> GAGGAA PU.1
                              -----> AGGAATG MCBF

01801  AGCTGGAGAGCTCTCTCAATGCGCACTACACTGCGAGCGCTCACCA...
```

FIG. 5B

```
   1  AGCGCCCAAT ACGCAAACCG CCTCTCCCCG CGCGTTGGCC GATTCATTAA
  51  TGCAGCTGGC ACGACAGGTT TCCCGACTGG AAAGCGGGCA GTGAGCGCAA
 101  CGCAATTAAT GTGAGTTAGC TCACTCATTA GGCACCCCAG GCTTTACACT
 151  TTATGCTTCC GGCTCGTATG TTGTGTGGAA TTGTGAGCGG ATAACAATTT
 201  CACACAGGAA ACAGCTATGA CCATGATTAC GCCAAGCTTG CATGCCTGCA
 251  GGTCGACTCT AGATTCTGAA TGGGATCCAT GTTGTTTTTG TGCTCCTAAT
 301  GAGAAGCAGA GTGATTTATT TATGGGATTA CCTAGCTGGA ACAGCCCTAA
 351  TGCACAGTGT GAGAGTGTGC ATGAGTGTAT GTGTGTGTGT GTGCGCGCGC
 401  CTGTGTGTGT GTTTTACCTC TCTTGGAGTC ATGTCGCTCA GTAATTGCTG
 451  ATGCAACTCT TTGTCATCCA GGGTTTGCCC TCTCCTCCTG TGAACCTATG
 501  GGATGAGTTA TATTCATCTT GGCTTGTCCC TATAGGAGAG AGGAAGGGGA
 551  CTGTAAGTGC GAGTATGTCA AAATGAGTGA AGGTGAAAGT ATATTTGTAT
 601  AATTTTATAT TTGAAAGTGT TCATGTGTAG CAGTGCAAAA AGGTTGAAGA
 651  TGAGGTGACA AGAAACAGA AAGGTGGAGA TGGAAATAAG TAAAGAAAGA
 701  GGAAGTTTGT GTGTGTATGT GTGCCAAGTG TGTGTATGTG TGTGTGANAA
 751  GGCAAGGTGT TANCATCCAC TCCCATGCTG GAACAGCTA GGTTTGAAAC
 801  CGCTCCACCT CATTACCTTA TGCAGGGAAT AATCATCATC ACTATACATA
 851  AAACTCATCA ATATAAATCT TGCACTGGAC AAAATCCAAA AGCACTTGCA
 901  GCTTGGTGAA AGTATGGGGC TAATGATGTG GTGAANCATA GGGTGAAAGA
 951  ACAAGGAATG CTTTCGCTAA ACTTCTCCAG GAAGGTCACG TTAAATAAGA
1001  ATTAAACAAT AAAGCCGCAG TTGAAGAGCA ACATTATATC ACCTCTATGT
1051  TTTTAAACAT GTTTGACCAT TTACAAAAAT TAAACAAACC ACTCCCAGTT
1101  ATCAGAGGAA TAGAACTGAC ACCGGAAGAA CAATGAATAG TATTAAAATC
1151  AATGAACCAG CCAACATCTG GCACATAAGC TCCTTTGGCA GACGGGGGGC
1201  TCAAACCTGA CAATAGTTTA AAATATCACA TACAGAGAAG ACTAGGGAAT
1251  AATAGGACCT TGATGTGGTG GGAGCAAGGA GTGAGCTCTT TACTTTGAAG
```

FIG. 7A

```
1301  CTACCTTTGT GGAGTCACAA TTGCAAATAT CAATTTCAGC AGATGATCTA
1351  TAGTCTTGNC ACAAAAAGGT GTTTCAGATT AACCTAATGG CTGTCCATTA
1401  GGATGCTGGT GCAGCATTTG TTCGCAGCTA AGACAGTGAA TTTAAAGTGA
1451  TTTAGATGGC AAATGTAATA ACTTAAAACC ATAATTTACA GTTTTACAGG
1501  CAAGTGAAAT AACATATAAA TTATAATTTT GCCAATTATA CACAGCTGTA
1551  GCTACGTGAA ACAAAACAGG TGTTCACTAG AGCTAGGCTA ATTTCTCATG
1601  TCTTTATACA AATAGTCATG GAAAACAACA CGAAACATCA AACCAAACGG
1651  ATATATACAT GAAACAGCAC AAGCATACGC ATAAGCGTAT GAGATTCACT
1701  TTGTATCAGC ACACAAGGA  ATCGTATTTT ATATATACCT TCATCAGTAA
1751  TGACGAAGAA TGTGAACAAA AATGTCAAAA GCCCACACTA ACTCAGTGGT
1801  CGTCAGGAGA AGCCTGCTCG AGAAAAGAAT GCGATGATTT AAAAATCGAT
1851  GGGCGTTTAA AATCACCCCA AGCCTCTATA TGTCCAGGAA TTAAAATAGG
1901  TTTCTGTCAT ATGTTGCTCG GTAAACGCCA TAATAACACA CTTTCCGGTT
1951  ATTCGTTAGG AATAAGCATC TGAGGCTTCA CTTGGTTGGC GCTCGCGCTT
2001  GAGTCACATG TTGCAACGTC ACGGCAGTAG TTAGTTACTG TAGTCGCGAG
2051  GAATGAAGCC GTCATTTCAA GCTGGAGAGC TCTCTCAATG CGCACTACAC
2101  TGCGAGCGCT CACCATGTCA TCCAACTGCT TCAACTCAAC TCCAAAGGGA
2151  TCCCCGGGTA CCGGTCGCCA CCATGGTGAG CAAGGGCGAG GAGCTGTTCA
2201  CCGGGGTGGT GCCCATCCTG GTCGAGCTGG ACGGCGACGT AAACGGCCAC
2251  AAGTTCAGCG TGTCCGGCGA GGGCGAGGGC GATGCCACCT ACGGCAAGCT
2301  GACCCTGAAG TTCATCTGCA CCACCGGCAA GCTGCCCGTG CCCTGGCCCA
2351  CCCTCGTGAC CACCCTGACC TACGGCGTGC AGTGCTTCAG CCGCTACCCC
2401  GACCACATGA AGCAGCACGA CTTCTTCAAG TCCGCCATGC CGAAGGCTA
2451  CGTCCAGGAG CGCACCATCT TCTTCAAGGA CGACGGCAAC TACAAGACCC
2501  GCGCCGAGGT GAAGTTCGAG GGCGACACCC TGGTGAACCG CATCGAGCTG
2551  AAGGGCATCG ACTTCAAGGA GGACGGCAAC ATCCTGGGGC ACAAGCTGGA
```

FIG. 7B

```
2601  GTACAACTAC AACAGCCACA ACGTCTATAT CATGGCCGAC AAGCAGAAGA
2651  ACGGCATCAA GGTGAACTTC AAGATCCGCC ACAACATCGA GGACGGCAGC
2701  GTGCAGCTCG CCGACCACTA CCAGCAGAAC ACCCCCATCG GCGACGGCCC
2751  CGTGCTGCTG CCCGACAACC ACTACCTGAG CACCCAGTCC GCCCTGAGCA
2801  AAGACCCCAA CGAGAAGCGC GATCACATGG TCCTGCTGGA GTTCGTGACC
2851  GCCGCCGGGA TCACTCTCGG CATGGACGAG CTGTACAAGT CCGGACTCAG
2901  ATCTAAGCTG AACCCTCCTG ATGAGAGTGG CCCCGGCTGC ATGAGCTGCA
2951  AGTGTGTGCT CTCCTGAGGA TCGATCCACC GGATCTAGAT AACTGATCAT
3001  AATCAGCCAT ACCACATTTG TAGAGGTTTT ACTTGCTTTA AAAAACCTCC
3051  CACACCTCCC CCTGAACCTG AAACATAAAA TGAATGCAAT TGTTGTTGTT
3101  AACTTGTTTA TTGCAGCTTA TAATGGTTAC AAATAAAGCA ATAGCATCAC
3151  AAATTTCACA AATAAAGCAT TTTTTCACT GCATTCTAGT TGTGGTTTGT
3201  CCAAACTCAT CAATGTATCT TAACGCGTAA ATTGTAAGCG TTAATATTTT
3251  GTTAAAATTC GCGTTAAATT TTTGTTAAAT CAGCTCATTT TTTAACCAAT
3301  AGGCCGAAAT CGGCAAAATC CCTTATAAAT CAAAGAATA GACCGAGATA
3351  GGGTTGAGTG TTGTTCCAGT TTGGAACAAG AGTCCACTAT TAAAGAACGT
3401  GGACTCCAAC GTCAAAGGGC GAAAAACCGT CTATCAGGGC GATGGCCCAC
3451  TACGTGAACC ATCACCCTAA TCAAGTTTTT TGGGGTCGAG GTGCCGTAAA
3501  GCACTAAATC GGAACCCTAA AGGGAGCCCC CGATTTAGAG CTTGACGGGG
3551  AAAGCCGGCG AACGTGGCGA GAAAGGAAGG GAAGAAAGCG AAAGGAGCGG
3601  GCGCTAGGGC GCTGGCAAGT GTAGCGGTCA CGCTGCGCGT AACCACCACA
3651  CCCGCCGCGC TTAATGCGCC GCTACAGGGC GCGTCAGGTG GCACTTTTCG
3701  GGGAAATGTG CGCGGAACCC CTATTTGTTT ATTTTTCTAA ATACATTCAA
3751  ATATGTATCC GCTCATGAGA CAATAACCCT GATAAATGCT TCAATAATAT
3801  TGAAAAAGGA AGAGTCCTGA GGCGGAAAGA ACCAGCTGTG AATGTGTGT
3851  CAGTTAGGGT GTGGAAAGTC CCCAGGCTCC CCAGCAGGCA GAAGTATGCA
```

FIG. 7C

```
3901  AAGCATGCAT CTCAATTAGT CAGCAACCAG GTGTGGAAAG TCCCCAGGCT
3951  CCCCAGCAGG CAGAAGTATG CAAAGCATGC ATCTCAATTA GTCAGCAACC
4001  ATAGTCCCGC CCCTAACTCC GCCCATCCCG CCCCTAACTC CGCCCAGTTC
4051  CGCCCATTCT CCGCCCCATG GCTGACTAAT TTTTTTTATT TATGCAGAGG
4101  CCGAGGCCGC CTCGGCCTCT GAGCTATTCC AGAAGTAGTG AGGAGGCTTT
4151  TTTGGAGGCC TACTAGTCGG CCGTACGGGC CCTTTCGTCT CGCGCGTTTC
4201  GGTGATGACG GTGAAAACCT CTGACACATG CAGCTCCCGG AGACGGTCAC
4251  AGCTTGTCTG TAAGCGGATG CCGGGAGCAG ACAAGCCCGT CAGGGCGCGT
4301  CAGCGGGTGT TGGCGGGTGT CGGGGCTGGC TTAACTATGC GGCATCAGAG
4351  CAGATTGTAC TGAGAGTGCA CCATATGCGG TGTGAAATAC CGCACAGATG
4401  CGTAAGGAGA AAATACCGCA TCAGGCGGCC TTAAGGGCCT CGTGATACGC
4451  CTATTTTTAT AGGTTAATGT CATGATAATA ATGGTTTCTT AGACGTCAGG
4501  TGGCACTTTT CGGGGAAATG TGCGCGGAAC CCCTATTTGT TTATTTTTCT
4551  AAATACATTC AAATATGTAT CCGCTCATGA GACAATAACC CTGATAAATG
4601  CTTCAATAAT ATTGAAAAAG GAAGAGTATG AGTATTCAAC ATTTCCGTGT
4651  CGCCCTTATT CCCTTTTTTG CGGCATTTTG CCTTCCTGTT TTTGCTCACC
4701  CAGAAACGCT GGTGAAAGTA AAAGATGCTG AAGATCAGTT GGGTGCACGA
4751  GTGGGTTACA TCGAACTGGA TCTCAACAGC GGTAAGATCC TTGAGAGTTT
4801  TCGCCCCGAA GAACGTTTTC CAATGATGAG CACTTTTAAA GTTCTGCTAT
4851  GTGGCGCGGT ATTATCCCGT ATTGACGCCG GGCAAGAGCA ACTCGGTCGC
4901  CGCATACACT ATTCTCAGAA TGACTTGGTT GAGTACTCAC CAGTCACAGA
4951  AAAGCATCTT ACGGATGGCA TGACAGTAAG AGAATTATGC AGTGCTGCCA
5001  TAACCATGAG TGATAACACT GCGGCCAACT TACTTCTGAC AACGATCGGA
5051  GGACCGAAGG AGCTAACCGC TTTTTTGCAC AACATGGGGG ATCATGTAAC
5101  TCGCCTTGAT CGTTGGGAAC CGGAGCTGAA TGAAGCCATA CCAAACGACG
5151  AGCGTGACAC CACGATGCCT GTAGCAATGG CAACAACGTT GCGCAAACTA
```

FIG. 7D

```
5201  TTAACTGGCG AACTACTTAC TCTAGCTTCC CGGCAACAAT TAATAGACTG
5251  GATGGAGGCG GATAAAGTTG CAGGACCACT TCTGCGCTCG GCCCTTCCGG
5301  CTGGCTGGTT TATTGCTGAT AAATCTGGAG CCGGTGAGCG TGGGTCTCGC
5351  GGTATCATTG CAGCACTGGG GCCAGATGGT AAGCCCTCCC GTATCGTAGT
5401  TATCTACACG ACGGGGAGTC AGGCAACTAT GGATGAACGA AATAGACAGA
5451  TCGCTGAGAT AGGTGCCTCA CTGATTAAGC ATTGGTAACT GTCAGACCAA
5501  GTTTACTCAT ATATACTTTA GATTGATTTA AAACTTCATT TTTAATTTAA
5551  AAGGATCTAG GTGAAGATCC TTTTTGATAA TCTCATGACC AAAATCCCTT
5601  AACGTGAGTT TTCGTTCCAC TGAGCGTCAG ACCCCGTAGA AAAGATCAAA
5651  GGATCTTCTT GAGATCCTTT TTTTCTGCGC GTAATCTGCT GCTTGCAAAC
5701  AAAAAAACCA CCGCTACCAG CGGTGGTTTG TTTGCCGGAT CAAGAGCTAC
5751  CAACTCTTTT TCCGAAGGTA ACTGGCTTCA GCAGAGCGCA GATACCAAAT
5801  ACTGTCCTTC TAGTGTAGCC GTAGTTAGGC CACCACTTCA AGAACTCTGT
5851  AGCACCGCCT ACATACCTCG CTCTGCTAAT CCTGTTACCA GTGGCTGCTG
5901  CCAGTGGCGA TAAGTCGTGT CTTACCGGGT TGGACTCAAG ACGATAGTTA
5951  CCGGATAAGG CGCAGCGGTC GGGCTGAACG GGGGGTTCGT GCACACAGCC
6001  CAGCTTGGAG CGAACGACCT ACACCGAACT GAGATACCTA CAGCGTGAGC
6051  TATGAGAAAG CGCCACGCTT CCCGAAGGGA GAAAGGCGGA CAGGTATCCG
6101  GTAAGCGGCA GGGTCGGAAC AGGAGAGCGC ACGAGGGAGC TTCCAGGGGG
6151  AAACGCCTGG TATCTTTATA GTCCTGTCGG GTTTCGCCAC CTCTGACTTG
6201  AGCGTCGATT TTTGTGATGC TCGTCAGGGG GGCGGAGCCT ATGGAAAAAC
6251  GCCAGCAACG CGGCCTTTTT ACGGTTCCTG GCCTTTGCT GGCCTTTTGC
6301  TCACATGTTC TTTCCTGCGT TATCCCCTGA TTCTGTGGAT AACCGTATTA
6351  CCGCCTTTGA GTGAGCTGAT ACCGCTCGCC GCAGCCGAAC GACCGAGCGC
6401  AGCGAGTCAG TGAGCGAGGA AGCGGAAG
```

FIG. 7E

```
   1  ATGGGATCCA TGTTGTTTTT GTGCTCCTAA TGAGAAGCAG AGTGATTTAT
  51  TTATGGGATT ACCTAGCTGG AACAGCCCTA ATGCACAGTG TGAGAGTGTG
 101  CATGAGTGTA TGTGTGTGTG TGTGCGCGCG CCTGTGTGTG TGTTTTACCT
 151  CTCTTGGAGT CATGTCGCTC AGTAATTGCT GATGCAACTC TTTGTCATCC
 201  AGGGTTTGCC CTCTCCTCCT GTGAACCTAT GGGATGAGTT ATATTCATCT
 251  TGGCTTGTCC CTATAGGAGA GAGGAAGGGG ACTGTAAGTG CGAGTATGTC
 301  AAAATGAGTG AAGGTGAAAG TATATTTGTA TAATTTTATA TTTGAAAGTG
 351  TTCATGTGTA GCAGTGCAAA AAGGTTGAAG ATGAGGTGAC AAAGAAACAG
 401  AAAGGTGGAG ATGGAAATAA GTAAAGAAAG AGGAAGTTTG TGTGTGTATG
 451  TGTGCCAAGT GTGTGTATGT GTGTGTGAGA AGGCAAGGTG TTAGCATCCA
 501  CTCCCATGCT GGGAACAGCT AGGTTTGAAA CCGCTCCACC TCATTACCTT
 551  ATGCAGGGAA TAATCATCAT CACTATACAT AAAACTCATC AATATAAATC
 601  TTGCACTGGA CAAAATCCAA AAGCACTTGC AGCTTGGTGA AGTATGGGG
 651  CTAATGATGT GGTGAAGCAT AGGGTGAAAG AACAAGGAAT GCTTTCGCTA
 701  AACTTCTCCA GGAAGGTCAC GTTAATAAG AATTAAACAA TAAAGCCGCA
 751  GTTGAAGAGC AACATTATAT CACCTCTATG TTTTTAAACA TGTTTGACCA
 801  TTTACAAAAA TTAAACAAAC CACTCCCAGT TATCAGAGGA ATAGAACTGA
 851  CACCGGAAGA ACAATGAATA GTATTAAAAT CAATGAACCA GCCAACATCT
 901  GGCACATAAG CTCCTTTGGC AGACGGGGGG CTCAAACCTG ACAATAGTTT
 951  AAAATATCAC ATACAGAGAA GACTAGGGAA TAATAGGACC TTGATGTGGT
1001  GGGAGCAAGG AGTGAGCTCT TTACTTTGAA GCTACCTTTG TGGAGTCACA
1051  ATTGCAAATA TCAATTTCAG CAGATGATCT ATAGTCTTGT CACAAAAAGG
1101  TGTTTCAGAT TAACCTAATG GCTGTCCATT AGGATGCTGG TGCAGCATTT
1151  GTTCGCAGCT AAGACAGTGA ATTTAAAGTG ATTTAGATGG CAAATGTAAT
1201  AACTTAAAAC CATAATTTAC AGTTTTACAG GCAAGTGAAA TAACATATAA
1251  ATTATAATTT TGCCAATTAT ACACAGCTGT AGCTACGTGA AACAAAACAG
```

FIG. 8A

```
1301  GTGTTCACTA GAGCTAGGCT AATTTCTCAT GTCTTTATAC AAATAGTCAT

1351  GGAAAACAAC ACGAAACATC AAACCAAACG GATATATACA TGAAACAGCA

1401  CAAGCATACG CATAAGCGTA TGAGATTCAC TTTGTATCAG CACACAAAGG

1451  AATCGTATTT TATATATACC TTCATCAGTA ATGACGAAGA ATGTGAACAA

1501  AAATGTCAAA AGCCCACACT AACTCAGTGG TCGTCAGGAG AAGCCTGCTC

1551  GAGAAAAGAA TGCGATGATT TAAAAATCGA TGGGCGTTTA AAATCACCCC

1601  AAGCCTCTAT ATGTCCAGGA ATTAAAATAG GTTTCTGTCA TATGTTGCTC

1651  GGTAAACGCC ATAATAACAC ACTTTCCGGT TATTCGTTAG GAATAAGCAT

1701  CTGAGGCTTC ACTTGGTTGG CGCTCGCGCT TGAGTCACAT GTTGCAACGT

1751  CACGGCAGTA GTTAGTTACT GTAGTCGCGA GGAATGAAGC CGTCATTTCA

1801  AGCTGGAGAG CTCTCTCAAT GCGCACTACA CTGCGAGCGC TCACCA
```

FIG. 8B

```
   1  GTCTGTGGTG GTGGTGGTGT CAACTTTGTG CTGTATGTGC AGTTCTGAAT
  51  GGGATCCATG TTGTTTTTGT GCTCCTAATG AGAAGCAGAG TGATTTATTT
 101  ATGGATTACC TAGCTGGAAC AGCCCTAATG CACAGTGTGA GAGTGTGCAT
 151  GAGTGTATGT GTGTGTGTAT GCGCGCGCCT GTGTGTGTGT TTTACCTCTC
 201  TTGGAGTCAT GTCGCTCAGT AATTGCTGAT GCAACTCTTT GTCATCCAGG
 251  GTTTGCCCTC TCCTCCTGTG AACCTATGGG ATGAGTTATA TTCATCTTGG
 301  CTTGTCCCTA TAGGAGAGAG GAAGGGGACT GTAAGTGCGA GTATGTCAAA
 351  ATGAGTGAAG GTGAAAGTAT ATTTGTATAA TTTTATATTT GAAAGTGTTC
 401  ATGTGTAGCA GTGCAAAAAG GTTGAAGATG AGGTGACAAA GAAACAGAAA
 451  GGTGGAGATG GAAATAAGTA AAGAAGAGG GAGTTTGTGT GTGTATGTGT
 501  GCGAGTGTGT GTAAGTGTGT GTGAGAAGGC AGGTGTTAGC ATCCACTCCC
 551  ATGCTGGGAA CAGCTAGGTT TGAAACCGCT CCACCTCATT ACCTTATGCA
 601  GGGAATAATC ATCATCACTA TACACAAAAC TCATCAATAT AAATCTTGCA
 651  CTGGACAAGA TCCAAAAGCA CTTGCAGCTT GGTGAAAGTA TGGGGCTAAT
 701  GATGTGGTGA AGCATAGGGT GAAAGAACAA GGAATGCTTT TGCTAAACTT
 751  CTCCAGGAAG GTCACGTTAA ATAAGAATTA ACAATAAAG CCACAGTTGA
 801  AGAGCAACAT TATATCACCT CTATGTTTTT AAACATGTTT GACCGTTTAC
 851  AAAAATCAAA CAAACCACTC CCAGTTATCA GAGGAATAGA ACTGACACCG
 901  GAAGAACAAT GAATAGTATT AAAATCAATG AACCAGCCAA CATCTGGCAC
 951  ATAAGCTCCT TTGGCAGACG GGGGGCTCAA ACCTGACAAT AGTTTAAAAT
1001  ATCACATACA GAGAAGACTA GGGAATAATA GGACCTTGAT GTGGTGGGAG
1051  CAAGGAGTGA GCTCTTTACT TTGAAGCTAC CTTTGTGGAG TCACAATTGC
1101  AAATATCAAT TTCAGCAGAT GATCTATAGT CTTGTCACAA AAGGTGTTT
1151  CAGATTAACC TAACGGCTGT CCATTAGGAT GCTGGTGCAG CATTTGTTCG
1201  CAGCTAAGAC AGTGAATTTA AAGTGATTTA GATGGCAAAT GTAATAACTT
1251  AAAACCATAA TTTACAGTTT TACAGGCAAG TGAAATAACA TATAAATTAT
```

FIG. 9A

1301 AATTTTGCCA ATTATACAAA GCTGTAGCTA CGTGAAGCAA AACAGGTGTT

1351 CACTAGAGCT AGGCTAATTT CTCATGTCTT TATACAAATA GTCAAGGAAA

1401 ACAACACGAA ACATCAAACC AAACGGATAT ATACATGAAA CAGCACAAGC

1451 ATACGCATAA GCGTATGAGA TTCACTTTGT ATCAGCACAC AAAGGAATCG

1501 TATTTTATAT ATACCTTCAT CAGTAATGAC GAAGAATGTG AACAAAAATG

1551 TCAAAAGCCC ACACTAACTC AGTGGTCGTC AGGAGAAGCC TGCTCGAGAA

1601 AAGAATGCGA TGATTTAAAA ATCGATGGGC GTTTAAAATC ACCCCAAGCC

1651 TCTATATGTC CAGGAATTAA AATAGGTTTC TGTCATATGT TGCTCGGTAA

1701 ACGCCATAAT AACACACTTT CCGGTTATTC GTTAGGAATA AGCATCTGAG

1751 CCTTCACTTG GTTGGCGCTC GCGCTTGAGT CACATGTTGC AACGTCACGG

1801 CAGTAGTTAG TTACTGTAGT CGCGAGGAAT GAAGCCGTC

FIG. 9B

```
   1  ACCACCGCGG  TGGCGGCCGC  TCCGGAGTGC  TCCTAATGAG  AAGCAGAGTG
  51  AAGAGTGATT  TATTTATGGA  TTACCTAGCT  GGAACAGCCC  TAATGCACAG
 101  TGTGAGAGTG  TGCATGAGTG  TATGTGTGTG  TGTATGCGCG  CGCCTGTGTG
 151  TGTGTTTTAC  CTCTCTTGGA  GTCATGTCGC  TCAGTAATTG  CTGATGCAAC
 201  TCTTTGTCAT  CCAGGGTTTG  CCCTCTCCTC  CTGTGAACCT  ATGGGATGAG
 251  TTATATTCAT  CTTGGCTTGT  CCCTATAGGA  GAGAGGAAGG  GGACTGTAAG
 301  TGCGAGTATG  TCAAAATGAG  TGAAGGTGAA  AGTATATTTG  TATAATTTTA
 351  TATTTGAAAG  TGTTCATGTG  TAGCAGTGCA  AAAAGGTTGA  AGATGAGGTG
 401  ACAAAGAAAC  AGAAGGTGG   AGATGGAAAT  AAGTAAAGAA  AGAGGGAGTT
 451  TGTGTGTGTA  TGTGTGCGAG  TGTGTGTAAG  TGTGTGTGAG  AAGGCAGGTG
 501  TTAGCATCCA  CTCCCATGCT  GGGAACAGCT  AGGTTTGAAA  CCGCTCCACC
 551  TCATTACCTT  ATGCAGGGAA  TAATCATCAT  CACTATACAC  AAAACTCATC
 601  AATATAAATC  TTGCACTGGA  CAAGATCCAA  AAGCACTTGC  AGCTTGGTGA
 651  AAGTATGGGG  CTAATGATGT  GGTGAAGCAT  AGGGTGAAAG  AACAAGGAAT
 701  GCTTTTGCTA  AACTTCTCCA  GGAAGGTCAC  GTTAAATAAG  AATTAAACAA
 751  TAAAGCCACA  GTTGAAGAGC  AACATTATAT  CACCTCTATG  TTTTTAAACA
 801  TGTTTGACCG  TTTACAAAAA  TCAAACAAAC  CACTCCCAGT  TATCAGAGGA
 851  ATAGAACTGA  CACCGGAAGA  ACAATGAATA  GTATTAAAAT  CAATGAACCA
 901  GCCAACATCT  GGCACATAAG  CTCCTTTGGC  AGACGGGGGG  CTCAAACCTG
 951  ACAATAGTTT  AAAATATCAC  ATACAGAGAA  GACTAGGGAA  TAATAGGACC
1001  TTGATGTGGT  GGGAGCAAGG  AGTGAGCTCT  TTACTTTGAA  GCTACCTTTG
1051  TGGAGTCACA  ATTGCAAATA  TCAATTTCAG  CAGATGATCT  ATAGTCTTGT
1101  CACAAAAAGG  TGTTTCAGAT  TAACCTAACG  GCTGTCCATT  AGGATGCTGG
1151  TGCAGCATTT  GTTCGCAGCT  AAGACAGTGA  ATTTAAAGTG  ATTTAGATGG
1201  CAAATGTAAT  AACTTAAAAC  CATAATTTAC  AGTTTTACAG  GCAAGTGAAA
1251  TAACATATAA  ATTATAATTT  TGCCAATTAT  ACAAAGCTGT  AGCTACGTGA
```

FIG. 10A

```
1301  AGCAAAACAG GTGTTCACTA GAGCTAGGCT AATTTCTCAT GTCTTTATAC
1351  AAATAGTCAA GGAAAACAAC ACGAAACATC AAACCAAACG GATATATACA
1401  TGAAACAGCA CAAGCATACG CATAAGCGTA TGAGATTCAC TTTGTATCAG
1451  CACACAAAGG AATCGTATTT TATATATACC TTCATCAGTA ATGACGAAGA
1501  ATGTGAACAA AAATGTCAAA AGCCCACACT AACTCAGTGG TCGTCAGGAG
1551  AAGCCTGCTC GAGAAAGAA TGCGATGATT TAAAAATCGA TGGGCGTTTA
1601  AAATCACCCC AAGCCTCTAT ATGTCCAGGA ATTAAAATAG GTTTCTGTCA
1651  TATGTTGCTC GGTAAACGCC ATAATAACAC ACTTTCCGGT TATTCGTTAG
1701  GAATAAGCAT CTGAGCCTTC ACTTGGTTGG CGCTCGCGCT TGAGTCACAT
1751  GTTGCAACGT CACGGCAGTA GTTAGTTACT GTAGTCGCGA GGAATGAAGC
1801  CGTCATTTCA AGCTGGAGAG CTCTCTCAAT GCGCACTACA CTGCGAGCGC
1851  TCACCATGTC ATCCAACTGC TTCAACTCAA CTCCAAAGGA TCCGCTCAGT
1901  CATGGGAGTC CATTACCTCA ACCATGCAAT TTCCACCATC AATAATTTAA
1951  TCTATTTGCT CAAAAGCTGA AGAGACAACT TGCAGCTGCT GCTTGGCGAA
2001  GAGCGGACGA ATATCGCAGA ATAGTTGCGC GGAGGTCTTA TCCAAAACAT
2051  CCCAGATGAC ACTGTCCTGC TGAATGGTCT CCTTTACGAC TGGACAGTAC
2101  CCGGGTACCG GTCGCCACCA TGGTGCGCTC CTCCAAGAAC GTCATCAAGG
2151  AGTTCATGCG CTTCAAGGTG CGCATGGAGG GCACCGTGAA CGGCCACGAG
2201  TTCGAGATCG AGGGCGAGGG CGAGGGCCGC CCCTACGAGG GCCACAACAC
2251  CGTGAAGCTG AAGGTGACCA AGGGCGGCCC CCTGCCCTTC GCCTGGGACA
2301  TCCTGTCCCC CCAGTTCCAG TACGGCTCCA AGGTGTACGT GAAGCACCCC
2351  GCCGACATCC CCGACTACAA GAAGCTGTCC TTCCCCGAGG GCTTCAAGTG
2401  GGAGCGCGTG ATGAACTTCG AGGACGGCGG CGTGGCGACC GTGACCCAGG
2451  ACTCCTCCCT GCAGGACGGC TGCTTCATCT ACAAGGTGAA GTTCATCGGC
2501  GTGAACTTCC CCTCCGACGG CCCCGTGATG CAGAAGAAGA CCATGGGCTG
2551  GGAGGCCTCC ACCGAGCGCC TGTACCCCCG CGACGGCGTG CTGAAGGGCG
```

FIG. 10B

```
2601  AGATCCACAA GGCCCTGAAG CTGAAGGACG GCGGCCACTA CCTGGTGGAG
2651  TTCAAGTCCA TCTACATGGC CAAGAAGCCC GTGCAGCTGC CCGGCTACTA
2701  CTACGTGGAC ACCAAGCTGG ACATCACCTC CCACAACGAG GACTACACCA
2751  TCGTGGAGCA GTACGAGCGC ACCGAGGGCC GCCACCACCT GTTCCTGTAG
2801  CGGCCGCGAC TCTAGAATTC GGCCGCATTG ACCATTAAGA GGGGCAGATA
2851  GTGTACACAA TGTATAGATT TTATTGAGAG TTCTAAAAAA AGAGAGAGAG
2901  AAAGAGAAAA TATCTATTTG TATATACATA ACAGGGTAAA TTATTCAGTC
2951  AGATAAAAAT TTTATGGACT GCATGTAAAA AAGAAAAAGT TTATACAGTA
3001  AGTGATACTA CAGTCTATTT ATTGAACATA TTCATGACCT TGTAAACAAT
3051  TAAAAAAGA TCTGATCAGT CATTTGCGCC CAGTTCAAAT TACTATATCA
3101  CATTCCTCAA GACATTGTGT TTTTTACGTT GCCAAGATTT TGAGAGATGA
3151  GGAGAGGAGG GGGTGAGGAA GAATTACATT CAAGAAAGAA AAAAAAGAA
3201  AAAAAAAGA AAAAACTTGC ATGCTGCTTC AATTGTGAAT TGAAAAACTG
3251  TCCACTTTGG GAAAACAAGG AATCGGTTTC CGACCAAAAC ATTCCGTTTA
3301  CATTCTCAAC CGTAACAGGA TTTCCTCCTC TCAGTACTCT GTCTGTTTAC
3351  TATCCTCAAC TTCTCAAGGT AATGTTGGAA ATACATACTA TGTCAAGGTG
3401  CTGTTGTCAA AGCTTTGCTG TTTATTTTTT TATCCCCACA AGATGAAAAA
3451  AAATATATAA AATATATATA TATATAAAAT TTATTCATTG ACATGTGTTC
3501  TGGATTAATA TAATTCATTT TGTATGTTGT GAAGTTGTTT GCAATATTAA
3551  ATTGAAATAT TTGAAGAAAT AAAATTACTA TAGGCAACTG AAAAACAAAA
3601  CCAATGTCAA TAAAGTTTGA GCTCTCCCTT TACAGGTCGA AATTTGGCAC
3651  ATGCTGTGCA GAGAACATCT TCTCTCGCAG GCAAACATAC TTTGGATCCT
3701  ACATTCATAT GATTTCAAAA GGGATAATGA TAGATATAAG TATATACACT
3751  ACAGTATATA AGTATTTATT TCCCATCCTC TCAACATATA TAGTTGAAGT
3801  CAGAATTATT AGCCTCCCCC CTGTTTCTTT GTTCCCCAAT TTCTGTTTAA
3851  TAGAGAGAAG ATTTTTTTAA CACATTTCTG AACATATTAG TTTTAATAAC
```

FIG. 10C

```
3901  TAATACCTGA TTTATTTTAT CTTTGCCATG ATGACAGTAA ATAATATTTG
3951  ACTTGATATT TGTCTAGACA TTTCTTTACA GCTTAAAGTG ACATTTAAAG
4001  GCTTAACCAG GTTAACTAGG CAGGTTAGGG TAATTAGGCA AGTTATTTTA
4051  TAACAATGGT TTGTTCTGTA GACTATCAAC TATATAGCTT AAAGGGGATA
4101  ATAATTTTGT CCTTAAATTA TTATTATTTT TTTTTATTAA AAACTGCTTT
4151  TATTCTAGTC AAATCAAAAT AAATAAGACT TTCTCCTGAA GAGAAAATAT
4201  TATCAGGCAT ACTGTGAAAA TTTCCATGCC CTGTTAAACA TCATTTGGTA
4251  AATATAAAAA GAATAATAAT AAATTAAAGG GGGGCTAATA GTTCTGACTT
4301  CAACTGTATG TCTATATCCG TATTACCAAG CTAATGTGAA ATCTCAAAGC
4351  CAGAAATGCA GACGAACACA TCCATCCAAT GTAAATTCTG ATGTGTTCTG
4401  TGGAACAACA AACACTCTAG AAAGTTCTCA GGTAAGACTT GATATGTAAA
4451  TTCTATGGAA ACCAGTCTCT CATGTAATGT TGTCCAGAGG GAGAAGGCAA
4501  TCATCACTAG CACTAAGAGA TTAGGATTTT CTTTTGTCTG TAGGATAGAT
4551  CAATGAAGTC AACACTCCAA TGCACTCTGC GTGATATCTG ATACACCTGA
4601  ACACAGACAC AGACCTATAC ACAAACCTGC TTTCCTTCAA AGGTTGTTAT
4651  CAGACAACTG AACAGAAATC TGTCTGACAC TGATACACTG CCACAGATAA
4701  GGGAGGAGTT TCATCTGTTC ATGGTAAGTA TCTCTGCATC ATGAGACACA
4751  TGGGCAGGAC CATAAAGGAT GCTCAGGCGG AAAGTCAAAA CTGATTATAA
4801  GTGCATCCTT TATCAGAAAC ACAACTCAAA TTAAATTTGT GTACCCAAGG
4851  ATATTGATAT GAAAGCATAA TAATAGCTAT CAGCCTTGCT TAATGAGTAA
4901  GTGTTTGCTT AACCTTATAG GAACAAATAT GAAGCTGCAA AATATAAATC
4951  AATGGTGACT GGACTAGATA AAGAAATGGA CAATAAAACA TTCTTCTGGT
5001  GCATTTTATC TGAGAAACAA CTTGCATTAT TTTTGTGAGG ATCAGATTTT
5051  CCCCAGTTCA AAGTAGTCCT TGGTAAGACC CAGCAGGGGT CGACGATCGA
5101  CGCGTAAATT GTAAGCGTTA ATATTTGTT AAAATTCGCG TTAAATTTTT
5151  GTTAAATCAG CTCATTTTTT AACCAATAGG CCGAAATCGG CAAAATCCCT
```

FIG. 10D

5201 TATAAATCAA AAGAATAGAC CGAGATAGGG TTGAGTGTTG TTCCAGTTTG

5251 GAACAAGAGT CCACTATTAA AGAACGTGGA CTCCAACGTC AAAGGGCGAA

5301 AAACCGTCTA TCAGGGCGAT GGCCCACTAC GTGAACCATC ACCCTAATCA

5351 AGTTTTTTGG GGTCGAGGTG CCGTAAAGCA CTAAATCGGA ACCCTAAAGG

5401 GAGCCCCCGA TTTAGAGCTT GACGGGGAAA GCCGGCGAAC GTGGCGAGAA

5451 AGGAAGGGAA GAAAGCGAAA GGAGCGGGCG CTAGGGCGCT GGCAAGTGTA

5501 GCGGTCACGC TGCGCGTAAC CACCACACCC GCCGCGCTTA ATGCGCCGCT

5551 ACAGGGCGCG TCAGGTGGCA CTTTTCGGGG AAATGTGCGC GGAACCCCTA

5601 TTTGTTTATT TTTCTAAATA CATTCAAATA TGTATCCGCT CATGAGACAA

5651 TAACCCTGAT AAATGCTTCA ATAATATTGA AAAAGGAAGA ATCCTGAGGC

5701 CGGGCCATAA CTTCGTATAA TGTATGCTAT ACGAAGTTAT CCATGGGCCC

5751 CCCCTCGACA TGAGTAAACT TGGTCTGACA GTTACCAATG CTTAATCAGT

5801 GAGGCACCTA TCTCAGCGAT CTGTCTATTT CGTTCATCCA TAGTTGCCTG

5851 ACTCCCCGTC GTGTAGATAA CTACGATACG GGAGGGCTTA CCATCTGGCC

5901 CCAGTGCTGC AATGATACCG CGAGACCCAC GCTCACCGGC TCCAGATTTA

5951 TCAGCAATAA ACCAGCCAGC CGGAAGGGCC GAGCGCAGAA GTGGTCCTGC

6001 AACTTTATCC GCCTCCATCC AGTCTATTAA TTGTTGCCGG GAAGCTAGAG

6051 TAAGTAGTTC GCCAGTTAAT AGTTTGCGCA ACGTTGTTGC CATTGCTACA

6101 GGCATCGTGG TGTCACGCTC GTCGTTTGGT ATGGCTTCAT TCAGCTCCGG

6151 TTCCCAACGA TCAAGGCGAG TTACATGATC CCCCATGTTG TGCAAAAAAG

6201 CGGTTAGCTC CTTCGGTCCT CCGATCGTTG TCAGAAGTAA GTTGGCCGCA

6251 GTGTTATCAC TCATGGTTAT GGCAGCACTG CATAATTCTC TTACTGTCAT

6301 GCCATCCGTA AGATGCTTTT CTGTGACTGG TGAGTACTCA ACCAAGTCAT

6351 TCTGAGAATA GTGTATGCGG CGACCGAGTT GCTCTTGCCC GGCGTCAATA

6401 CGGGATAATA CCGCGCCACA TAGCAGAACT TTAAAAGTGC TCATCATTGG

6451 AAAACGTTCT TCGGGGCGAA AACTCTCAAG GATCTTACCG CTGTTGAGAT

FIG. 10E

```
6501  CCAGTTCGAT GTAACCCACT CGTGCACCCA ACTGATCTTC AGCATCTTTT
6551  ACTTTCACCA GCGTTTCTGG GTGAGCAAAA ACAGGAAGGC AAAATGCCGC
6601  AAAAAGGGA ATAAGGGCGA CACGGAAATG TTGAATACTC ATACTCTTCC
6651  TCAGGTTACT CATATATACT TTAGATTGAT TTAAAACTTC ATTTTTAATT
6701  TAAAGGATC TAGGTGAAGA TCCTTTTTGA TAATCTCATG ACCAAAATCC
6751  CTTAACGTGA GTTTTCGTTC CACTGAGCGT CAGACCCCGT AGAAAAGATC
6801  AAAGGATCTT CTTGAGATCC TTTTTTTCTG CGCGTAATCT GCTGCTTGCA
6851  AACAAAAAAA CCACCGCTAC CAGCGGTGGT TTGTTTGCCG GATCAAGAGC
6901  TACCAACTCT TTTTCGAAG GTAACTGGCT TCAGCAGAGC GCAGATACCA
6951  AATACTGTCC TTCTAGTGTA GCCGTAGTTA GGCCACCACT TCAAGAACTC
7001  TGTAGCACCG CCTACATACC TCGCTCTGCT AATCCTGTTA CCAGTGGCTG
7051  CTGCCAGTGG CGATAAGTCG TGTCTTACCG GGTTGGACTC AAGACGATAG
7101  TTACCGGATA AGGCGCAGCG GTCGGGCTGA ACGGGGGGTT CGTGCACACA
7151  GCCCAGCTTG GAGCGAACGA CCTACACCGA ACTGAGATAC CTACAGCGTG
7201  AGCTATGAGA AAGCGCCACG CTTCCCGAAG GGAGAAAGGC GGACAGGTAT
7251  CCGGTAAGCG GCAGGGTCGG AACAGGAGAG CGCACGAGGG AGCTTCCAGG
7301  GGGAAACGCC TGGTATCTTT ATAGTCCTGT CGGGTTTCGC CACCTCTGAC
7351  TTGAGCGTCG ATTTTGTGA TGCTCGTCAG GGGGGCGGAG CCTATGGAAA
7401  AACGCCAGCA ACGCGGCCTT TTTACGGTTC CTGGCCTTTT GCTGGCCTTT
7451  TGCTCACATG TTCTTTCCTG CGTTATCCCC TGATTCTGTG ATAACCGTA
7501  TTACCGCC
```

FIG. 10F

```
   1  ACCACCGCGG TGGCGGCCGC TCCGGAGTGC TCCTAATGAG AAGCAGAGTG
  51  AAGAGTGATT TATTTATGGA TTACCTAGCT GGAACAGCCC TAATGCACAG
 101  TGTGAGAGTG TGCATGAGTG TATGTGTGTG TGTATGCGCG CGCCTGTGTG
 151  TGTGTTTTAC CTCTCTTGGA GTCATGTCGC TCAGTAATTG CTGATGCAAC
 201  TCTTTGTCAT CCAGGGTTTG CCCTCTCCTC CTGTGAACCT ATGGGATGAG
 251  TTATATTCAT CTTGGCTTGT CCCTATAGGA GAGAGGAAGG GGACTGTAAG
 301  TGCGAGTATG TCAAAATGAG TGAAGGTGAA AGTATATTTG TATAATTTTA
 351  TATTTGAAAG TGTTCATGTG TAGCAGTGCA AAAGGTTGA AGATGAGGTG
 401  ACAAAGAAAC AGAAAGGTGG AGATGGAAAT AAGTAAAGAA AGAGGGAGTT
 451  TGTGTGTGTA TGTGTGCGAG TGTGTGTAAG TGTGTGTGAG AAGGCAGGTG
 501  TTAGCATCCA CTCCCATGCT GGGAACAGCT AGGTTTGAAA CCGCTCCACC
 551  TCATTACCTT ATGCAGGGAA TAATCATCAT CACTATACAC AAAACTCATC
 601  AATATAAATC TTGCACTGGA CAAGATCCAA AAGCACTTGC AGCTTGGTGA
 651  AAGTATGGGG CTAATGATGT GGTGAAGCAT AGGGTGAAAG AACAAGGAAT
 701  GCTTTTGCTA AACTTCTCCA GGAAGGTCAC GTTAAATAAG AATTAAACAA
 751  TAAAGCCACA GTTGAAGAGC AACATTATAT CACCTCTATG TTTTTAAACA
 801  TGTTTGACCG TTTACAAAAA TCAAACAAAC CACTCCCAGT TATCAGAGGA
 851  ATAGAACTGA CACCGGAAGA ACAATGAATA GTATTAAAAT CAATGAACCA
 901  GCCAACATCT GGCACATAAG CTCCTTTGGC AGACGGGGGG CTCAAACCTG
 951  ACAATAGTTT AAAATATCAC ATACAGAGAA GACTAGGGAA TAATAGGACC
1001  TTGATGTGGT GGGAGCAAGG AGTGAGCTCT TTACTTTGAA GCTACCTTTG
1051  TGGAGTCACA ATTGCAAATA TCAATTTCAG CAGATGATCT ATAGTCTTGT
1101  CACAAAAAGG TGTTTCAGAT TAACCTAACG GCTGTCCATT AGGATGCTGG
1151  TGCAGCATTT GTTCGCAGCT AAGACAGTGA ATTTAAAGTG ATTTAGATGG
1201  CAAATGTAAT AACTTAAAAC CATAATTTAC AGTTTTACAG GCAAGTGAAA
1251  TAACATATAA ATTATAATTT TGCCAATTAT ACAAAGCTGT AGCTACGTGA
```

FIG. 11A

```
1301  AGCAAAACAG GTGTTCACTA GAGCTAGGCT AATTTCTCAT GTCTTTATAC
1351  AAATAGTCAA GGAAAACAAC ACGAAACATC AAACCAAACG GATATATACA
1401  TGAAACAGCA CAAGCATACG CATAAGCGTA TGAGATTCAC TTTGTATCAG
1451  CACACAAAGG AATCGTATTT TATATATACC TTCATCAGTA ATGACGAAGA
1501  ATGTGAACAA AAATGTCAAA AGCCCACACT AACTCAGTGG TCGTCAGGAG
1551  AAGCCTGCTC GAGAAAAGAA TGCGATGATT TAAAAATCGA TGGGCGTTTA
1601  AAATCACCCC AAGCCTCTAT ATGTCCAGGA ATTAAAATAG GTTTCTGTCA
1651  TATGTTGCTC GGTAAACGCC ATAATAACAC ACTTTCCGGT TATTCGTTAG
1701  GAATAAGCAT CTGAGCCTTC ACTTGGTTGG CGCTCGCGCT TGAGTCACAT
1751  GTTGCAACGT CACGGCAGTA GTTAGTTACT GTAGTCGCGA GGAATGAAGC
1801  CGTCATTTCA AGCTGGAGAG CTCTCTCAAT GCGCACTACA CTGCGAGCGC
1851  TCACCATGTC ATCCAACTGC TTCAACTCAA CTCCAAGGA TCCGCTCAGT
1901  CATGGGAGTC CATTACCTCA ACCATGCAAT TTCCACCATC AATAATTTAA
1951  TCTATTTGCT CAAAAGCTGA AGAGACAACT TGCAGCTGCT GCTTGGCGAA
2001  GAGCGGACGA ATATCGCAGA ATAGTTGCGC GGAGGTCTTA TCCAAAACAT
2051  CCCAGATGAC ACTGTCCTGC TGAATGGTCT CCTTTACGAC TGGACAGTAC
2101  CCGGGATAAT ATGGCCACAA CCATGGCCTC CTCCGAGAAC GTCATCACCG
2151  AGTTCATGCG CTTCAAGGTG CGCATGGAGG GCACCGTGAA CGGCCACGAG
2201  TTCGAGATCG AGGGCGAGGG CGAGGGCCGC CCCTACGAGG GCCACAACAC
2251  CGTGAAGCTG AAGGTGACCA AGGGCGGCCC CCTGCCCTTC GCCTGGGACA
2301  TCCTGTCCCC CCAGTTCCAG TACGGCTCCA AGGTGTACGT GAAGCACCCC
2351  GCCGACATCC CCGACTACAA GAAGCTGTCC TTCCCCGAGG GCTTCAAGTG
2401  GGAGCGCGTG ATGAACTTCG AGGACGGCGG CGTGGCGACC GTGACCCAGG
2451  ACTCCTCCCT GCAGGACGGC TGCTTCATCT ACAAGGTGAA GTTCATCGGC
2501  GTGAACTTCC CCTCCGACGG CCCCGTGATG CAGAAGAAGA CCATGGGCTG
2551  GGAGGCCTCC ACCGAGCGCC TGTACCCCCG CGACGGCGTG CTGAAGGGCG
```

FIG. 11B

```
2601  AGACCCACAA GGCCCTGAAG CTGAAGGACG GCGGCCACTA CCTGGTGGAG
2651  TTCAAGTCTA TCTACATGGC CAAGAAGCCC GTGCAGCTGC CCGGCTACTA
2701  CTACGTGGAC GCCAAGCTGG ACATCACCTC CCACAACGAG GACTACACCA
2751  TCGTGGAGCA GTACGAGCGC ACCGAGGGCC GCCACCACCT GTTCCTGTAG
2801  CGAATTCGGC CGCATTGACC ATTAAGAGGG GCAGATAGTG TACACAATGT
2851  ATAGATTTTA TTGAGAGTTC TAAAAAAGA GAGAGAGAAA GAGAAAATAT
2901  CTATTTGTAT ATACATAACA GGGTAAATTA TTCAGTCAGA TAAAAATTTT
2951  ATGGACTGCA TGTAAAAAAG AAAAAGTTTA TACAGTAAGT GATACTACAG
3001  TCTATTTATT GAACATATTC ATGACCTTGT AAACAATTAA AAAAAGATCT
3051  GATCAGTCAT TTGCGCCCAG TTCAAATTAC TATATCACAT TCCTCAAGAC
3101  ATTGTGTTTT TTACGTTGCC AAGATTTTGA GAGATGAGGA GAGGAGGGGG
3151  TGAGGAAGAA TTACATTCAA GAAAGAAAAA AAAAGAAAAA AAAAAGAAAA
3201  AACTTGCATG CTGCTTCAAT TGTGAATTGA AAAACTGTCC ACTTTGGGAA
3251  AACAAGGAAT CGGTTTCCGA CCAAAACATT CCGTTTACAT TCTCAACCGT
3301  AACAGGATTT CCTCCTCTCA GTACTCTGTC TGTTTACTAT CCTCAACTTC
3351  TCAAGGTAAT GTTGGAAATA CATACTATGT CAAGGTGCTG TTGTCAAAGC
3401  TTTGCTGTTT ATTTTTTTAT CCCCACAAGA TGAAAAAAAA TATATAAAAT
3451  ATATATATAT ATAAAATTTA TTCATTGACA TGTGTTCTGG ATTAATATAA
3501  TTCATTTTGT ATGTTGTGAA GTTGTTTGCA ATATTAAATT GAAATATTTG
3551  AAGAAATAAA ATTACTATAG GCAACTGAAA AACAAAACCA ATGTCAATAA
3601  AGTTTGAGCT CTCCCTTTAC AGGTCGAAAT TTGGCACATG CTGTGCAGAG
3651  AACATCTTCT CTCGCAGGCA AACATACTTT GGATCCTACA TTCATATGAT
3701  TTCAAAGGG ATAATGATAG ATATAAGTAT ATACACTACA GTATATAAGT
3751  ATTTATTTCC CATCCTCTCA ACATATATAG TTGAAGTCAG AATTATTAGC
3801  CTCCCCCCTG TTTCTTTGTT CCCCAATTTC TGTTTAATAG AGAGAAGATT
3851  TTTTTAACAC ATTTCTGAAC ATATTAGTTT TAATAACTAA TACCTGATTT
```

FIG. 11C

```
3901  ATTTTATCTT TGCCATGATG ACAGTAAATA ATATTTGACT TGATATTTGT
3951  CTAGACATTT CTTTACAGCT TAAAGTGACA TTTAAAGGCT TAACCAGGTT
4001  AACTAGGCAG GTTAGGGTAA TTAGGCAAGT TATTTTATAA CAATGGTTTG
4051  TTCTGTAGAC TATCAACTAT ATAGCTTAAA GGGGATAATA ATTTTGTCCT
4101  TAAATTATTA TTATTTTTTT TTATTAAAAA CTGCTTTTAT TCTAGTCAAA
4151  TCAAAATAAA TAAGACTTTC TCCTGAAGAG AAAATATTAT CAGGCATACT
4201  GTGAAAATTT CCATGCCCTG TTAAACATCA TTTGGTAAAT ATAAAAAGAA
4251  TAATAATAAA TTAAGGGGG GCTAATAGTT CTGACTTCAA CTGTATGTCT
4301  ATATCCGTAT TACCAAGCTA ATGTGAAATC TCAAAGCCAG AAATGCAGAC
4351  GAACACATCC ATCCAATGTA AATTCTGATG TGTTCTGTGG AACAACAAAC
4401  ACTCTAGAAA GTTCTCAGGT AAGACTTGAT ATGTAAATTC TATGGAAACC
4451  AGTCTCTCAT GTAATGTTGT CCAGAGGGAG AAGGCAATCA TCACTAGCAC
4501  TAAGAGATTA GGATTTTCTT TTGTCTGTAG GATAGATCAA TGAAGTCAAC
4551  ACTCCAATGC ACTCTGCGTG ATATCTGATA CACCTGAACA CAGACACAGA
4601  CCTATACACA AACCTGCTTT CCTTCAAAGG TTGTTATCAG ACAACTGAAC
4651  AGAAATCTGT CTGACACTGA TACACTGCCA CAGATAAGGG AGGAGTTTCA
4701  TCTGTTCATG GTAAGTATCT CTGCATCATG AGACACATGG GCAGGACCAT
4751  AAAGGATGCT CAGGCGGAAA GTCAAAACTG ATTATAAGTG CATCCTTTAT
4801  CAGAAACACA ACTCAAATTA AATTTGTGTA CCCAAGGATA TTGATATGAA
4851  AGCATAATAA TAGCTATCAG CCTTGCTTAA TGAGTAAGTG TTTGCTTAAC
4901  CTTATAGGAA CAAATATGAA GCTGCAAAAT ATAAATCAAT GGTGACTGGA
4951  CTAGATAAAG AAATGGACAA TAAAACATTC TTCTGGTGCA TTTTATCTGA
5001  GAAACAACTT GCATTATTTT TGTGAGGATC AGATTTTCCC CAGTTCAAAG
5051  TAGTCCTTGG TAAGACCCAG CAGGGGTCGA CGATCGACGC GTAAATTGTA
5101  AGCGTTAATA TTTTGTTAAA ATTCGCGTTA AATTTTTGTT AAATCAGCTC
5151  ATTTTTTAAC CAATAGGCCG AAATCGGCAA AATCCCTTAT AAATCAAAAG
```

FIG. 11D

```
5201  AATAGACCGA GATAGGGTTG AGTGTTGTTC CAGTTTGGAA CAAGAGTCCA
5251  CTATTAAAGA ACGTGGACTC CAACGTCAAA GGGCGAAAAA CCGTCTATCA
5301  GGGCGATGGC CCACTACGTG AACCATCACC CTAATCAAGT TTTTTGGGGT
5351  CGAGGTGCCG TAAAGCACTA AATCGGAACC CTAAAGGGAG CCCCCGATTT
5401  AGAGCTTGAC GGGGAAAGCC GGCGAACGTG GCGAGAAAGG AAGGGAAGAA
5451  AGCGAAAGGA GCGGGCGCTA GGGCGCTGGC AAGTGTAGCG GTCACGCTGC
5501  GCGTAACCAC CACACCCGCC GCGCTTAATG CGCCGCTACA GGGCGCGTCA
5551  GGTGGCACTT TTCGGGGAAA TGTGCGCGGA ACCCTATTT GTTTATTTTT
5601  CTAAATACAT TCAAATATGT ATCCGCTCAT GAGACAATAA CCCTGATAAA
5651  TGCTTCAATA ATATTGAAAA AGGAAGAATC CTGAGGCCGG GCCATAACTT
5701  CGTATAATGT ATGCTATACG AAGTTATCCA TGGGCCCCCC CTCGACATGA
5751  GTAAACTTGG TCTGACAGTT ACCAATGCTT AATCAGTGAG GCACCTATCT
5801  CAGCGATCTG TCTATTTCGT TCATCCATAG TTGCCTGACT CCCCGTCGTG
5851  TAGATAACTA CGATACGGGA GGGCTTACCA TCTGGCCCCA GTGCTGCAAT
5901  GATACCGCGA GACCCACGCT CACCGGCTCC AGATTTATCA GCAATAAACC
5951  AGCCAGCCGG AAGGGCCGAG CGCAGAAGTG GTCCTGCAAC TTTATCCGCC
6001  TCCATCCAGT CTATTAATTG TTGCCGGGAA GCTAGAGTAA GTAGTTCGCC
6051  AGTTAATAGT TTGCGCAACG TTGTTGCCAT TGCTACAGGC ATCGTGGTGT
6101  CACGCTCGTC GTTTGGTATG GCTTCATTCA GCTCCGGTTC CCAACGATCA
6151  AGGCGAGTTA CATGATCCCC CATGTTGTGC AAAAAAGCGG TTAGCTCCTT
6201  CGGTCCTCCG ATCGTTGTCA GAAGTAAGTT GGCCGCAGTG TTATCACTCA
6251  TGGTTATGGC AGCACTGCAT AATTCTCTTA CTGTCATGCC ATCCGTAAGA
6301  TGCTTTTCTG TGACTGGTGA GTACTCAACC AAGTCATTCT GAGAATAGTG
6351  TATGCGGCGA CCGAGTTGCT CTTGCCCGGC GTCAATACGG GATAATACCG
6401  CGCCACATAG CAGAACTTTA AAAGTGCTCA TCATTGGAAA ACGTTCTTCG
6451  GGGCGAAAAC TCTCAAGGAT CTTACCGCTG TTGAGATCCA GTTCGATGTA
```

FIG. 11E

```
6501  ACCCACTCGT GCACCCAACT GATCTTCAGC ATCTTTTACT TTCACCAGCG
6551  TTTCTGGGTG AGCAAAAACA GGAAGGCAAA ATGCCGCAAA AAGGGAATA
6601  AGGGCGACAC GGAAATGTTG AATACTCATA CTCTTCCTCA GGTTACTCAT
6651  ATATACTTTA GATTGATTTA AAACTTCATT TTTAATTTAA AAGGATCTAG
6701  GTGAAGATCC TTTTTGATAA TCTCATGACC AAAATCCCTT AACGTGAGTT
6751  TTCGTTCCAC TGAGCGTCAG ACCCCGTAGA AAGATCAAA GGATCTTCTT
6801  GAGATCCTTT TTTTCTGCGC GTAATCTGCT GCTTGCAAAC AAAAAAACCA
6851  CCGCTACCAG CGGTGGTTTG TTTGCCGGAT CAAGAGCTAC CAACTCTTTT
6901  TCCGAAGGTA ACTGGCTTCA GCAGAGCGCA GATACCAAAT ACTGTCCTTC
6951  TAGTGTAGCC GTAGTTAGGC CACCACTTCA AGAACTCTGT AGCACCGCCT
7001  ACATACCTCG CTCTGCTAAT CCTGTTACCA GTGGCTGCTG CCAGTGGCGA
7051  TAAGTCGTGT CTTACCGGGT TGGACTCAAG ACGATAGTTA CCGGATAAGG
7101  CGCAGCGGTC GGGCTGAACG GGGGGTTCGT GCACACAGCC CAGCTTGGAG
7151  CGAACGACCT ACACCGAACT GAGATACCTA CAGCGTGAGC TATGAGAAAG
7201  CGCCACGCTT CCCGAAGGGA GAAAGGCGGA CAGGTATCCG GTAAGCGGCA
7251  GGGTCGGAAC AGGAGAGCGC ACGAGGGAGC TTCCAGGGGG AAACGCCTGG
7301  TATCTTTATA GTCCTGTCGG GTTTCGCCAC CTCTGACTTG AGCGTCGATT
7351  TTTGTGATGC TCGTCAGGGG GGCGGAGCCT ATGGAAAAAC GCCAGCAACG
7401  CGGCCTTTTT ACGGTTCCTG GCCTTTTGCT GGCCTTTTGC TCACATGTTC
7451  TTTCCTGCGT TATCCCCTGA TTCTGTGGAT AACCGTATTA CCGCC
```

FIG. 11F

```
                     SEQUENCE LISTING

<160> NUMBER OF SEQ ID NOS: 5

<210> SEQ ID NO 1
<211> LENGTH: 1846
<212> TYPE: DNA
<213> ORGANISM: Danio rerio
<220> FEATURE:
<222> LOCATION:
<223> OTHER INFORMATION:

<400> SEQUENCE: 1
atgggatcca tgttgttttt gtgctcctaa tgagaagcag agtgatttat              50
ttatgggatt acctagctgg aacagcccta atgcacagtg tgagagtgtg             100
catgagtgta tgtgtgtgtg tgtgcgcgcg cctgtgtgtg tgttttacct             150
ctcttggagt catgtcgctc agtaattgct gatgcaactc tttgtcatcc             200
agggtttgcc ctctcctcct gtgaacctat gggatgagtt atattcatct             250
tggcttgtcc ctataggaga gaggaagggg actgtaagtg cgagtatgtc             300
aaaatgagtg aaggtgaaag tatatttgta taattttata tttgaaagtg             350
ttcatgtgta gcagtgcaaa aaggttgaag atgaggtgac aaagaaacag             400
aaaggtggag atggaaataa gtaaagaaag aggaagtttg tgtgtgtatg             450
tgtgccaagt gtgtgtatgt gtgtgtgaga aggcaaggtg ttagcatcca             500
ctcccatgct gggaacagct aggtttgaaa ccgctccacc tcattaacctt            550 atgcagggaa taatcatcat cactatacat aaaactcatc aatataaatc             600
ttgcactgga caaaatccaa aagcacttgc agcttggtga aagtatgggg             650
ctaatgatgt ggtgaagcat agggtgaaag aacaaggaat gctttcgcta             700
aacttctcca ggaaggtcac gttaaataag aattaaacaa taaagccgca             750
gttgaagagc aacattatat cacctctatg tttttaaaca tgtttgacca             800
```

-continued

| | |
|---|---|
| tttacaaaaa ttaaacaaac cactcccagt tatcagagga atagaactga | 850 |
| caccggaaga acaatgaata gtattaaaat caatgaacca gccaacatct | 900 |
| ggcacataag ctcctttggc agacgggggg ctcaaacctg acaatagttt | 950 |
| aaaatatcac atacagagaa gactagggaa taataggacc ttgatgtggt | 1000 |
| gggagcaagg agtgagctct ttactttgaa gctacctttg tggagtcaca | 1050 |
| attgcaaata tcaatttcag cagatgatct atagtcttgt cacaaaaagg | 1100 |
| tgtttcagat taacctaatg gctgtccatt aggatgctgg tgcagcattt | 1150 |
| gttcgcagct aagacagtga atttaaagtg atttagatgg caaatgtaat | 1200 |
| aacttaaaac cataatttac agttttacag gcaagtgaaa taacatataa | 1250 |
| attataattt tgccaattat acacagctgt agctacgtga aacaaaacag | 1300 |
| gtgttcacta gagctaggct aatttctcat gtctttatac aaatagtcat | 1350 |
| ggaaaacaac acgaaacatc aaaccaaacg gatatataca tgaaacagca | 1400 |
| caagcatacg cataagcgta tgagattcac tttgtatcag cacacaaagg | 1450 |
| aatcgtattt tatatatacc ttcatcagta atgacgaaga atgtgaacaa | 1500 |
| aaatgtcaaa agcccacact aactcagtgg tcgtcaggag aagcctgctc | 1550 |
| gagaaaagaa tgcgatgatt taaaaatcga tgggcgttta aaatcacccc | 1600 |
| aagcctctat atgtccagga attaaaatag gtttctgtca tatgttgctc | 1650 |
| ggtaaacgcc ataataacac actttccggt tattcgttag gaataagcat | 1700 |
| ctgaggcttc acttggttgg cgctcgcgct tgagtcacat gttgcaacgt | 1750 |
| cacggcagta gttagttact gtagtcgcga ggaatgaagc cgtcatttca | 1800 |
| agctggagag ctctctcaat gcgcactaca ctgcgagcgc tcacca | 1846 |

<210> SEQ ID NO 2
<211> LENGTH: 1839
<212> TYPE: DNA
<213> ORGANISM: Danio rerio
<220> FEATURE:

<400> SEQUENCE: 2

| | |
|---|---|
| gtctgtggtg gtggtggtgt caactttgtg ctgtatgtgc agttctgaat | 50 |
| gggatccatg ttgttttttgt gctcctaatg agaagcagag tgatttattt | 100 |
| atggattacc tagctggaac agccctaatg cacagtgtga gagtgtgcat | 150 |
| gagtgtatgt gtgtgtgtat gcgcgcgcct gtgtgtgtgt tttacctctc | 200 |
| ttggagtcat gtcgctcagt aattgctgat gcaactcttt gtcatccagg | 250 |
| gtttgccctc tcctcctgtg aacctatggg atgagttata ttcatcttgg | 300 |
| cttgtcccta taggagagag gaaggggact gtaagtgcga gtatgtcaaa | 350 |
| atgagtgaag gtgaaagtat atttgtataa ttttatattt gaaagtgttc | 400 |
| atgtgtagca gtgcaaaaag gttgaagatg aggtgacaaa gaaacagaaa | 450 |
| ggtggagatg gaaataagta aagaaagagg gagtttgtgt gtgtatgtgt | 500 |
| gcgagtgtgt gtaagtgtgt gtgagaaggc aggtgttagc atccactccc | 550 |
| atgctgggaa cagctaggtt tgaaaccgct ccacctcatt accttatgca | 600 |
| gggaataatc atcatcacta tacacaaaac tcatcaatat aaatcttgca | 650 |
| ctggacaaga tccaaaagca cttgcagctt ggtgaaagta tggggctaat | 700 |

```
gatgtggtga agcatagggt gaaagaacaa ggaatgcttt tgctaaactt          750
ctccaggaag gtcacgttaa ataagaatta aacaataaag ccacagttga          800
agagcaacat tatatcacct ctatgttttt aaacatgttt gaccgtttac          850
aaaaatcaaa caaaccactc ccagttatca gaggaataga actgacaccg          900
gaagaacaat gaatagtatt aaaatcaatg aaccagccaa catctggcac          950
ataagctcct ttggcagacg gggggctcaa acctgacaat agtttaaaat         1000
atcacataca gagaagacta gggaataata ggaccttgat gtggtgggag         1050
caaggagtga gctctttact ttgaagctac ctttgtggag tcacaattgc         1100
aaatatcaat ttcagcagat gatctatagt cttgtcacaa aaaggtgttt         1150
cagattaacc taacggctgt ccattaggat gctggtgcaa catttgttcg         1200
cagctaagac agtgaattta aagtgattta gatggcaaat gtaataactt         1250
aaaaccataa tttacagttt tacaggcaag tgaaataaca tataaattat         1300
aattttgcca attatacaaa gctgtagcta cgtgaagcaa acaggtgtt          1350 cactagagct aggctaattt ctcatgtctt tatacaaata gtcaaggaaa         1400
acaacacgaa acatcaaacc aaacggatat atacatgaaa cagcacaagc         1450
atacgcataa gcgtatgaga ttcactttgt atcagcacac aaaggaatcg         1500
tattttatat ataccttcat cagtaatgac gaagaatgtg aacaaaaatg         1550
tcaaaagccc acactaactc agtggtcgtc aggagaagcc tgctcgagaa         1600
aagaatgcga tgatttaaaa atcgatgggc gtttaaaatc accccaagcc         1650
tctatatgtc caggaattaa aataggtttc tgtcatatgt tgctcggtaa         1700
acgccataat aacacacttt ccggttattc gttaggaata agcatctgag         1750
ccttcacttg gttggcgctc gcgcttgagt cacatgttgc aacgtcacgg         1800
cagtagttag ttactgtagt cgcgaggaat gaagccgtc                     1839
```

<210> SEQ ID NO 3
<211> LENGTH: 6428
<212> TYPE: DNA
<213> ORGANISM: Artificial Sequence
<220> FEATURE:
<221> NAME/KEY: Unsure
<222> LOCATION: 748, 763, 936, 1359
<223> OTHER INFORMATION: Synthesized

<400> SEQUENCE: 3

```
agcgcccaat acgcaaaccg cctctccccg cgcgttggcc gattcattaa           50
tgcagctggc acgacaggtt tcccgactgg aaagcgggca gtgagcgcaa          100
cgcaattaat gtgagttagc tcactcatta ggcaccccag gctttacact          150
ttatgcttcc ggctcgtatg ttgtgtggaa ttgtgagcgg ataacaattt          200
cacacaggaa acagctatga ccatgattac gccaagcttg catgcctgca          250
ggtcgactct agattctgaa tgggatccat gttgttttg tgctcctaat           300 gagaagcaga gtgatttatt tatgggatta cctagctgga acagccctaa          350
tgcacagtgt gagagtgtgc atgagtgtat gtgtgtgtgt gtgcgcgcgc          400
ctgtgtgtgt gttttaccte tcttggagtc atgtcgctca gtaattgctg          450
atgcaactct ttgtcatcca gggttttgccc tctcctcctg tgaacctatg         500
ggatgagtta tattcatctt ggcttgtccc tataggagag aggaaggga           550
```

-continued

| | |
|---|---|
| ctgtaagtgc gagtatgtca aaatgagtga aggtgaaagt atatttgtat | 600 |
| aattttatat ttgaaagtgt tcatgtgtag cagtgcaaaa aggttgaaga | 650 |
| tgaggtgaca aagaaacaga aaggtggaga tggaaataag taaagaaaga | 700 |
| ggaagtttgt gtgtgtatgt gtgccaagtg tgtgtatgtg tgtgtganaa | 750 |
| ggcaaggtgt tancatccac tcccatgctg ggaacagcta ggtttgaaac | 800 |
| cgctccacct cattacctta tgcagggaat aatcatcatc actatacata | 850 |
| aaactcatca atataaatct tgcactggac aaaatccaaa agcacttgca | 900 |
| gcttggtgaa agtatggggc taatgatgtg gtgaancata gggtgaaaga | 950 |
| acaaggaatg ctttcgctaa acttctccag gaaggtcacg ttaaataaga | 1000 |
| attaaacaat aaagccgcag ttgaagagca acattatatc acctctatgt | 1050 |
| ttttaaacat gtttgaccat ttacaaaaat taaacaaacc actcccagtt | 1100 |
| atcagaggaa tagaactgac accggaagaa caatgaatag tattaaaatc | 1150 |
| aatgaaccag ccaacatctg gcacataagc tcctttggca gacgggggc | 1200 |
| tcaaacctga caatagttta aaatatcaca tacagagaag actagggaat | 1250 |
| aataggacct tgatgtggtg ggagcaagga gtgagctctt tactttgaag | 1300 |
| ctacctttgt ggagtcacaa ttgcaaatat caatttcagc agatgatcta | 1350 |
| tagtcttgnc acaaaaaggt gtttcagatt aacctaatgg ctgtccatta | 1400 |
| ggatgctggt gcagcatttg ttcgcagcta agacagtgaa tttaaagtga | 1450 |
| tttagatggc aaatgtaata acttaaaacc ataatttaca gttttacagg | 1500 |
| caagtgaaat aacatataaa ttataatttt gccaattata cacagctgta | 1550 |
| gctacgtgaa acaaaacagg tgttcactag agctaggcta atttctcatg | 1600 |
| tctttataca aatagtcatg gaaaacaaca cgaaacatca aaccaaacgg | 1650 |
| atatatacat gaaacagcac aagcatacgc ataagcgtat gagattcact | 1700 |
| ttgtatcagc acacaaagga atcgtatttt atatatacct tcatcagtaa | 1750 |
| tgacgaagaa tgtgaacaaa aatgtcaaaa gcccacacta actcagtggt | 1800 |
| cgtcaggaga agcctgctcg agaaaagaat gcgatgattt aaaaatcgat | 1850 |
| gggcgtttaa aatcaccca agcctctata tgtccaggaa ttaaaatagg | 1900 |
| tttctgtcat atgttgctcg gtaaacgcca taataacaca cttccggtt | 1950 |
| attcgttagg aataagcatc tgaggcttca cttggttggc gctcgcgctt | 2000 |
| gagtcacatg ttgcaacgtc acggcagtag ttagttactg tagtcgcgag | 2050 |
| gaatgaagcc gtcatttcaa gctggagagc tctctcaatg cgcactacac | 2100 |
| tgcgagcgct caccatgtca tccaactgct tcaactcaac tccaagggga | 2150 |
| tccccgggta ccggtcgcca ccatggtgag caagggcgag gagctgttca | 2200 |
| ccggggtggt gcccatcctg gtcgagctgg acggcgacgt aaacggccac | 2250 |
| aagttcagcg tgtccggcga gggcgagggc gatgccacct acggcaagct | 2300 |
| gaccctgaag ttcatctgca ccaccggcaa gctgcccgtg ccctggccca | 2350 |
| ccctcgtgac caccctgacc tacggcgtgc agtgcttcag ccgctacccc | 2400 |
| gaccacatga agcagcacga cttcttcaag tccgccatgc ccgaaggcta | 2450 |
| cgtccaggag cgcaccatct tcttcaagga cgacggcaac tacaagaccc | 2500 |

```
gcgccgaggt gaagttcgag ggcgacaccc tggtgaaccg catcgagctg      2550
aagggcatcg acttcaagga ggacggcaac atcctggggc acaagctgga      2600
gtacaactac aacagccaca acgtctatat catggccgac aagcagaaga      2650
acggcatcaa ggtgaacttc aagatccgcc acaacatcga ggacggcagc      2700
gtgcagctcg ccgaccacta ccagcagaac acccccatcg cgacggcccc      2750
cgtgctgctg cccgacaacc actacctgag cacccagtcc gccctgagca      2800
aagaccccaa cgagaagcgc gatcacatgg tcctgctgga gttcgtgacc      2850
gccgccggga tcactctcgg catggacgag ctgtacaagt ccggactcag      2900
atctaagctg aaccctcctg atgagagtgg ccccggctgc atgagctgca      2950
agtgtgtgct ctcctgagga tcgatccacc ggatctagat aactgatcat      3000
aatcagccat accacatttg tagaggtttt acttgcttta aaaaacctcc      3050
cacacctccc cctgaacctg aaacataaaa tgaatgcaat tgttgttgtt      3100
aacttgttta ttgcagctta taatggttac aaataaagca atagcatcac      3150
aaatttcaca ataaagcat tttttcact gcattctagt tgtggtttgt        3200
ccaaactcat caatgtatct taacgcgtaa attgtaagcg ttaatatttt      3250
gttaaaattc gcgttaaatt tttgttaaat cagctcattt tttaaccaat      3300
aggccgaaat cggcaaaatc ccttataaat caaaagaata gaccgagata      3350
gggttgagtg ttgttccagt ttggaacaag agtccactat taaagaacgt      3400
ggactccaac gtcaaagggc gaaaaaccgt ctatcagggc gatggcccac      3450
tacgtgaacc atcaccctaa tcaagttttt tggggtcgag gtgccgtaaa      3500
gcactaaatc ggaaccctaa agggagcccc cgatttagag cttgacgggg      3550
aaagccggcg aacgtggcga gaaaggaagg gaagaaagcg aaaggagcgg      3600
gcgctagggc gctggcaagt gtagcggtca cgctgcgcgt aaccaccaca      3650
cccgccgcgc ttaatgcgcc gctacagggc gcgtcaggtg cacttttcg       3700
gggaaatgtg cgcggaaccc ctatttgttt attttctaa atacattcaa        3750
atatgtatcc gctcatgaga caataaccct gataaatgct tcaataatat      3800
tgaaaaagga agagtcctga ggcggaaaga accagctgtg gaatgtgtgt      3850
cagttagggt gtggaaagtc cccaggctcc ccagcaggca gaagtatgca      3900
aagcatgcat ctcaattagt cagcaaccag gtgtggaaag tccccaggct      3950
ccccagcagg cagaagtatg caaagcatgc atctcaatta gtcagcaacc      4000
atagtcccgc ccctaactcc gcccatcccg cccctaactc cgcccagttc      4050
cgcccattct ccgccccatg gctgactaat ttttttatt tatgcagagg       4100
ccgaggccgc ctcggcctct gagctattcc agaagtagtg aggaggcttt      4150
tttggaggcc tactagtcgg ccgtacgggc cctttcgtct cgcgcgtttc      4200
ggtgatgacg gtgaaaacct ctgacacatg cagctcccgg agacggtcac      4250
agcttgtctg taagcggatg ccgggagcag acaagcccgt cagggcgcgt      4300
cagcgggtgt tggcgggtgt cggggctggc ttaactatgc ggcatcagag      4350
cagattgtac tgagagtgca ccatatgcgg tgtgaaatac cgcacagatg      4400
cgtaaggaga aaataccgca tcaggcgcc ttaagggcct cgtgatacgc       4450
ctatttttat aggttaatgt catgataata atggtttctt agacgtcagg      4500
```

```
tggcactttt cggggaaatg tgcgcggaac ccctatttgt ttatttttct      4550
aaatacattc aaatatgtat ccgctcatga gacaataacc ctgataaatg      4600
cttcaataat attgaaaaag gaagagtatg agtattcaac atttccgtgt      4650
cgcccttatt ccctttttg cggcattttg ccttcctgtt tttgctcacc       4700
cagaaacgct ggtgaaagta aaagatgctg aagatcagtt gggtgcacga      4750
gtgggttaca tcgaactgga tctcaacagc ggtaagatcc ttgagagttt      4800
tcgccccgaa gaacgttttc caatgatgag cacttttaaa gttctgctat      4850
gtggcgcggt attatcccgt attgacgccg ggcaagagca actcggtcgc      4900
cgcatacact attctcagaa tgacttggtt gagtactcac cagtcacaga      4950
aaagcatctt acggatggca tgacagtaag agaattatgc agtgctgcca      5000
taaccatgag tgataacact gcggccaact tacttctgac aacgatcgga      5050
ggaccgaagg agctaaccgc ttttttgcac aacatggggg atcatgtaac      5100
tcgccttgat cgttgggaac cggagctgaa tgaagccata ccaaacgacg      5150
agcgtgacac cacgatgcct gtagcaatgg caacaacgtt gcgcaaacta      5200
ttaactggcg aactacttac tctagcttcc cggcaacaat taatagactg      5250
gatggaggcg gataaagttg caggaccact tctgcgctcg gcccttccgg      5300
ctggctggtt tattgctgat aaatctggag ccggtgagcg tgggtctcgc      5350
ggtatcattg cagcactggg gccagatggt aagccctccc gtatcgtagt      5400 tatctcacacg acggggagtc aggcaactat ggatgaacga atagacaga     5450 tcgctgagat aggtgcctca ctgattaagc attggtaact gtcagaccaa      5500
gtttactcat atatacttta gattgattta aaacttcatt tttaatttaa      5550
aaggatctag gtgaagatcc ttttgataa tctcatgacc aaaatccctt       5600
aacgtgagtt ttcgttccac tgagcgtcag accccgtaga aaagatcaaa      5650
ggatcttctt gagatccttt ttttctgcgc gtaatctgct gcttgcaaac      5700
aaaaaaacca ccgctaccag cggtggtttg tttgccggat caagagctac      5750
caactctttt tccgaaggta actggcttca gcagagcgca gataccaaat      5800
actgtccttc tagtgtagcc gtagttaggc caccacttca agaactctgt      5850
agcaccgcct acatacctcg ctctgctaat cctgttacca gtggctgctg      5900
ccagtggcga taagtcgtgt cttaccgggt tggactcaag acgatagtta      5950
ccggataagg cgcagcggtc gggctgaacg ggggggttcgt gcacacagcc     6000 cagcttggag cgaacgacct acaccgaact gagatacctta cagcgtgagc    6050 tatgagaaag cgccacgctt cccgaaggga gaaaggcgga caggtatccg      6100
gtaagcggca gggtcggaac aggagagcgc acgagggagc ttccaggggg      6150
aaacgcctgg tatctttata gtcctgtcgg gtttcgccac ctctgacttg      6200
agcgtcgatt tttgtgatgc tcgtcagggg gcggagccta tggaaaaac      6250 gccagcaacg cggccttttt acggttcctg gccttttgct ggccttttgc      6300
tcacatgttc tttcctgcgt tatcccctga ttctgtggat aaccgtatta      6350
ccgcctttga gtgagctgat accgctcgcc gcagccgaac gaccgagcgc      6400
agcgagtcag tgagcgagga agcggaag                              6428
```

<210> SEQ ID NO 4
<211> LENGTH: 7508
<212> TYPE: DNA
<213> ORGANISM: Artificial Sequence
<220> FEATURE:
<221> NAME/KEY: Unsure
<222> LOCATION:
<223> OTHER INFORMATION: Synthesized

<400> SEQUENCE: 4

| | | | | | |
|---|---|---|---|---|---|
| accaccgcgg | tggcggccgc | tccggagtgc | tcctaatgag | aagcagagtg | 50 |
| aagagtgatt | tatttatgga | ttacctagct | ggaacagccc | taatgcacag | 100 |
| tgtgagagtg | tgcatgagtg | tatgtgtgtg | tgtatgcgcg | cgcctgtgtg | 150 |
| tgtgttttac | ctctcttgga | gtcatgtcgc | tcagtaattg | ctgatgcaac | 200 |
| tctttgtcat | ccagggtttg | ccctctcctc | ctgtgaacct | atgggatgag | 250 |
| ttatattcat | cttggcttgt | ccctatagga | gagaggaagg | ggactgtaag | 300 |
| tgcgagtatg | tcaaaatgag | tgaaggtgaa | agtatatttg | tataatttta | 350 |
| tatttgaaag | tgttcatgtg | tagcagtgca | aaaaggttga | agatgaggtg | 400 |
| acaaagaaac | agaaaggtgg | agatggaaat | aagtaaagaa | agagggagtt | 450 |
| tgtgtgtgta | tgtgtgcgag | tgtgtgtaag | tgtgtgtgag | aaggcaggtg | 500 |
| ttagcatcca | ctcccatgct | gggaacagct | aggtttgaaa | ccgctccacc | 550 |
| tcattacctt | atgcagggaa | taatcatcat | cactatacac | aaaactcatc | 600 |
| aatataaatc | ttgcactgga | caagatccaa | aagcacttgc | agcttggtga | 650 |
| aagtatgggg | ctaatgatgt | ggtgaagcat | agggtgaaag | aacaaggaat | 700 |
| gcttttgcta | aacttctcca | ggaaggtcac | gttaaataag | aattaaacaa | 750 |
| taaagccaca | gttgaagagc | aacattatat | cacctctatg | tttttaaaca | 800 |
| tgtttgaccg | tttacaaaaa | tcaaacaaac | cactcccagt | tatcagagga | 850 |
| atagaactga | caccggaaga | acaatgaata | gtattaaaat | caatgaacca | 900 |
| gccaacatct | ggcacataag | ctcctttggc | agacgggggg | ctcaaacctg | 950 |
| acaatagttt | aaaatatcac | atacagagaa | gactagggaa | taataggacc | 1000 |
| ttgatgtggt | gggagcaagg | agtgagctct | ttactttgaa | gctaccttg | 1050 |
| tggagtcaca | attgcaaata | tcaatttcag | cagatgatct | atagtcttgt | 1100 |
| cacaaaaagg | tgtttcagat | taacctaacg | gctgtccatt | aggatgctgg | 1150 |
| tgcagcattt | gttcgcagct | aagacagtga | atttaaagtg | atttagatgg | 1200 |
| caaatgtaat | aacttaaaac | cataatttac | agttttacag | gcaagtgaaa | 1250 |
| taacatataa | attataattt | tgccaattat | acaaagctgt | agctacgtga | 1300 |
| agcaaaacag | gtgttcacta | gagctaggct | aatttctcat | gtctttatac | 1350 |
| aaatagtcaa | ggaaaacaac | acgaaacatc | aaaccaaacg | gatatataca | 1400 |
| tgaaacagca | caagcatacg | cataagcgta | tgagattcac | tttgtatcag | 1450 |
| cacacaaagg | aatcgtattt | tatatatacc | ttcatcagta | atgacgaaga | 1500 |
| atgtgaacaa | aaatgtcaaa | agcccacact | aactcagtgg | tcgtcaggag | 1550 |
| aagcctgctc | gagaaaagaa | tgcgatgatt | taaaaatcga | tgggcgttta | 1600 |
| aaatcaccc | aagcctctat | atgtccagga | attaaaatag | gtttctgtca | 1650 |
| tatgttgctc | ggtaaacgcc | ataataacac | actttccggt | tattcgttag | 1700 |

```
gaataagcat ctgagccttc acttggttgg cgctcgcgct tgagtcacat      1750
gttgcaacgt cacggcagta gttagttact gtagtcgcga ggaatgaagc      1800
cgtcatttca agctggagag ctctctcaat gcgcactaca ctgcgagcgc      1850
tcaccatgtc atccaactgc ttcaactcaa ctccaaagga tccgctcagt      1900
catgggagtc cattacctca accatgcaat ttccaccatc aataatttaa      1950
tctatttgct caaaagctga agagacaact tgcagctgct gcttggcgaa      2000
gagcggacga atatcgcaga atagttgcgc ggaggtctta tccaaaacat      2050
cccagatgac actgtcctgc tgaatggtct cctttacgac tggacagtac      2100
ccgggtaccg gtcgccacca tggtgcgctc ctccaagaac gtcatcaagg      2150
agttcatgcg cttcaaggtg cgcatggagg gcaccgtgaa cggccacgag      2200
ttcgagatcg agggcgaggg cgagggccgc ccctacgagg ccacaacac       2250 cgtgaagctg aaggtgacca agggcggccc cctgcccttc gcctgggaca      2300
tcctgtcccc ccagttccag tacggctcca aggtgtacgt gaagcacccc      2350
gccgacatcc ccgactacaa gaagctgtcc ttccccgagg gcttcaagtg      2400
ggagcgcgtg atgaacttcg aggacggcgg cgtggcgacc gtgacccagg      2450
actcctccct gcaggacggc tgcttcatct acaaggtgaa gttcatcggc      2500
gtgaacttcc cctccgacgg ccccgtgatg cagaagaaga ccatgggctg      2550
ggaggcctcc accgagcgcc tgtaccccg cgacggcgtg ctgaagggcg       2600
agatccacaa ggccctgaag ctgaaggacg gcggccacta cctggtggag      2650
ttcaagtcca tctacatggc caagaagccc gtgcagctgc ccggctacta      2700
ctacgtggac accaagctgg acatcacctc ccacaacgag gactacacca      2750
tcgtggagca gtacgagcgc accgagggcc gccaccacct gttcctgtag      2800
cggccgcgac tctagaattc ggccgcattg accattaaga ggggcagata      2850
gtgtacacaa tgtatagatt ttattgagag ttctaaaaaa agagagagag      2900
aaagagaaaa tatctatttg tatatacata acagggtaaa ttattcagtc      2950
agataaaaat tttatggact gcatgtaaaa aagaaaagt ttatacagta       3000 agtgatacta cagtctattt attgaacata ttcatgacct tgtaaacaat      3050
taaaaaaaga tctgatcagt catttgcgcc cagttcaaat tactatatca      3100
cattcctcaa gacattgtgt tttttacgtt gccaagattt tgagagatga      3150
ggagaggagg gggtgaggaa gaattacatt caagaaagaa aaaaaagaa       3200 aaaaaaaga aaaaacttgc atgctgcttc aattgtgaat tgaaaactg        3250 tccactttgg gaaacaagg aatcggtttc cgaccaaaac attccgttta       3300
cattctcaac cgtaacagga tttcctcctc tcagtactct gtctgtttac      3350
tatcctcaac ttctcaaggt aatgttggaa atacatacta tgtcaaggtg      3400
ctgttgtcaa agctttgctg tttattttt tatccccaca agatgaaaaa       3450
aaatatataa aatatatata tatataaaat ttattcattg acatgtgttc      3500
tggattaata taattcattt tgtatgttgt gaagttgttt gcaatattaa      3550
attgaaatat ttgaagaaat aaaattacta taggcaactg aaaaacaaaa      3600
ccaatgtcaa taaagtttga gctctccctt tacaggtcga aatttggcac      3650
```

| | |
|---|---|
| atgctgtgca gagaacatct tctctcgcag gcaaacatac tttggatcct | 3700 |
| acattcatat gatttcaaaa gggataatga tagatataag tatatacact | 3750 |
| acagtatata agtatttatt tcccatcctc tcaacatata tagttgaagt | 3800 |
| cagaattatt agcctccccc ctgtttcttt gttccccaat ttctgtttaa | 3850 |
| tagagagaag attttttttaa cacatttctg aacatattag ttttaataac | 3900 |
| taatacctga tttatttttat ctttgccatg atgcacagtaa ataatatttg | 3950 |
| acttgatatt tgtctagaca tttctttaca gcttaaagtg acatttaaag | 4000 |
| gcttaaccag gttaactagg caggttaggg taattaggca agttatttta | 4050 |
| taacaatggt ttgttctgta gactatcaac tatatagctt aaaggggata | 4100 |
| ataattttgt ccttaaatta ttattattttt tttttattaa aaactgcttt | 4150 |
| tattctagtc aaatcaaaat aaataagact ttctcctgaa gagaaaatat | 4200 |
| tatcaggcat actgtgaaaa tttccatgcc ctgttaaaca tcatttggta | 4250 |
| aatataaaaa gaataataat aaattaaagg ggggctaata gttctgactt | 4300 |
| caactgtatg tctatatccg tattaccaag ctaatgtgaa atctcaaagc | 4350 |
| cagaaatgca gacgaacaca tccatccaat gtaaattctg atgtgttctg | 4400 |
| tggaacaaca aacactctag aaagttctca ggtaagactt gatatgtaaa | 4450 |
| ttctatggaa accagtctct catgtaatgt tgtccagagg gagaaggcaa | 4500 |
| tcatcactag cactaagaga ttaggatttt cttttgtctg taggatagat | 4550 |
| caatgaagtc aacactccaa tgcactctgc gtgatatctg atacacctga | 4600 |
| acacagacac agacctatac acaaacctgc tttccttcaa aggttgttat | 4650 |
| cagacaactg aacagaaatc tgtctgacac tgatacactg ccacagataa | 4700 |
| gggaggagtt tcatctgttc atggtaagta tctctgcatc atgagacaca | 4750 |
| tgggcaggac cataaaggat gctcaggcgg aaagtcaaaa ctgattataa | 4800 |
| gtgcatcctt tatcagaaac acaactcaaa ttaaatttgt gtacccaagg | 4850 |
| atattgatat gaaagcataa taatagctat cagccttgct taatgagtaa | 4900 |
| gtgtttgctt aaccttatag gaacaaatat gaagctgcaa aatataaatc | 4950 |
| aatggtgact ggactagata aagaaatgga caataaaaca ttcttctggt | 5000 |
| gcattttatc tgagaaacaa cttgcattat ttttgtgagg atcagatttt | 5050 |
| ccccagttca aagtagtcct tggtaagacc cagcaggggc cgacgatcga | 5100 |
| cgcgtaaatt gtaagcgtta atattttgtt aaaattcgcg ttaaatttttt | 5150 |
| gttaaatcag ctcatttttt aaccaatagg ccgaaatcgg caaaatccct | 5200 |
| tataaatcaa aagaatagac cgagataggg ttgagtgttg ttccagtttg | 5250 |
| gaacaagagt ccactattaa agaacgtgga ctccaacgtc aaagggcgaa | 5300 |
| aaaccgtcta tcagggcgat ggccactac gtgaaccatc accctaatca | 5350 |
| agttttttgg ggtcgaggtg ccgtaaagca ctaaatcgga accctaaagg | 5400 |
| gagcccccga tttagagctt gacggggaaa gccggcgaac gtggcgagaa | 5450 |
| aggaagggaa gaaagcgaaa ggagcgggcg ctagggcgct ggcaagtgta | 5500 |
| gcggtcacgc tgcgcgtaac caccacaccc gccgcgctta atgcgccgct | 5550 |
| acagggcgcg tcaggtggca cttttcgggg aaatgtgcgc ggaacccta | 5600 |
| tttgtttatt tttctaaata cattcaaata tgtatccgct catgagacaa | 5650 |

```
taaccctgat aaatgcttca ataatattga aaaaggaaga atcctgaggc        5700
cgggccataa cttcgtataa tgtatgctat acgaagttat ccatgggccc        5750
cccctcgaca tgagtaaact tggtctgaca gttaccaatg cttaatcagt        5800
gaggcaccta tctcagcgat ctgtctattt cgttcatcca tagttgcctg        5850
actccccgtc gtgtagataa ctacgatacg ggagggctta ccatctggcc        5900
ccagtgctgc aatgataccg cgagacccac gctcaccggc tccagattta        5950
tcagcaataa accagccagc cggaagggcc gagcgcagaa gtggtcctgc        6000
aactttatcc gcctccatcc agtctattaa ttgttgccgg gaagctagag        6050
taagtagttc gccagttaat agtttgcgca acgttgttgc cattgctaca        6100
ggcatcgtgg tgtcacgctc gtcgtttggt atggcttcat tcagctccgg        6150
ttcccaacga tcaaggcgag ttacatgatc ccccatgttg tgcaaaaaag        6200
cggttagctc cttcggtcct ccgatcgttg tcagaagtaa gttggccgca        6250
gtgttatcac tcatggttat ggcagcactg cataattctc ttactgtcat        6300
gccatccgta agatgctttt ctgtgactgg tgagtactca accaagtcat        6350
tctgagaata gtgtatgcgg cgaccgagtt gctcttgccc ggcgtcaata        6400
cgggataata ccgcgccaca tagcagaact ttaaaagtgc tcatcattgg        6450
aaaacgttct cggggcgaaa actctcaag gatcttaccg ctgttgagat         6500
ccagttcgat gtaacccact cgtgcaccca actgatcttc agcatctttt        6550
actttcacca gcgtttctgg gtgagcaaaa acaggaaggc aaaatgccgc        6600
aaaaaaggga ataagggcga cacggaaatg ttgaatactc atactcttcc        6650
tcaggttact catatatact ttagattgat ttaaaacttc attttttaatt       6700
taaaaggatc taggtgaaga tcctttttga taatctcatg accaaaatcc        6750
cttaacgtga gttttcgttc cactgagcgt cagaccccgt agaaaagatc        6800
aaaggatctt cttgagatcc tttttttctg cgcgtaatct gctgcttgca        6850
aacaaaaaaa ccaccgctac cagcggtggt ttgtttgccg gatcaagagc        6900
taccaactct ttttccgaag gtaactggct tcagcagagc gcagatacca        6950
aatactgtcc ttctagtgta gccgtagtta ggccaccact tcaagaactc        7000
tgtagcaccg cctacatacc tcgctctgct aatcctgtta ccagtggctg        7050
ctgccagtgg cgataagtcg tgtcttaccg ggttggactc aagacgatag        7100
ttaccggata aggcgcagcg gtcgggctga acggggggtt cgtgcacaca        7150
gcccagcttg gagcgaacga cctacaccga actgagatac ctacagcgtg        7200
agctatgaga aagcgccacg cttcccgaag ggagaaaggc ggacaggtat        7250
ccggtaagcg gcagggtcgg aacaggagag cgcacgaggg agcttccagg        7300
gggaaacgcc tggtatcttt atagtcctgt cgggtttcgc cacctctgac        7350
ttgagcgtcg atttttgtga tgctcgtcag ggggcggag cctatggaaa         7400
aacgccagca acgcggcctt tttacggttc ctggccttt gctggccttt         7450
tgctcacatg ttctttcctg cgttatcccc tgattctgtg ataaccgta         7500
ttaccgcc                                                      7508
```

<210> SEQ ID NO 5

```
<211> LENGTH: 7495
<212> TYPE: DNA
<213> ORGANISM: Artificial Sequence
<220> FEATURE:
<221> NAME/KEY: Unsure
<222> LOCATION:
<223> OTHER INFORMATION: Synthesized

<400> SEQUENCE: 5
accaccgcgg tggcggccgc tccggagtgc tcctaatgag aagcagagtg         50
aagagtgatt tatttatgga ttacctagct ggaacagccc taatgcacag        100
tgtgagagtg tgcatgagtg tatgtgtgtg tgtatgcgcg cgcctgtgtg        150
tgtgttttac ctctcttgga gtcatgtcgc tcagtaattg ctgatgcaac        200
tctttgtcat ccagggtttg ccctctcctc ctgtgaacct atgggatgag        250
ttatattcat cttggcttgt ccctatagga gagaggaagg ggactgtaag        300
tgcgagtatg tcaaaatgag tgaaggtgaa agtatatttg tataatttta        350
tatttgaaag tgttcatgtg tagcagtgca aaaaggttga agatgaggtg        400
acaaagaaac agaaaggtgg agatggaaat aagtaaagaa agagggagtt        450
tgtgtgtgta tgtgtgcgag tgtgtgtaag tgtgtgtgag aaggcaggtg        500
ttagcatcca ctcccatgct gggaacagct aggtttgaaa ccgctccacc        550
tcattacctt atgcagggaa taatcatcat cactatacac aaaactcatc        600
aatataaatc ttgcactgga caagatccaa agcacttgc agcttggtga         650 aagtatgggg ctaatgatgt ggtgaagcat agggtgaaag aacaaggaat        700
gcttttgcta aacttctcca ggaaggtcac gttaaataag aattaaacaa        750
taaagccaca gttgaagagc aacattatat cacctctatg tttttaaaca        800
tgtttgaccg tttacaaaaa tcaaacaaac cactcccagt tatcagagga        850
atagaactga caccggaaga acaatgaata gtattaaaat caatgaacca        900
gccaacatct ggcacataag ctcctttggc agacggggggg ctcaaacctg       950 acaatagttt aaaatatcac atacagagaa gactagggaa taataggacc       1000
ttgatgtggt gggagcaagg agtgagctct ttactttgaa gctacctttg       1050
tggagtcaca attgcaaata tcaatttcag cagatgatct atagtcttgt       1100
cacaaaaagg tgtttcagat taacctaacg gctgtccatt aggatgctgg       1150
tgcagcattt gttcgcagct aagacagtga atttaaagtg atttagatgg       1200
caaatgtaat aacttaaaac cataatttac agttttacag gcaagtgaaa       1250
taacatataa attataattt tgccaattat acaaagctgt agctacgtga       1300
agcaaaacag gtgttcacta gagctaggct aatttctcat gtctttatac       1350
aaatagtcaa ggaaacaac acgaaacatc aaaccaaacg gatatataca        1400
tgaaacagca caagcatacg cataagcgta tgagattcac tttgtatcag       1450
cacacaaagg aatcgtattt tatatatacc ttcatcagta atgacgaaga       1500
atgtgaacaa aaatgtcaaa agcccacact aactcagtgg tcgtcaggag       1550
aagcctgctc gagaaaagaa tgcgatgatt taaaaatcga tgggcgttta       1600
aaatcacccc aagcctctat atgtccagga attaaaatag gtttctgtca       1650
tatgttgctc ggtaaacgcc ataataacac actttccggt tattcgttag       1700
gaataagcat ctgagccttc acttggttgg cgctcgcgct tgagtcacat       1750
```

-continued

| | |
|---|---|
| gttgcaacgt cacggcagta gttagttact gtagtcgcga ggaatgaagc | 1800 |
| cgtcatttca agctggagag ctctctcaat gcgcactaca ctgcgagcgc | 1850 |
| tcaccatgtc atccaactgc ttcaactcaa ctccaaagga tccgctcagt | 1900 |
| catgggagtc cattacctca accatgcaat ttccaccatc aataatttaa | 1950 |
| tctatttgct caaaagctga agagacaact tgcagctgct gcttggcgaa | 2000 |
| gagcggacga atatcgcaga atagttgcgc ggaggtctta tccaaaacat | 2050 |
| cccagatgac actgtcctgc tgaatggtct cctttacgac tggacagtac | 2100 |
| ccgggataat atggccacaa ccatggcctc ctccgagaac gtcatcaccg | 2150 |
| agttcatgcg cttcaaggtg cgcatggagg gcaccgtgaa cggccacgag | 2200 |
| ttcgagatcg agggcgaggg cgagggccgc ccctacgagg ccacaacac | 2250 |
| cgtgaagctg aaggtgacca agggcggccc cctgcccttc gcctgggaca | 2300 |
| tcctgtcccc ccagttccag tacggctcca aggtgtacgt gaagcacccc | 2350 |
| gccgacatcc ccgactacaa gaagctgtcc ttccccgagg gcttcaagtg | 2400 |
| ggagcgcgtg atgaacttcg aggacggcgg cgtggcgacc gtgacccagg | 2450 |
| actcctccct gcaggacggc tgcttcatct acaaggtgaa gttcatcggc | 2500 |
| gtgaacttcc cctccgacgg ccccgtgatg cagaagaaga ccatgggctg | 2550 |
| ggaggcctcc accgagcgcc tgtacccccg cgacggcgtg ctgaagggcg | 2600 |
| agacccacaa ggccctgaag ctgaaggacg gcggccacta cctggtggag | 2650 |
| ttcaagtcta tctacatggc caagaagccc gtgcagctgc ccggctacta | 2700 |
| ctacgtggac gccaagctgg acatcacctc ccacaacgag gactacacca | 2750 |
| tcgtggagca gtacgagcgc accgagggcc gccaccacct gttcctgtag | 2800 |
| cgaattcggc cgcattgacc attaagaggg gcagatagtg tacacaatgt | 2850 |
| atagatttta ttgagagttc taaaaaaaga gagagagaaa gagaaaatat | 2900 |
| ctatttgtat atacataaca gggtaaatta ttcagtcaga taaaaatttt | 2950 |
| atggactgca tgtaaaaaag aaaagtttta tacagtaagt gatactacag | 3000 |
| tctatttatt gaacatattc atgaccttgt aaacaattaa aaaagatct | 3050 |
| gatcagtcat ttgcgcccag ttcaaattac tatatcacat tcctcaagac | 3100 |
| attgtgtttt ttacgttgcc aagattttga gagatgagga gaggaggggg | 3150 |
| tgaggaagaa ttacattcaa gaaagaaaaa aaagaaaaa aaaagaaaa | 3200 |
| aacttgcatg ctgcttcaat tgtgaattga aaaactgtcc actttgggaa | 3250 |
| aacaaggaat cggtttccga ccaaaacatt ccgtttacat tctcaaccgt | 3300 |
| aacaggattt cctcctctca gtactctgtc tgtttactat cctcaacttc | 3350 |
| tcaaggtaat gttggaaata catactatgt caaggtgctg ttgtcaaagc | 3400 |
| tttgctgttt atttttttat ccccacaaga tgaaaaaaaa tatataaaat | 3450 |
| atatatatat ataaaattta ttcattgaca tgtgttctgg attaatataa | 3500 |
| ttcattttgt atgttgtgaa gttgtttgca atattaaatt gaatatttg | 3550 |
| aagaaataaa attactatag gcaactgaaa acaaaacca atgtcaataa | 3600 |
| agtttgagct ctccctttac aggtcgaaat ttggcacatg ctgtgcagag | 3650 |
| aacatcttct ctcgcaggca aacatacttt ggatcctaca ttcatatgat | 3700 |

```
ttcaaaaggg ataatgatag atataagtat atacactaca gtatataagt         3750
atttatttcc catcctctca acatatatag ttgaagtcag aattattagc         3800
ctcccccctg tttctttgtt ccccaatttc tgtttaatag agagaagatt         3850
tttttaacac atttctgaac atattagttt taataactaa tacctgattt         3900
attttatctt tgccatgatg acagtaaata atatttgact tgatatttgt         3950
ctagacattt ctttacagct taaagtgaca tttaaaggct taaccaggtt         4000
aactaggcag gttagggtaa ttaggcaagt tattttataa caatggtttg         4050
ttctgtagac tatcaactat atagcttaaa ggggataata attttgtcct         4100
taaattatta ttattttttt ttattaaaaa ctgcttttat tctagtcaaa         4150
tcaaaataaa taagactttc tcctgaagag aaaatattat caggcatact         4200
gtgaaaattt ccatgccctg ttaaacatca tttggtaaat ataaaagaa          4250 taataataaa ttaaggggg gctaatagtt ctgacttcaa ctgtatgtct          4300
atatccgtat taccaagcta atgtgaaatc tcaaagccag aaatgcagac         4350
gaacacatcc atccaatgta aattctgatg tgttctgtgg aacaacaaac         4400
actctagaaa gttctcaggt aagacttgat atgtaaattc tatggaaacc         4450
agtctctcat gtaatgttgt ccagaggag aaggcaatca tcactagcac          4500
taagagatta ggattttctt ttgtctgtag gatagatcaa tgaagtcaac         4550
actccaatgc actctgcgtg atatctgata cacctgaaca cagacacaga         4600
cctatacaca aacctgcttt ccttcaaagg ttgttatcag acaactgaac         4650
agaaatctgt ctgacactga tacactgcca cagataaggg aggagtttca         4700
tctgttcatg gtaagtatct ctgcatcatg agacacatgg gcaggaccat         4750
aaaggatgct caggcggaaa gtcaaaactg attataagtg catcctttat         4800
cagaaacaca actcaaatta aatttgtgta cccaaggata ttgatatgaa         4850
agcataataa tagctatcag ccttgcttaa tgagtaagtg tttgcttaac         4900
cttataggaa caaatatgaa gctgcaaaat ataaatcaat ggtgactgga         4950
ctagataaag aaatggacaa taaaacattc ttctggtgca ttttatctga         5000
gaaacaactt gcattatttt tgtgaggatc agattttccc cagttcaaag         5050
tagtccttgg taagacccag caggggtcga cgatcgacgc gtaaattgta         5100
agcgttaata ttttgttaaa attcgcgtta aattttttgtt aaatcagctc        5150 atttttttaac caataggccg aaatcggcaa aatcccttat aaatcaaaag        5200
aatagaccga gatagggttg agtgttgttc cagtttggaa caagagtcca         5250
ctattaaaga acgtggactc caacgtcaaa gggcgaaaaa ccgtctatca         5300
gggcgatggc ccactacgtg aaccatcacc ctaatcaagt ttttggggt          5350 cgaggtgccg taaagcacta atcggaacc ctaaagggag ccccccgattt         5400 agagcttgac ggggaaagcc ggcgaacgtg gcgagaaagg aagggaagaa         5450
agcgaaagga gcgggcgcta gggcgctggc aagtgtagcg gtcacgctgc         5500
gcgtaaccac cacacccgcc gcgcttaatg cgccgctaca gggcgcgtca         5550
ggtggcactt ttcggggaaa tgtgcgcgga accctatttt gtttattttt         5600
ctaaatacat tcaaatatgt atccgctcat gagacaataa ccctgataaa         5650
tgcttcaata atattgaaaa aggaagaatc ctgaggccgg gccataactt         5700
```

```
cgtataatgt atgctatacg aagttatcca tgggccccc ctcgacatga        5750
gtaaacttgg tctgacagtt accaatgctt aatcagtgag gcacctatct       5800
cagcgatctg tctatttcgt tcatccatag ttgcctgact ccccgtcgtg       5850
tagataacta cgatacggga gggcttacca tctggcccca gtgctgcaat       5900
gataccgcga gacccacgct caccggctcc agatttatca gcaataaacc       5950
agccagccgg aagggccgag cgcagaagtg gtcctgcaac tttatccgcc       6000
tccatccagt ctattaattg ttgccgggaa gctagagtaa gtagttcgcc       6050
agttaatagt ttgcgcaacg ttgttgccat tgctacaggc atcgtggtgt       6100
cacgctcgtc gtttggtatg gcttcattca gctccggttc ccaacgatca       6150
aggcgagtta catgatcccc catgttgtgc aaaaaagcgg ttagctcctt       6200
cggtcctccg atcgttgtca gaagtaagtt ggccgcagtg ttatcactca       6250
tggttatggc agcactgcat aattctctta ctgtcatgcc atccgtaaga       6300
tgcttttctg tgactggtga gtactcaacc aagtcattct gagaatagtg       6350
tatgcggcga ccgagttgct cttgcccggc gtcaatacgg gataataccg       6400
cgccacatag cagaacttta aaagtgctca tcattggaaa acgttcttcg       6450
gggcgaaaac tctcaaggat cttaccgctg ttgagatcca gttcgatgta       6500
acccactcgt gcacccaact gatcttcagc atcttttact ttcaccagcg       6550
tttctgggtg agcaaaaaca ggaaggcaaa atgccgcaaa aaagggaata       6600
agggcgacac ggaaatgttg aatactcata ctcttcctca ggttactcat       6650
atatacttta gattgattta aaacttcatt tttaatttaa aaggatctag       6700
gtgaagatcc ttttttgataa tctcatgacc aaaatccctt aacgtgagtt       6750
ttcgttccac tgagcgtcag accccgtaga aaagatcaaa ggatcttctt       6800
gagatccttt ttttctgcgc gtaatctgct gcttgcaaac aaaaaaacca       6850
ccgctaccag cggtggtttg tttgccggat caagagctac caactctttt       6900
tccgaaggta actggcttca gcagagcgca gataccaaat actgtccttc       6950
tagtgtagcc gtagttaggc caccacttca agaactctgt agcaccgcct       7000
acatacctcg ctctgctaat cctgttacca gtggctgctg ccagtggcga       7050
taagtcgtgt cttaccgggt tggactcaag acgatagtta ccggataagg       7100
cgcagcggtc gggctgaacg gggggttcgt gcacacagcc cagcttggag       7150
cgaacgacct acaccgaact gagatacta cagcgtgagc tatgagaaag       7200
cgccacgctt cccgaaggga gaaaggcgga caggtatccg gtaagcggca       7250
gggtcggaac aggagagcgc acgagggagc ttccagggg aaacgcctgg       7300
tatctttata gtcctgtcgg gtttcgccac ctctgacttg agcgtcgatt       7350
tttgtgatgc tcgtcagggg ggcggagcct atggaaaaac gccagcaacg       7400
cggccttttt acggttcctg gccttttgct ggccttttgc tcacatgttc       7450
tttcctgcgt tatcccctga ttctgtggat aaccgtatta ccgcc          7495
```

TRANSGENIC SCREEN AND METHOD FOR SCREENING MODULATORS OF BRAIN-DERIVED NEUROTROPHIC FACTOR (BDNF) PRODUCTION

CROSS-REFERENCE TO RELATED APPLICATIONS

This is a continuation-in-part of application Ser. No. 10/306,737, filed Nov. 29, 2002, now U.S. Pat. No. 7,491,810, which claims priority on prior U.S. Provisional Application Ser. No. 60/334,079, filed Nov. 30, 2001, both of which are incorporated herein in their entirety by reference.

REFERENCE TO SEQUENCE LISTING

The present application incorporates by reference a file named: US 1353-03 Heinrich Sequence Listing, including SEQ ID NO.: 1, SEQ ID NO.: 2, SEQ ID NO.: 3, SEQ ID NO.: 4 and SEQ ID NO.: 5, provided herewith in a computer readable form—on a diskette, created on Dec. 22, 2003 and containing 32,891 bytes. The sequence listing information recorded on the diskette is identical to the written (on paper) sequence listing provided herein.

BACKGROUND OF THE INVENTION

The present invention is generally directed to screening of genes or modulators, and more particularly to a transgenic screen for screening biological and chemical test substances for their ability to influence or modulate the production of BDNF in cells.

Brain-derived neurotrophic factor (BDNF) belongs to a group of nerve growth factors called neurotrophins (NT). The function of NTs includes fostering the growth and survival of neurons during development. In adult brains, NTs have an influence on neuronal excitability and, specifically, BDNF appears to regulate neuronal morphology and synaptogenesis. It is also known to exhibit neuroprotective effects in a range of central nervous system areas (Binder et al. 2001). BDNF has been shown to enhance motor neuron survival in several experimental animal models (Department of Neurology, Baylor College of Medicine 2001). Neurodegenerative diseases, such as Huntington's Disease, Parkinson's Disease and Alzheimer's Disease are expected to show abnormal BDNF expression. Enhancement of BDNF function is thought to be one of the mechanisms by which anti-depressants work (Russo-Neustadt et al. 2001) and, as such, might have a significant effect in treating depression.

It is believed that raising the level of BDNF production in the cells would be an effective method of treating various neurodegenerative disease conditions. The current screens for substances that modulate BDNF production are based on cell culturing. Therefore, the screens measure the level of BDNF that is secreted into the culture media and measure changes to this level caused by modulators. However, the screens do not measure the change that the modulating substances effect at the transcription level, and may therefore not be as specific in identifying the action of a modulator.

Other work has also linked the BDNF gene promoter to a fluorescent reporter gene that allows screening for agents which affect the reporter gene expression by affecting the BDNF promoter. One such method was in vitro, involving the culture of a transgenic cell line.

A second existing method involves transgenic mice expressing BDNF promoters linked to a reporter gene. Once again, these mice are able to give a readout on substances that modulate gene expression by affecting the BDNF promoter. However, the mice need to be sacrificed to measure the effect of the modulator, or at least a cell culture must be taken. In either case, the advantages of multiple series of dynamic screens on the same test stock are lost.

The conventional screens, methods, or in vitro tests measure BDNF production directly and do not identify the specific transcription mechanism by which production is increased. BDNF expression is the result of a complex process, however, with a number of regulatory ("promoter" or "cis-") genes regulating the transcription of the neurotrophic factor. The present invention allows screening for the expression of specific genetic segments, to allow researchers to identify factors that affect the activity of specific promoter genes.

OBJECTS AND SUMMARY OF THE INVENTION

The principal object of the present invention is to provide an isolated BDNF gene promoter.

An object of the present invention is to provide a nucleic acid construct.

Another object of the present invention is to provide a nucleic acid construct including a BDNF gene promoter and a fluorescent marker tag.

Yet another object of the present invention is to provide a zebrafish gene construct.

Still yet another object of the present invention is to provide a transgenic zebrafish line capable of expressing BDNF gene promoter.

Still yet another object of the present invention is to provide a cloned zebrafish genomic sequence.

Still yet another object of the present invention is to provide a cloned zebrafish genomic sequence which includes the 5' UT (untranslated) region of zebrafish BDNF cDNA with its associated promoter.

Still yet another object of the present invention is to provide a transgenic screen for in vivo screening of various biological, inorganic, and organic substances for their ability to modulate the production of BDNF at the transcription level of the BDNF gene in a living organism. The screen includes a zebrafish (*Danio rerio*) BDNF promoter sequence inserted upstream of a fluorescent marker gene so that the BDNF promoter is marked by fluorescence.

An additional object of the present invention is to provide a transgenic screen which can be used to identify gene targets for drugs for neurodegenerative diseases or to identify biological and chemical substances that directly upregulate BDNF promoters and may therefore have a therapeutic effect on neurodegenerative diseases. Since such substances may also have a neuroprotective effect on patients receiving chemotherapy, the indication thereof would be greatly useful and commercially desirable.

Yet an additional object of the present invention is to provide a transgenic screen which could be formatted for a high throughput screen (HTS).

A further object of the present invention is to provide a method of screening various biological and chemical substances or molecules for their capability to regulate BDNF production in a living organism.

Yet a further object of the present invention is to provide a method of screening various biological and chemical substances for regulation of BDNF production, which does not require cell cultures. Therefore, the effect of potential modulators or substances can be tested on multiple cell and tissue types. The BDNF gene transcription can be measured repeatedly, dynamically, serially, and in multiple screens in individual or groups of living embryos and larvae.

In summary, the main object of the present invention is to provide a transgenic screen and method for screening biological and chemical test substances or molecules for their ability to influence or modulate the production of BDNF in cells, which includes a fusion gene having a zebrafish BDNF gene fragment (promoter) and a fluorescent marker gene inserted downstream of the BDNF gene fragment. When the fusion gene is injected into a zebrafish embryo, the BDNF promoter causes the production of fluorescent protein in various cell types. The embryo is exposed to a test substance for determining the effect thereof on the production of the fluorescent marker protein.

BRIEF DESCRIPTION OF THE DRAWINGS

The above and other objects, novel features and advantages of the present invention will become apparent from the following detailed description of the invention, as illustrated in the drawings, in which:

FIGS. 5A-B illustrate transcription factor recognition sites in the promoter region for promoter 1c (SEQ ID NO: 1);

FIGS. 7A-E illustrate a nucleic acid sequence of a construct made in accordance with the present invention (SEQ ID NO: 3);

FIGS. 8A-B illustrate a nucleic acid sequence of FIGS. 5A-B without transcription factor recognition sites (SEQ ID NO: 1);

FIGS. 9A-B illustrate another nucleic acid sequence of the promoter region for promoter 1c (SEQ ID NO: 2);

FIGS. 10A-F illustrate a nucleic acid sequence of a second embodiment of a construct made in accordance with the present invention (SEQ ID NO: 4); and FIGS. 11A-F illustrate a nucleic acid sequence of a third embodiment of a construct made in accordance with the present invention (SEQ ID NO: 5).

DETAILED DESCRIPTION OF THE INVENTION

Figure 1:
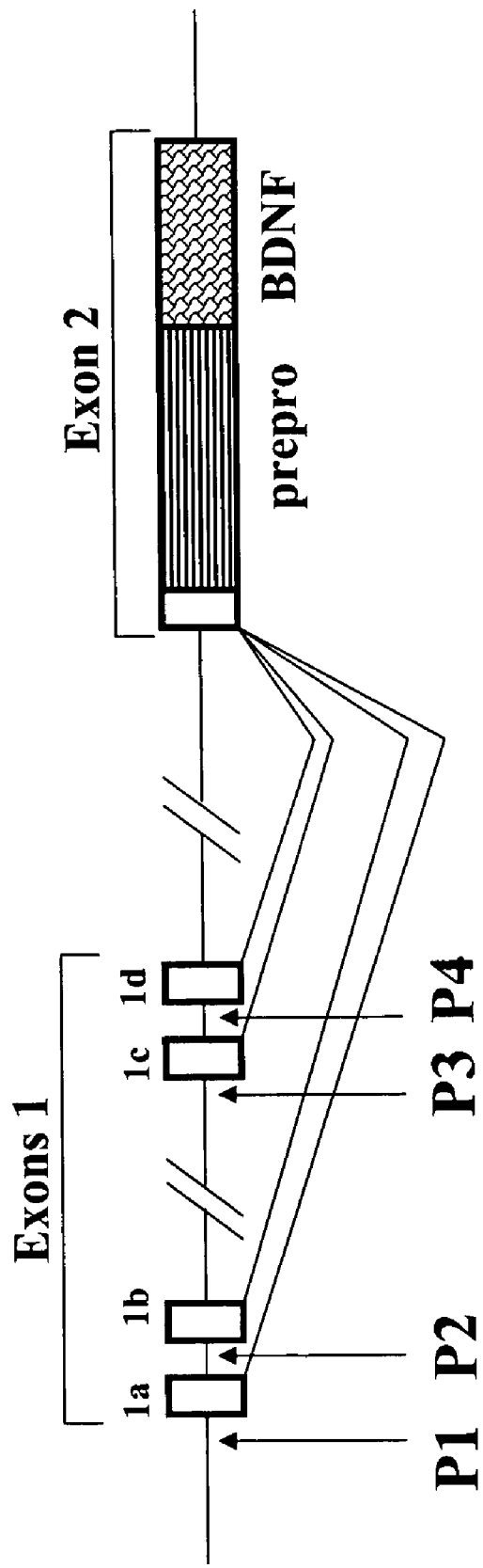
FIG. 1 illustrates organization of the mammalian BDNF gene.

The present invention illustrates a cloned zebrafish gene construct and a method of using the same in screening various biological and chemical substances or molecules for their capability to modulate the production of BDNF at the transcription level of the BDNF gene in a living organism.

Zebrafish are useful experimental organisms: small, about 3 cm long, the females can lay hundreds of eggs at weekly intervals. Since fertilization is external, the embryos can be manipulated easily as they are transparent, and examination can be made under the microscope (Wixon 2000). Mutagenesis screens are also easily achieved in the zebrafish, and large-scale projects of this nature have led to the production of huge numbers of mutant lines. Such populations can be useful in identifying genes that interact with the BDNF promoter and are consequently additional targets for modulating BDNF transcription (Huynh and Heinrich 2001).

Transgenic fish lines have been principally used within general scientific research in the analysis of promoter activity through reporter gene expression to identify cis-acting regulatory elements—i.e., the controlling effects of a regulatory gene on a structural gene (Dodd et al. 2000).

BDNF is a member of the neurotrophin family that also includes NGF (Levi-Montalcini, R. 1998, Levi-Montalcini, R. et al. 1995), NT-3 (Maisonpierre, P. C. et al. 1990, Maisonpierre, P. C. et al. 1991), NT-4/5 (Ip, N.Y. et al. 1992), NT-6 (Gotz, R. et al. 1994) and NT-7 (Nilsson, A. S. et al. 1998). BDNF is essential for the development and differentiation of specific sets of peripheral and central neuron in mammals (Alderson, R. F. et al. 1990, Hyman, C. et al. 1991, Johnson, J. E. et al. 1986, Sendtner, M. et al. 1992) and birds (Biffo, S. et al. 1994, Davies, A. M. et al. 1986, Frade, J. M. et al. 1997, Herzog, K. H. et al. 1994, Rodriguez-Tebar, A. and Barde, Y. A. 1988, Rodriguez-Tebar, A. et al. 1989). Like mammals and birds, the fishes possess a unique BDNF gene. Neither the structure nor the function of the fish BDNF gene are presently known.

To prepare tools for the molecular and cellular analysis of BDNF gene structure and function in the fish we used a recently cloned a zebrafish cDNA (Hashimoto, M. and Heinrich, G. 1997). Using the cDNA as a probe, we examined expression of BDNF mRNA in the developing zebrafish embryo and 4 day old larva. We extended this analysis to the earliest stages of embryonic development (Lum and Heinrich, 2001). These analyses showed that, in contrast to mammals, in the zebrafish, BDNF and BDNF mRNA are present in the zygote, and thus, may have a role in stages of development that precede nervous system formation. In the four day old larva BDNF and BDNF mRNA are expressed in specific cells within muscle, heart, neuromast, ear, brain, and cartilage.

Here we report on the cloning and structural analysis of the zebrafish BDNF gene. We show that its intron/exon organization is similar to that of the mammalian BDNF gene. Our genomic clones include the 5' untranslated region of the previously cloned BDNF cDNA and its associated promoter. When linked to an enhanced green fluorescent protein (EGFP-F) reporter and injected into Zebrafish embryos, this promoter mediates expression in cell types that express the endogenous BDNF gene. Transgenic lines derived from these embryos will allow us to utilize mutagenesis to identify genes that regulate BDNF gene expression.

Materials and Methods

Genomic Library Screening

A genomic PAC (P1 Artificial Chromosome) library was screened by colony hybridization. The library had been constructed from erythrocyte genomic DNA by C. T. Amemiya. The genomic DNA was partially digested with MboI and ligated into the pCYPAC6 (PAC) vector. Colonies were microarrayed onto nylon filters by the Resource Center of the German Genome Project (Vente, A. et al. 1999, Zehetner, G. and Lehrach, H. 1994). Each 9×9 inch filter contains approximately 24,000 clones (12,000 uniques plus 1 set of duplicates). 4 filters were provided by RZPD GmbH and screened with a mixture of two digoxigenin-labeled BDNF probes. The probes were prepared and labeled by PCR in the presence of digoxigenin-11-dUTP using a previously cloned zBDNF cDNA as template. Probe1 was directed exclusively to the coding exon (exon 2, FIG. 1) and probe2 mainly to the 5' untranslated region which has sequence similarity to exon 1c of the rat BDNF gene (FIG. 1). The following oligonucleotides were used for PCR. Probe1: sense 5'-acaggttagaagagt-gat-3' and antisense 5'-cttaatggtcaatgtgca-3'. Probe2: sense: 5'-gctcagtcatgggagtcc-3' and antisense 5'-atgaacgaacaggatg-gtcat-3'.

FIG. 1 illustrates organization of the mammalian BDNF gene. Boxes designate exons, and lines introns and flanking regions. Open boxes represent 5' untranslated regions. The arrows indicate the positions of the four promoters which are labeled P1-4. The first 4 exons are alternatively spliced to exon 2 such that BDNF mRNA always includes two exons and always contains exon 2. The first four exons are accordingly labeled 1a-d. The striped box is the translated region of exon 2 that encodes the entire BDNF precursor. The scaly box represents the 3' untranslated region.

Mapping and Sequencing of Genomic Subclones

Figure 2A:
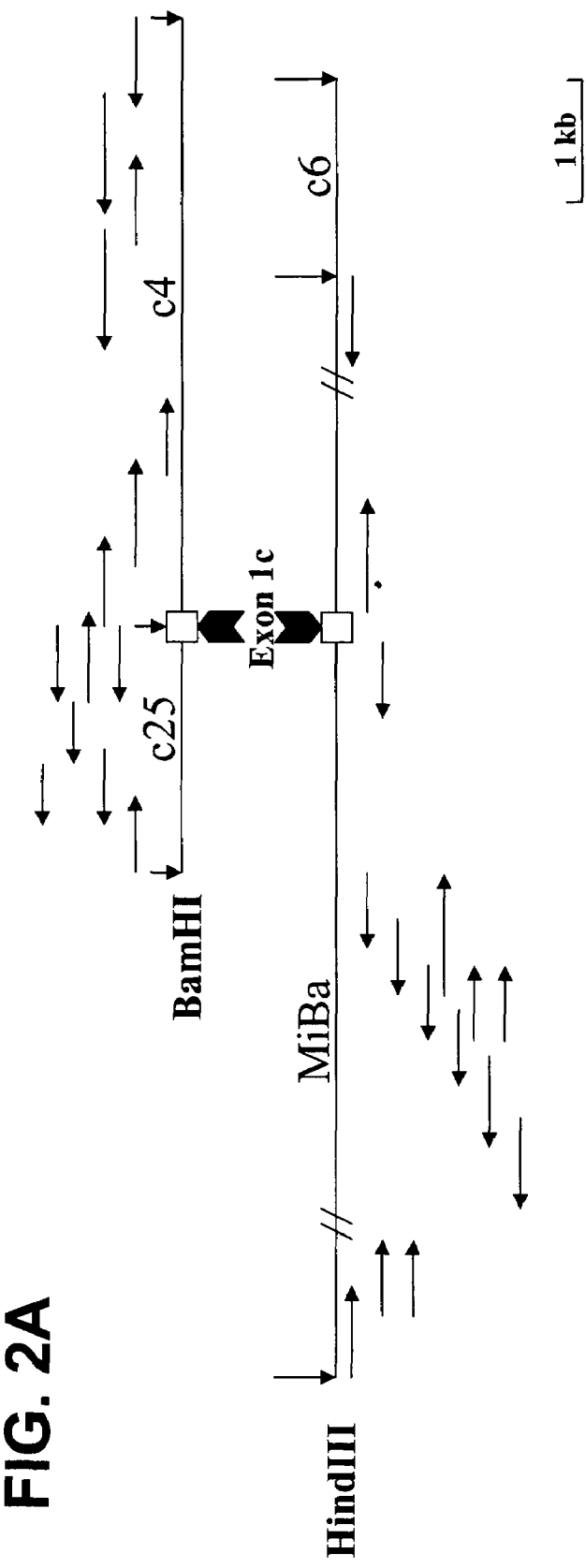
FIGS. 2A-B illustrate zebrafish BDNF gene BamHI and HindIII subclones and sequencing strategy.
Figure 2B:
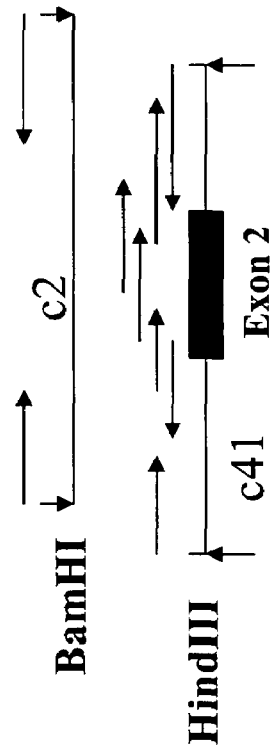

Standard restriction enzyme and Southern blot analyses were applied. Sequencing was contracted out to Davis Sequencing. DNA sequencing at the company is performed using ABI Prism 377 DNA sequencers with the 96-lane upgrade. Southern blots were probed with digoxigenin-labeled probes 1 and 2. A third probe (probe3) was used to identify the BamHI subclone encoding the 5' end of exon 1c (FIG. 2A). FIG. 2B shows the subclones (c2 and c41) that contain the coding exon 2. The following oligonucleotides were used to prepare probe3: sense 5'-ctcaatgcgcactac-3' and antisense 5'-ggatccttggagttgag-3'.

FIGS. 2A-B illustrate zebrafish BDNF gene BamHI and HindIII subclones and sequencing strategy. Vertical arrows mark restriction sites. Horizontal arrows indicate the origin, length and direction of sequencing reactions.

FIG. 2A shows the subclones that contain exon 1c (c4, c25, and MiBa). It is noted that exon 1c has a BamHI site. The promoter and 5' flank are located in c25. The 3' end of exon 1c and the 5' end of intron 1c are in c4. The sequencing gaps in MiBa are indicated by pairs of slashes. The empty box represents exon 1 c. The vertical block arrows point to exon 1c.

FIG. 2B shows the subclones (c2 and c41) that contain the coding exon 2. The black box designates exon 2.

Construction of Fusion Genes

Starting materials were the genomic subclones and a plasmid carrying EGFP-F (PEGFP-F from Clontech, Palo Alto, Calif.). EGFP-F is a derivative of GFP (green fluorescent protein) with enhanced fluorescence and a farnesylation signal at the COOH-terminal derived from the src protein, which anchors EGFP in the cell membrane. Standard methods of restriction enzyme digestion and ligation of selected fragments were applied. Junctions of heterologous fragments were sequenced to confirm correct construction of fusion genes.

Preparation of DNA and Microinjection of Embryos

Plasmids were digested with HindIII and StuI or MluI. The desired restriction fragments were purified by agarose gel electrophoresis. DNA was dissolved in 100 mM KCl at a concentration of 10-50 μg/ml. Phenol red was added to visualize injected DNA solution. DNA was injected into a blastomere or into the cytoplasmic stream below the blastomere(s) at the 2-8 cell stages. Embryos were enzymatically dechorionated with Pronase and extensively washed in embryo medium prior to injection Embryo medium=13 mM NaCl; 4.2 mM NaHCO3; 0.54 mM KCl; 0.025 mM Na2HPO4; 0.044 mM KH2PO4; 1.3 mM CaCl2; 1 mM MgSO4). Embryos were injected and maintained for 14 hpf on a bed of 0.7% agarose in embryo medium. Subsequently, they were placed into deionized water in clear plastic dishes for observation with a Zeiss IM fluorescent microscope or further growth.

Immunocytochemistry

Four (4) days old larvae were fixed in 4% paraformaldehyde. Whole mount embryos were stained with monoclonal Ab C-9 (Santa Cruz Biotech., Santa Cruz, Calif.), raised against a synthetic peptide representing the N-terminal 27 amino acids of human BDNF. Specifically bound Ab was visualized using the ABC system.

In Situ Hybridization

Twenty-four (24) hrs old larvae were fixed in 4% paraformaldehyde. Whole mount embryos were hybridized with a digoxigenin-labeled PCR-generated probe targeted to exon 2 (probe1). Specifically bound probe was visualized with anti-digoxigenin-Fab conjugated to alkaline phosphatase.

Results

Screening of PAC Library

Four (4) 4 filters obtained from the RZPD GmbH (www.rz-pd.de) were screened. Each filter contained 12 000 unique clones and 12 000 duplicates. A mixture of two digoxigenin-labeled probes was used. Probe 1 was directed toward the untranslated region of the previously cloned BDNF cDNA, and probe 2 to the coding exon. Two of the 48,000 clones screened hybridized to the mixture. They were named c206 and c241.

Restriction Enzyme and Southern Blot Hybridization Analysis

Figure 3:
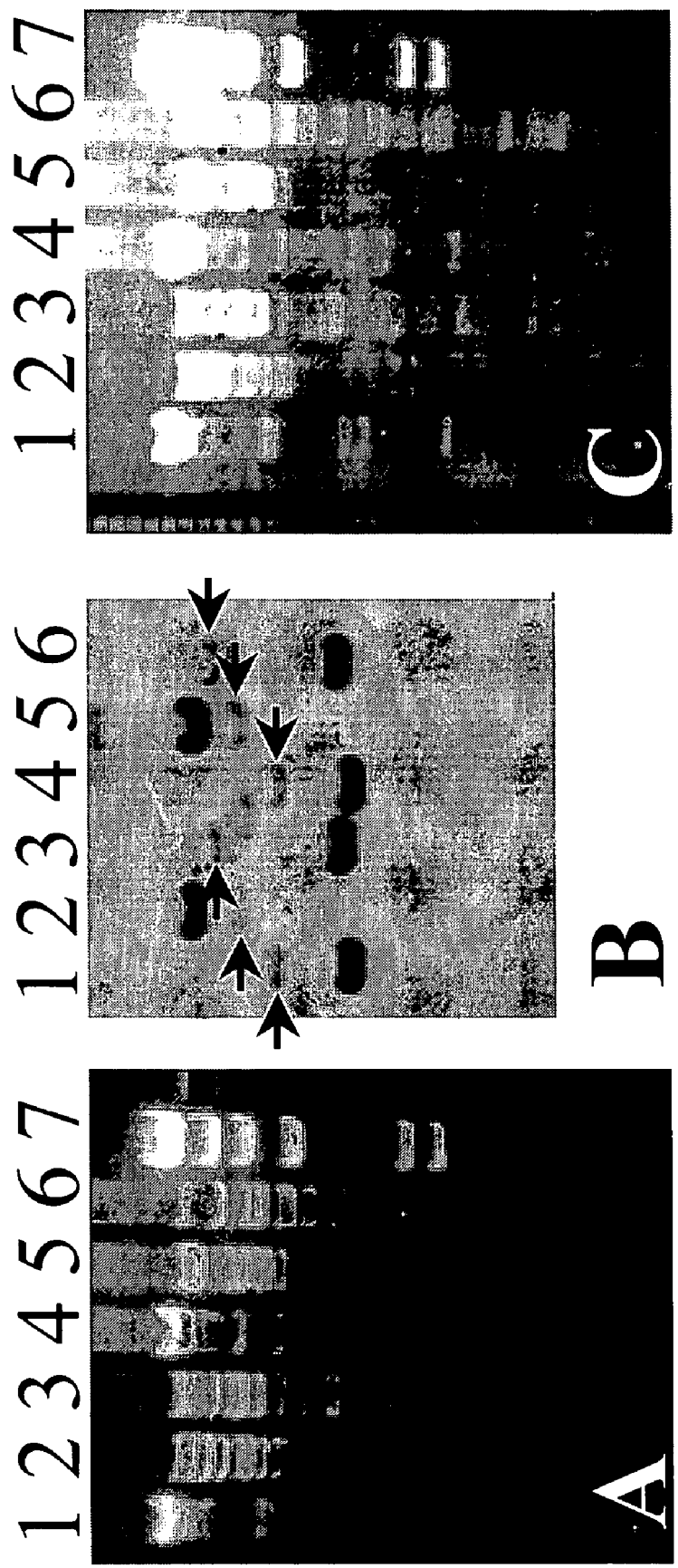
FIG. 3 illustrates restriction digest and southern blot hybridization analyses of genomic clones c206 and 241.

FIG. 3 illustrates restriction digest and southern blot hybridization analyses of genomic clones c206 and 241. Plasmid DNA was cut with various restriction enzymes and the digests were subjected to agarose gel electrophoresis in the presence of ethidium bromide. The gel was photographed and the DNA transferred to a nylon membrane. The membrane was probed sequentially with probe1 and probe2. Hybridized probe was visualized with an anti-digoxigenin FAb fragment conjugated to alkaline phosphatase and a chemiluminescent substrate. Panel A is underexposed to show the size marker (HindIII digest of Phage-lambda (lanes 7). Panel C is overexposed to show the smaller restriction fragments. Panel B shows the chemiluminogram. In all panels lanes 1-3 are c206 and lanes 4-6 c241. The DNA was digested with BamHI (lanes 1), HindIII (lanes 2) and EcoRI (lanes 3). The heavy bands in panel B represent hybridization with probe2. The light bands, marked with arrows, represent hybridization to probe1. It is noted that probe2 extends a short distance into exon 2 and therefore weakly hybridizes with DNA fragments containing exon 2.

The corresponding bacterial cultures were also obtained from the RZPD GmbH. Plasmid DNA was extracted from mini-cultures and analyzed by restriction enzyme digestion and southern blotting. The insert lengths were estimated from these digests as 100 kb for c206 and 80 kb for c241. FIG. 3 shows that there are restriction fragments that occur in both clones as well as those that are unique. The unique fragments add up to approximately 10 kb in c206 and 25 kb for c241. The overlap is therefore approximately 65-70 kb.

Probe1 and probe2 hybridized to fragments that are common to both genomic clones supporting the conclusion that the genomic clones are authentic. On the other hand, probe1 and probe2 hybridized to different fragments in all three restriction enzyme digests in both clones, suggesting the 5'

UT and coding exons are separated by a considerable distance. It is noted that probe2 overlaps to a small extent with exon 2 and, therefore, hybridizes weakly to the fragments recognized by probe1.

These analyses show that each of the two independent clones contains a complete transcription unit. Since the overlap is about 65 kb the transcription must be 65 kb or less. The human BDNF gene was found to be co-localized with 3 other genes on a 120 kb DNA fragment on chromosome 11p14 (Guillemot, F. et al. 1999).

Subcloning and Sequencing

The genomic clones c206 and c241 were digested with HindIII or BamHI and the mixture of fragments subcloned into the HindIII or BamHI sites of pEGFP-1 (Clontech). Non-fluorescent colonies were collected and screened by dot blot hybridization for subclones hybridizing to probe1, probe2, or probe3. One HindIII subclone hybridized to both probe2 and probe3. This clone was called MiBa. Another HindIII subclone hybridized to probe1, and was called c41. Three BamHI subclones hybridized to probe1, 2 or 3. They were called c2, c25, and c4, respectively. These clones were partially sequenced. (See FIGS. 2A-B for the sequencing strategies and portions that were sequenced.) The nucleotide sequences confirmed that we had cloned the zebrafish BDNF gene.

MiBa contains a 9 kb insert. c25 is completely embedded in MiBa. c4 overlaps with the 3' end of MiBa and contains an adjacent downstream 1.4 kb HindIII fragment. c41 and c2 contain 3 kb inserts and extensively overlap such that c2 extends only 250 bps farther 3' than c41. These mapping data are summarized in FIGS. 2A-B.

We have not yet mapped the relative positions of the HindIII or BamHI fragments that contain exon 1c and exon 2. Therefore, the size of intron 1c is not yet known.

RFLP

Figure 4:
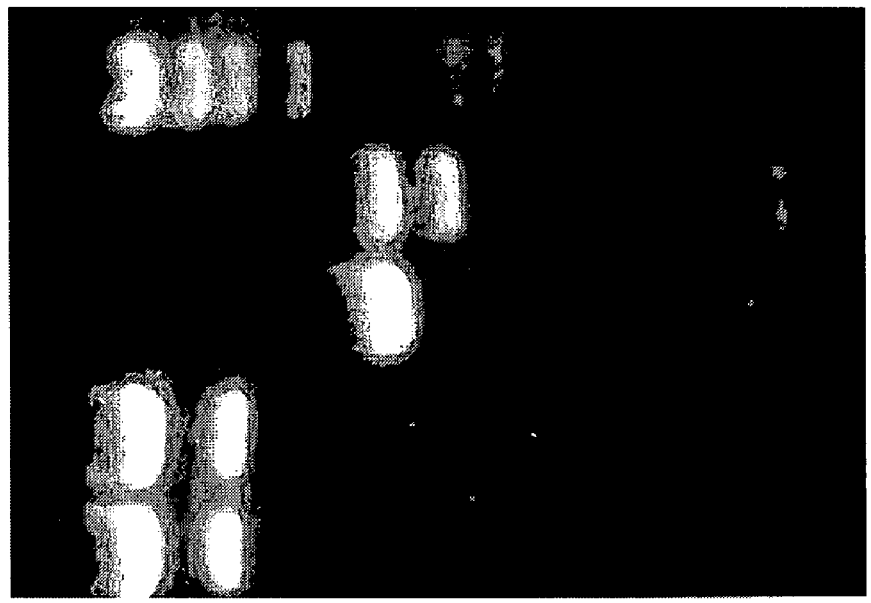
FIG. 4 illustrates apal RFLP in BDNF gene coding exon.

FIG. 4 illustrates apaI RFLP in BDNF gene coding exon. Genomic subclone c41 and zBDNF cDNA clone 18.1 were digested with restriction enzymes and the fragments separated by agarose gel electrophoresis in the presence of ethidium bromide. The gel was photographed. Lanes 1-2: cDNA clone 18.1 cut with EcoRI (lane 1) and EcoRI/ApaI (lane 2). Lanes 3 and 4: genomic subclone c41 cut with HindIII (lane 3) and HindIII/ApaI (lane 4). Lane 5: Phage lambda HindIII digest.

The nucleotide sequence of c41 revealed an ApaI site in the prepro-region of the BDNF precursor that was not present in the previously cloned cDNA. The presence or absence of the ApaI site was confirmed by restriction analysis. c41 DNA, which contains the coding exon, and BDNF cDNA were cut with a single enzyme (HindIII and EcoRI, resp.) to release the cloned DNA. Aliquots of the digests were then cut with ApaI. The fragments were separated by agarose gel electrophoresis. FIG. 4 shows that the cDNA has no ApaI site and the genomic subclone c41 has a single one. As a result of the single nucleotide difference that abolishes the ApaI site the cDNA encodes a glutamic acid residue just downstream from the signal sequence of the BDNF precursor whereas the genomic clone encodes a Gln residue in the same position. The amino acid substitution alters the negative charge of the side-chain only two residues downstream from an Arg and therefore could be functionally significant. In any event, this RFLP will be useful in future mutagenesis screens when intragenic mutations must be distinguished from extragenic mutations by linkage analysis.

Alternate Promoters

The rat BDNF gene has four independently regulated promoters (see FIG. 1) (Bishop, J. F. et al. 1994, Hayes, V. Y. et al. 1997, Marmigere, F. et al. 1998, Metsis, M. et al. 1993, Nanda, S. and Mack, K. J. 1998, Shintani, A. et al. 1992, Timmusk, T. et al. 1994a, Timmusk, T. et al. 1993, Timmusk, T. et al. 1994b). The associated exons encode four 5' untranslated tracts which are alternately spliced to the coding exon to generate the mature BDNF mRNA transcripts, all of which encode the identical BDNF precursor. The alternate exons have been designated 1a-c and the coding exon has been exon 2 herein.

Nucleotide sequence comparison of the 5'UT of the previously cloned zebrafish BDNF cDNA with the rat BDNF gene revealed 67% identity with rat exon 1c (Hashimoto, M. and Heinrich, G. 1997). Moreover, in the zBDNF cDNA there was a sudden increase in similarity with the rat gene in the coding region at a point where the rat gene has an intron. This suggested that the zebrafish gene has an intron at the identical position. Sequence analysis of c41, which spans this region, confirmed the presence of an intron precisely where it occurs in the rat. Thus, the exon/intron structure of the BDNF gene is conserved.

In our in situ hybridization analyses of BDNF mRNA expression in 4 days old larvae, we had used probe1 and probe2 (Lum and Heinrich, 2001). The results showed a disparity between cells that hybridized to probe1 that is targeted exclusively to the coding exon (which is common to all BDNF transcripts) and probe2 that is targeted mainly to exon 1c. This disparity suggested that the zBDNF gene, like its rat counterpart, has multiple promoters. If their number and relative arrangement in the transcription unit were conserved we would expect an exon 1d about 500 bps downstream from exon 1c and a pair of exons 1a and b, also about 500 bps apart, located several kb upstream from exon 1c. Since a search through the nucleotide sequence bank at NCBI (National Center for Biological Information, Bethesda, Md.) for sequences similar to zebrafish exon 1c had identified rat exon 1c, we carried out similar searches using all sequences we had obtained from subclones MiBa, c4, and c25. However, none of the searches found any sequences that were related to the rat BDNF gene.

Promoter 1c Analysis

FIGS. 5A-B illustrate transcription factor recognition sites in the promoter region for promoter 1c. The nucleotide sequence was searched for similarities with known transcription factor binding sites using TESS. The nucleotide sequences with similarity were boldfaced and the abbreviated transcription factor name was written above them. When there was overlap between sequences arrows below the sequences were used and the transcription factor names were written either to the left or right of the arrows. The cloned BDNF mRNA sequences are boldfaced, italicized and underlined. The following nucleotide designations are used in TESS: (AC) M; (AG) R; (AT) W; (CG) S; (CT) Y; (GT) K; (AGC) V; (ACT) H; (AGT) H; (CGT) D; (AGTC) X/N. For details on each of the transcription factors, TESS may be consulted. FIGS. 8A-B illustrate a nucleic acid sequence of FIGS. 5A-B, without transcription factor recognition sites. FIGS. 9A-B illustrate another nucleic acid sequence for the promoter region of promoter 1c.

c25 contains the 5' end of the previously cloned cDNA and therefore the associated promoter and 5' flank. To more precisely delineate the promoter region and to facilitate future functional analyses the entire clone was sequenced. The nucleotide sequence was scanned by computer for potential transcription factor binding sites using TESS ('TESS: Transcription Element Search Software on the WWW', Jonathan Schug and G. Christian Overton, Technical Report CBIL-TR-1997-1001-v0.0, of the Computational Biology and Informatics Laboratory, School of Medicine, University of Pennsylvania, 1997. As expected, a number of potential binding sites were found. The most relevant sites are shown in FIGS. 5A-B. The mammalian BDNF gene is known to be regulated by calcium (Bishop, J. F. et al. 1997, Finkbeiner, S. 2000, Sano, K. et al. 1996, Shieh, P. B. and Ghosh, A. 1999, Shieh, P. B. et al. 1998) and CREB (Tao, X. et al. 1998). Several AP-1 and a potential CREB recognition sequence were found close to the promoter suggesting the zebrafish may be regulated by similar upstream regulators.

Expression of Promoter 1c in Embryos

Figure 6A:
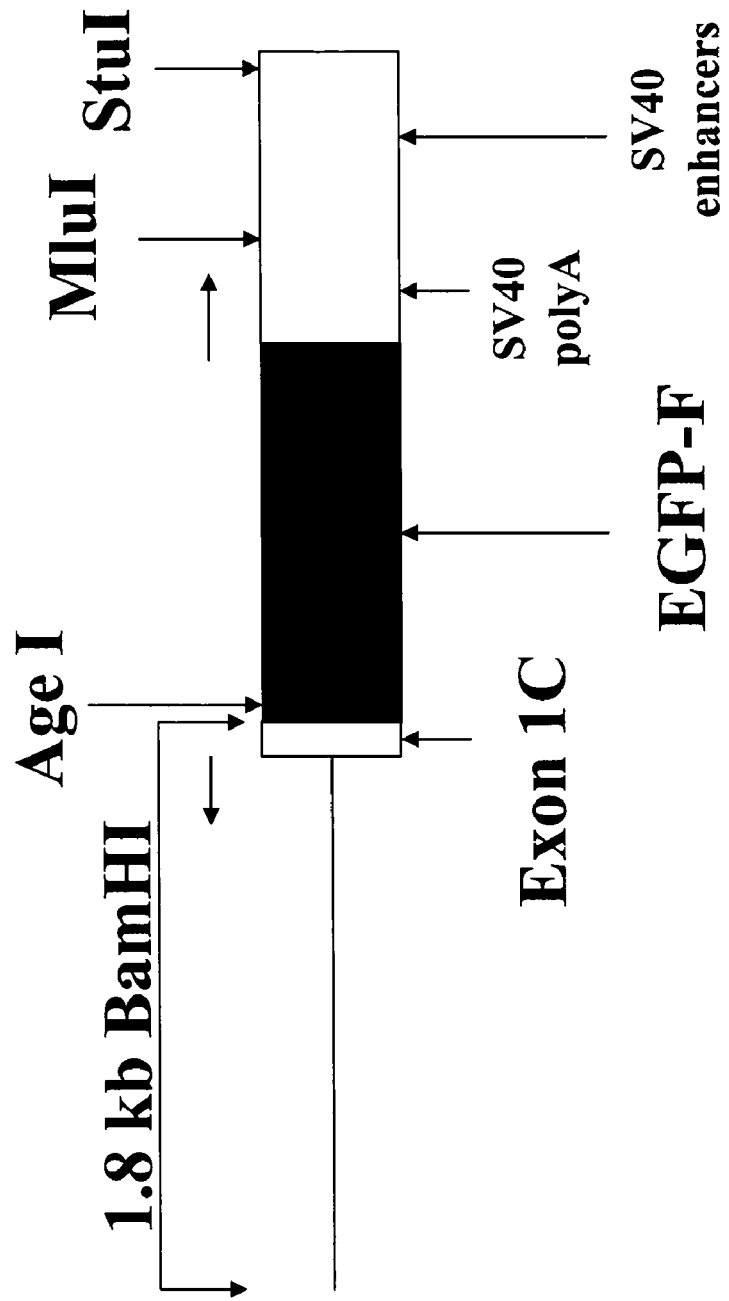
FIG. 6A illustrates an outline of BDNF/EGFP-F MiniExpress reporter construct of the invention.
Figure 6C:
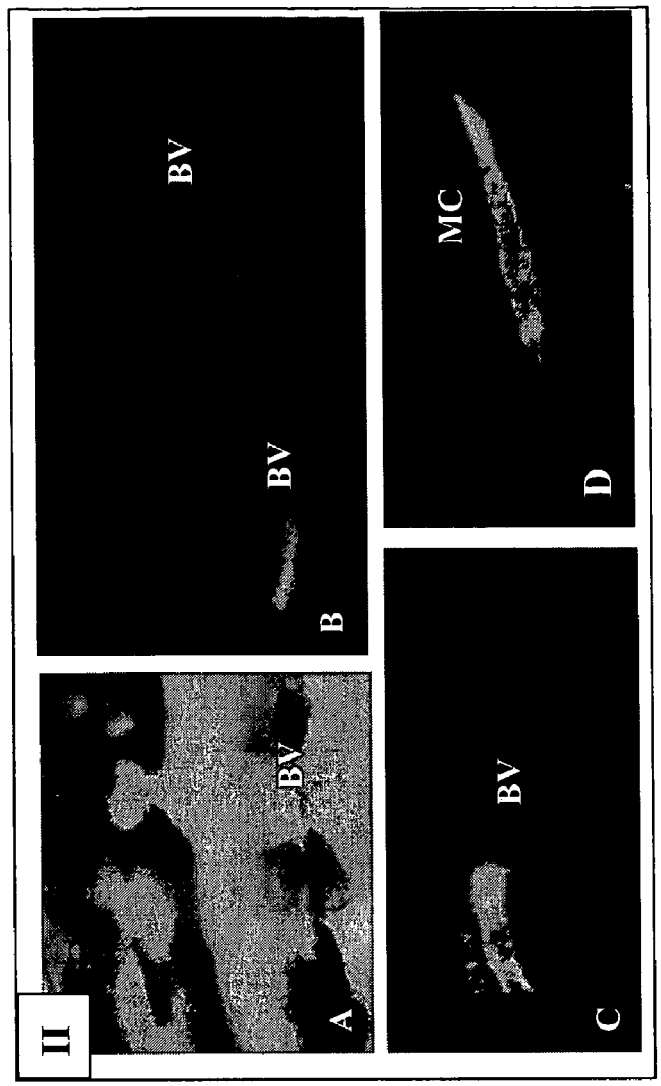
FIG. 6C (Panel II) (A-C) illustrates expression of BDNF/EGFP-F (MiniExpress) in blood vessels of 2-days old embryos.
Figure 6B:
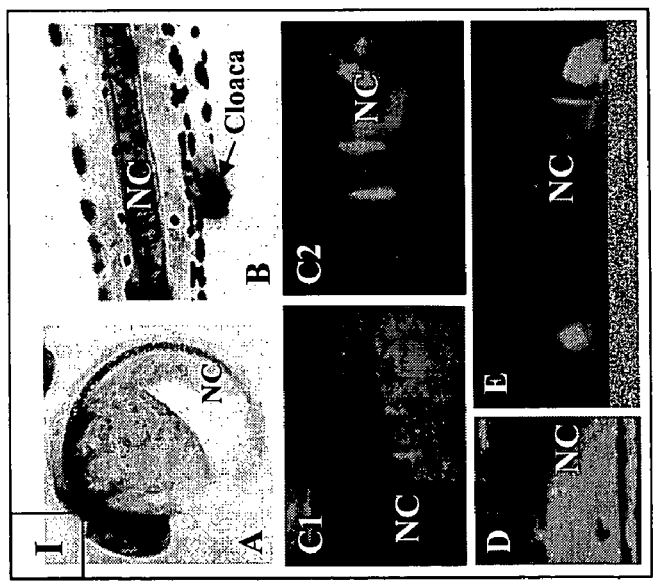
FIG. 6B (Panel I) (A-E) illustrates BDNF expression in notochord.

FIGS. 6A-C illustrate construction and expression of BDNF and BDNF/EGFP-F (MiniExpress) Fusion genes in zebrafish embryos and larvae.

FIG. 6A illustrates an outline of BDNF/EGFP-F MiniExpress reporter construct of the invention. The 5' end of exon 1c, consisting of 5' UT, is fused to the coding sequence of EGFP-F (black box). The 5' flank extends 1.7 kb upstream. The 3' end contains the SV40 polyadenylation upstream from the MluI site and SV40 enhancers between the MluI and StuI sites. Arrows indicate sequenced segments.

FIG. 6B. (Panel I) (A-E) illustrates BDNF expression in notochord. Panel IA illustrates BDNF mRNA visualized by in situ hybridization. The probe was a PCR-generated digoxigenin-labeled fragment of exon 2. Panel IB illustrates 4-days old larva. BDNF visualized by immunocytochemistry using MAb C-9 (Santa Cruz Biotech.). Panel IC1 illustrates 2-days old embryo injected with BDNF/EGFP-F (MiniExpress). Superimposed visible and fluorescent images. Panel IC2 illustrates fluorescent image of embryo shown in panel IC1. Panel ID illustrates 2-days old embryo injected with BDNF/EGFP-F (MiniExpress), fluorescent and visible images superimposed. Panel IE illustrates 2-days old embryo injected with BDNF/EGFP-F (MiniExpress), fluorescent image.

FIG. 6C (Panel II) (A-C) illustrates expression of BDNF/EGFP-F (MiniExpress) in blood vessels of 2-days old embryos. Panel IID illustrates expression of BDNF/EGFP-F (MiniExpress) in myocyte of trunk lateral myotome of 2-days old embryo. Panel III (A-C) illustrates expression of BDNF/EGFP-F (MiniExpress) in epithelial cells of 2-days old embryos. Panel IIIA1 is a lateral view, and panel IIIA2 a dorsal view of the same embryo. NC=notochord. BV=blood vessel.

To begin a functional analysis of promoter 1c, the insert of c25 was linked to the EGFP-F reporter. This reporter encodes an EGFP with a farnesylation signal at the 5' end. As a result, the EGFP becomes membrane anchored. In addition, the EGFP-F sequence is followed by SV40 polyA signals, mRNA 3' end and enhancers. We chose this reporter because it promised to be significantly more sensitive than EGFP. The resulting construct is shown in FIG. 6A and was called MiniExpress. Vector sequences and various SV40 sequences were removed prior to injection by digestion with StuI or MluI and agarose gel isolation of the desired fragments.

Embryos were dechorionated to facilitate injection of DNA into or close to the blastomeres at the 1-8 blastomere stages. However, even with injections at these early stages expression was highly mosaic, i.e. for any given cell type only a few cells expressed the reporter in any given injected embryo. For this reason, results are only reported for cell types that were seen to consistently express in >10 expressing embryos.

From the above, it can be observed that we have cloned a zebrafish genomic fragment that carries the BDNF coding exon and at least one functional promoter (FIG. 6A). Sequence analysis showed that the intron/exon organization of the zebrafish BDNF gene is identical to that of the mammalian BDNF gene. However, at this time we have identified with certainty only one promoter. Our in situ hybridization analyses with exon-specific probes showed that the exon 1c-specific probe hybridized to only a subset of BDNF mRNA positive cells (Lum and Heinrich, 2001). We also found several size classes of BDNF mRNA on Northern blot hybridization (Hashimoto, M. and Heinrich, G. 1997).

These findings suggest that the zebrafish BDNF gene has multiple promoters. Consistent with this possibility is the fact that promoter 1c expresses in only a subset of BDNF gene expressing cells. On the other hand, it is possible that the construct we examined lacks the cis regulatory elements that are required for expression in the additional cell types that express the endogenous BDNF gene. Again, this possibility are the results of preliminary experiments with constructs that extend farther upstream. Paradoxically, these constructs are expressed in fewer rather than more cell types than MiniExpress. The sequence analyses of MiBa and c4 are 90% complete. The remaining 10% could not be sequenced with the automated methods because they consist of small repetitive sequences and runs of adenosine and thymidine residues. They are thus unlikely to contain expressed exons. The sequenced regions of MiBa and c4 that contain potentially expressed exons together cover about 9 kb of genomic DNA. A BLAST search through the nucleotide sequence banks at NCBI for regions of similarity with the rat BDNF gene failed to find any. It is not clear whether any exons present in the sequenced regions are so dissimilar to their rat counterparts that they cannot be detected by the BLAST search engine, whether they are located farther away, or whether the zebrafish BDNF gene simply does not possess multiple promoters. The question of multiple promoters can be addressed experimentally by rapid amplification of cDNA ends (RACE).

The strong expression of BDNF mRNA in cartilage we had observed in our previous in situ hybridization and immunocytochemical analyses was originally somewhat unexpected (Lum and Heinrich, 2001). The expression of MiniExpress in the notochord that we observed in transiently transgenic embryos here are consistent with these data. The early and strong expression of the BDNF gene suggests an important function in skeleton development. The mammalian BDNF gene is also strongly expressed in cartilage and bone, but its function in these tissues is unknown.

The mammalian BDNF gene utilizes two polyadenylation signals that are almost 4 kb apart (Timmusk, T. et al. 1994, Timmusk, T. et al. 1993a). As a result most BDNF expressing tissues contain a large 4 kb transcript. Timmusk et al. (Timmusk, T. et al. 1994b) showed that this transcript is relatively rare in polysomes compared with the shorter more abundant transcripts of 1.6 kb and thus appears not to be as efficiently translated. We have not observed an equivalent large BDNF mRNA on our Northern blots despite overexposure of the autoradiograms (Hashimoto, M. and Heinrich, G. 1997). The zebrafish BDNF gene, thus appears to utilize only a single polyadenylation signal which we have cloned and sequenced. The 3' UT of the more abundant 1.6 kb mammalian BDNF mRNA and of zebrafish BDNF mRNA are relatively short, consisting of <500 nucleotides. Interestingly, our BLAST searches found two segments, a 23 and a 42 nucleotide segment, in the 3'UT that are identical in mammalian and zebrafish BDNF messages, suggesting important functions.

Indeed, Timmusk et al. (Timmusk, T. et al. 1995) reported that the cloned rat BDNF gene was only expressed cell-specifically in transgenic mice if the 3' flank was included. However, the fragment they used extended 4 kb downstream from the first polyadenylation signal to the second polyadenylation signal. Therefore, it is not clear whether it is the conserved sequences in the 3'UT of the shorter message that are responsible for the observed cell-specific expression or sequences located yet farther downstream, or both.

We used a reporter derivative of the enhanced green fluorescent protein, EGFP (Harvey, K. J. et al. 2001). A farnesylation signal at the COOH end of this modified EGFP anchors the reporter in the cell membrane. We found this reporter significantly more sensitive that the non-membrane bound EGFP. The membrane anchored EGFP outlines the entire cell membrane. As a result, the identification of the cell type expressing the reporter is greatly facilitated. It was readily possible to distinguish various types of neurons because cell bodies, dendrites and axons were all completely labeled and outlined. For example, primary motor neurons were immediately distinguishable from the primary sensory Rohon-Beard cells (Inoue, A. et al. 1994, Martin, S. C. et al. 1998).

Dynamic Versus Basal Promoter Activity Detection Systems

In assays of basal promoter activity, one is usually interested in knowing which cell types express a given promoter. For example, a promoter may be preferentially expressed in neurons versus skin cells. Basal activity of promoters that are preferentially expressed in one over another cell type results in cell-specific gene expression. This preferential basal promoter activity, i.e., cell-specific expression, can be detected by injecting zebrafish embryos with the promoter linked to a reporter. The injected embryos are then examined for cells that express the reporter. The patterns of cells that express the reporter provide an indication of the cell-specificity of the promoter. An example of a cell-specific promoter is the BDNF gene promoter 1c. It is preferentially expressed in neurons.

In contrast to cell-specific promoters, universal promoters are expressed in all cell types. Universal promoters drive the so-called housekeeping genes, such as glyceraldehyde dehydrogenase (GAPDH). GAPDH is expressed in all cell types. If the GAPDH promoter is linked to a reporter and then injected into zebrafish embryos, one would expect all cell types to express the reporter.

In assays of dynamic promoter activity, one is more interested in the changes in promoter activity in response to particular stimuli than cell-specificity of promoter activity, as described above. For example, we would be more interested in identifying a drug that stimulates BDNF promoter 1c activity, than in understanding why and how the promoter is specifically expressed in neurons. In this regard, it is conceivable that a BDNF promoter 1c construct that is expressed in a number of cell types in addition to neurons will allow us just as readily to identify stimuli that enhance or suppress promoter activity as one that expresses exclusively in neurons. Thus, the search for stimuli that dynamically influence promoter activity does not require cell-specific expression.

The distinction between basal and dynamic promoter activity is important because our goal is identification of stimuli/drugs that dynamically alter promoter activity.

Red Fluorescent Protein as a Reporter

Red Fluorescent Protein (RFP) was cloned from the sea anemone *Discosoma striata*, and is available from Clontech, now B.D. Biosciences, San Jose, Calif., www.bdbiosciences.com. On the other hand, green Fluorescent Protein (GFP) was isolated and cloned from the jellyfish *Aequorea Victoria*. RFP has been genetically engineered to become less toxic to mammalian cells, primarily by reducing its potential to form large intracellular aggregates. Both RFP and GFP must undergo cellular maturation to become fluorecent. A variant of RFP, DsRed1-E5, initially fluoresces green. Upon maturation, it begins to fluoresce red. This variant can be used to detect changes in promoter activity when the promoter has significant base line activity.

For example, in a transgenic zebrafish that expresses BDNFprom1c/RFP, the reporter pool derived from basal activity will contain mostly the red fluorescing mature form of RFP. Stimulation of promoter activity with a substance being screened for promoter 1c-stimulating activity will result in addition of newly synthesized immature green fluorecent reporter. Using green and red filters one can distinguish the newly synthesized green fluorescent form of RFP from the mature red fluorescent form in the pre-exiting cellular pool. Therefore increased promoter activity can be detected even in the presence of substantial pools of mature RFP resulting from basal promoter 1c activity. The distinction between newly synthesized and pre-existing molecules will not be possible with a GFP reporter because both fluoresce green. Thus, the DsRed1-E5 is ideal for transgenic lines that express the reporter under basal conditions and are being used for screening of drugs that stimulate promoter activity above and beyond that basal activity. This situation pertains to all transgenic lines that have visible expression under basal conditions.

Transgenic lines that have no basal expression can also be constructed. This can be done by identifying transgenic fish that carry the transgene in the genome rather than reporter expression. To identify such transgenics, one would analzye the genomic DNA of individual fish using PCR or Southern bloth hybridization.

DsRed2 is another variant of RFP that was obtained through genetic engineering. DsRed2 matures quickly and has a short half-life. The short half-life (T½) results in a small cellular pool size due to basal promoter activity. Small pool sizes are desirable when one wishes to detect increases in promoter activity. With a small pool size any addition of newly synthesized molecules due to stimulation of promoter activity results in a large fractional increase relative to the pre-existing pool. DsRed2 is therefore particularly well suited for screening of drugs for BDNF promoter 1c stimulating activity. It is possible that transgenic BDNFprom1c/DsRed2 transgenic lines may not exhibit basal fluorescence (see above). Such lines will be detected by PCR of genomic DNA, a method that does not rely on detectable basal expression of the reporter.

Additional constructs, derived from promoters of the BDNF gene other than the one present in MiniExpress may also be linked to RFP reporters.

The construct of the invention can be used to rapidly screen a number of substances for their ability to influence the production of BDNF in a living organism. The preferable living organism is a zebrafish embryo or fry. The zebrafish is altered genetically so it carries the new gene that it passes on to all its progeny. The new gene or construct is assembled by standard molecular biology methods. It has two main components: a portion of the zebrafish BDNF gene that controls transcription, i.e., the promoter, and another gene that encodes a protein which fluoresces under UV light. The single new gene derived from the two components is called a fusion gene or construct.

When the fusion gene is injected into a zebrafish embryo, the BDNF promoter portion causes the production of the fluorescent protein in various cell types. The amount of protein, and hence fluorescence, is dependent on the activity of BDNF promoter. One can then expose embryos or larvae that carry this fusion gene to any desired chemical or biological substance to measure the effect of the substance on the production of the FP. The observed fluorescence is a measure of activity of the zebrafish's own BDNF gene and, hence a measure of BDNF production in various organs of the zebrafish. Bu utilizing this kind of screen, one can discover substances that have the capability to modulate BDNF production.

FIGS. 7A-E illustrate a construct made in accordance with the present invention, wherein nucleotides 1 to 263, 2154 to 2172, and 4159 to 6428 represent vectors; nucleotides 2173 to 2967 represent a reporter; nucleotides 264 to 2035 represent 5' flank of zebrafish BDNF gene; nucleotides 2036 to 2063 represent a promoter of zebrafish BDNF gene; nucleotides 2064 to 2153 represent exon 1c (5' UT) of zebrafish BDNF gene; nucleotides 3001-4159 represent SV40 sequences. The fragment injected into zebrafish embryos for expression is represented by nucleotides 236 to 3223.

FIGS. 10A-F illustrate a second embodiment of a construct made in accordance with the present invention, wherein nucleotides 1 to 20, 2100 to 2119, and 5100 to 7508 represent vectors; nucleotides 2120 to 2815 represent a reporter; nucleotides 21 to 1776 represent 5' flank of zebrafish BDNF gene; nucleotides 1777 to 1804 represent a promoter of zebrafish BDNF gene; nucleotides 1805 to 2099 represent exon 1c (5' UT) of zebrafish BDNF gene; nucleotides 2816-2820 and 2821-5099 represent linker and 3' flank sequences, respectively. The fragment injected into zebrafish embryos for expression is represented by nucleotides 15 to 5104. The reporter, or expression vector, in the sequence illustrated in FIGS. 10A-F and SEQ ID NO.: 4, was derived from vector pIRES2-DsRed2, commercially available from Clontech, noted above.

FIGS. 11A-F illustrate a third embodiment of a construct made in accordance with the present invention, wherein nucleotides 1 to 20, 2100 to 2122, and 5087 to 7495 represent vectors; nucleotides 2123 to 2800 represent a reporter; nucleotides 21 to 1776 represent 5' flank of zebrafish BDNF gene; nucleotides 1777 to 1804 represent a promoter of zebrafish BDNF gene; nucleotides 1805 to 2099 represent exon 1c (5' UT) of zebrafish BDNF gene; nucleotides 2801-2807 and 2808-5086 represent linker and 3' flank sequences, respectively. The fragment injected into zebrafish embryos for expression is represented by nucleotides 15 to 5091. The reporter, or expression vector, in the sequence illustrated in FIGS. 11A-F and SEQ ID NO.: 5, was derived from vector pDsRed1-E5 (also known as PTIMER), commercially available from Clontech, noted above.

Operation

The main tool are transgenic fish lines that stably express BDNF gene promoters linked to a fluorescent protein reporter (BDNF/FP fusion genes) whose cellular levels can be measured using fluorescent imaging equipment.

In order to create transgenic zebrafish lines, the BDNF/FP fusion genes are constructed from cloned zebrafish BDNF gene promoters and various fluorescent protein (FP) (green, red, yellow or blue) reporters by standard methods. (The FPs are obtained from commercial sources, such as Clontech, Inc.) The fusion genes are sequenced to confirm their structure, and are then injected into zebrafish embryos at the 1-8 cell stage of embryonic development. Transgenic lines are derived from the founder embryos by standard breeding and analysis methods.

Embryos from transgenic lines are exposed to a test substance and the level of reporter FP is compared to controls using fluorescent imaging equipment and computer image analysis. The test substances are either dissolved in ambient water or injected into the yolk or cell mass. At larval stages, the test substances are dissolved in ambient water or injected into various body sites, such as organs, the stomach, or the blood stream. We observed expression in notochord, muscle, epithelial and endothelial cells of the 1 day old embryo in consonance with the endogenous gene.

The construct of the invention and additional constructs, in progress, will allow us to establish transgenic zebrafish lines that will permit direct and live visual observation of BDNF gene expression. Such lines will be useful for the identification of genes that regulate BDNF gene expression using mutagenesis. With a short-lived reporter, it will also be possible to observe "real-time" dynamic changes of BDNF gene transcription in response to various physiological and experimental stimuli in the nervous system of the developing zebrafish embryo.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

The following references, to the extent that they provide exemplary procedural or other details supplementary to those set forth herein, are specifically incorporated herein by reference.

Alderson, R. F., Alternan, A. L., Barde, Y. A. and Lindsay, R. M., (1990) Brain-derived neurotrophic factor increases survival and differentiated functions of rat septal cholinergic neurons in culture. Neuron, 5: 297-306.

Amgen-Regeneron Partners. Intrathecal and Subcutaneous BDNF not shown effective in ALS. MDA Research. (Jan. 11, 2002.)

Balbes, L. M., M. Cline, and D. D. Beusen. (2001) From target to drug in the virtual discovery lab. Drug Discovery and Development. April 2001.

Biffo, S., Dechant, G., Okazawa, H. and Barde, Y. A., (1994) Molecular control of neuronal survival in the chick embryo. EXS, 71:39-48.

Binder, D. K., S. D. Croll, C. M. Gall, and H. E. Scharfman. (2001) BDNF and epilepsy: too much of a good thing? Trends in Neurosciences, 24(1):47-53.

Bishop, J. F., Joshi, G., Mueller, G. P. and Mouradian, M. M., (1997) Localization of putative calcium-responsive regions in the rat BDNF gene. Brain Res Mol Brain Res 50 IP, 1-2:154-164.

Bishop, J. F., Mueller, G. P. and Mouradian, M. M., (1994) Alternate 5' exons in the rat brain-derived neurotrophic factor gene: differential patterns of expression across brain regions. Brain Res Mol Brain Res 26 IP, 1-2:225-232.

Cockett, M., N. Dracopoli, and E. Sigal. (2000) Applied genomics: integration of the technology within pharmaceutical research and development. Current Opinion in Biotechnology, 11:602-609.

Cohen, N., Abramov, S., Dror, Y., and Freeman, A. (2001) In vitro enzyme evolution: the screening challenge of isolating the one in a million. TRENDS in Biotechnology, 19(12):507-510.

Davies, A. M., Thoenen, H. and Barde, Y. A., (1986) The response of chick sensory neurons to brain-derived neurotrophic factor. J Neurosci, 6:1897-904.

Department of Neurology, Baylor College of Medicine. Brain-Derived Neurotrophic Factor (BDNF). (Jan. 11, 2002.)

Dodd, A., P. M. Curtis, L. C Williams, and D. R Love. (2000) Zebrafish: bridging the gap between development and disease. Human Molecular Genetics. 9(16): Review, 2443-2449.

Finkbeiner, 5., (2000) Calcium regulation of the brain-derived neurotrophic factor gene. Cell Mol Life Sci 57 IP, 3:394-401.

Fox, S. J., M. A. Yund, and S. Farr-Jones. (2000) Assay innovations vital to improving HTS. Drug Discovery and Development. March 2000.

Frade, J. M., Bovolenta, P., Martinez-Morales, J. R., Arribas, A., Barbas, J. A. and Rodriguez-Tebar, A., (1997) Control of early cell death by BDNF in the chick retina. Development, 124:3313-20.

Gotz, R., Koster, R., Winkler, C., Raulf, F., Lottspeich, F., Schartl, M. and Thoenen, H., (1994) Neurotrophin-6 is a new member of the nerve growth factor family. Nature, 372:266-9.

Guillemot, F., Auffray, C. and Devignes, M. D., (1999) Detailed transcript map of a 810-kb region at 11p14 involving identification of 10 novel human 3' exons. Eur J Hum Genet 7 IP, 4:487-495.

Harvey, K. J., Lukovic, D. and Ucker, D. S., (2001) Membrane-targeted green fluorescent protein reliably and uniquely marks cells through apoptotic death. Cytometry, 43:273-8.

Hashimoto, M. and Heinrich, G., (1997) Brain-derived neurotrophic factor gene expression in the developing zebrafish. Int J Dev Neurosci, 15:983-97.

Haupts, U., M. Rudiger. and A. J. Pope. (2000) Macroscopic versus microscopic fluorescence techniques in (ultra)-high throughput screening. Drug Discovery Today: HTS Supplement, 1 (1). June 2000.

Hayes, V. Y., Towner, M. D. and Isackson, P. J., (1997) Organization, sequence and functional analysis of a mouse BDNF promoter. Brain Res Mol Brain Res 45 IP, 2:189-198.

Herzog, K. H., Bailey, K. and Barde, Y. A., (1994) Expression of the BDNF gene in the developing visual system of the chick. Development, 120:1643-9.

Hyman, C., Hofer, M., Barde, Y. A., Juhasz, M., Yancopoulos, G. D., Squinto, S. P. and Lindsay, R. M., (1991) BDNF is a neurotrophic factor for dopaminergic neurons of the substantia nigra. Nature, 350:230-2.

Huynh, G. and G. Heinrich. (2001) Brain-derived neurotrophic factor gene organization and transcription in the zebrafish embryo. International Journal of Developmental Neuroscience, 19:663-673.

Inoue, A., Takahashi, M., Hatta, K., Hotta, Y. and Okamoto, H., (1994) Developmental regulation of islet-1 mRNA expression during neuronal differentiation in embryonic zebrafish. Dev Dyn, 199:1-11.

Ip, N. Y., Ibanez, G. E., Nye, S. H., McClain, J., Jones, P. F., Gies, D. R., Belluscio, L., Le Beau, M. M., Espinosa R, 3. r., Squinto, S. P. and et, a.l., (1992) Mammalian neurotrophin-4: structure, chromosomal localization, tissue distribution, and receptor specificity. Proc Natl Acad Sci USA, 89:3060-4.

Johnson, J. E., Barde, Y. A., Schwab, M. and Thoenen, H., (1986) Brain-derived neurotrophic factor supports the survival of cultured rat retinal ganglion cells. J Neurosci, 6:3031-8.

Levi-Montalcini, R., Dal Toso, R., della Valle, F., Skaper, S. D. and Leon, A., (1995) Update of the NGF saga. J Neurol Sci, 130:119-27.

Levi-Montalcini, R., (1998) The saga of the nerve growth factor. Neuroreport, 9:R71-83.

Lum, T., G. Huynh, and G. Heinrich. (2001) Brain-derived neurotrophic factor and TrkB tyrosine kinase receptor gene expression in zebrafish embryo and larva. International Journal of Developmental Neuroscience, 19:569-587.

Maisonpierre, P. C., Belluscio, L., Squinto, S., Ip, N.Y., Furth, M. E., Lindsay, R. M. and Yancopoulos, G. D., (1990) Neurotrophin-3: a neurotrophic factor related to NGF and BDNF. Science, 247:1446-51.

Maisonpierre, P. C., Le Beau, M. M., Espinosa R, 3.r., Ip, N.Y., Belluscio, L., de la, M.o.S., Squinto, S., Furth, M. E. and Yancopoulos, G. D., (1991) Human and rat brain-derived neurotrophic factor and neurotrophin-3: gene structures, distributions, and chromosomal localizations. Genomics, 10:558-68.

Marmigere, F., Rage, F., Tapia-Arancibia, L. and Arancibia, 5., (1998) Expression of mRNAs encoding BDNF and its receptor in adult rat hypothalamus. Neuroreport 9 IP, 6:1159-1163.

Martin, S. C., Sandell, J. H. and Heinrich, G., (1998) Zebrafish TrkC1 and TrkC2 receptors define two different cell populations in the nervous system during the period of axonogenesis. Dev Biol, 195:114-30.

Metsis, M., Timmusk, T., Arenas, E. and Persson, H., (1993) Differential usage of multiple brain-derived neurotrophic factor promoters in the rat brain following neuronal activation. Proc Natl Acad Sci USA 90 IP, 19:8802-8806.

Nanda, S. and Mack, K. J., (1998) Multiple promoters direct stimulus and temporal specific expression of brain-derived neurotrophic factor in the somatosensory cortex. Brain Res Mol Brain Res 62 IP, 2:216-219.

Nature America Inc. (2000) Targeting zebrafish. nature genetics, 26(2):129-130.

Nasevicius, A., and Ekker, S. (2000) Effective targeted gene 'knockdown' in zebrafish. nature genetics, 26:216-220.

Nilsson, A. S., Fainzilber, M., Falck, P. and Ibanez, C. F., (1998) Neurotrophin-7: a novel member of the neurotrophin family from the zebrafish. FEBS Lett, 424:285-90.

Pickering, L. (2001) Developing Drugs to Counter Disease. Medical Chemistry, 44-47.

Reiss, T. (2001) Drug discovery of the future: the implications of the human genome project. Trends in Biotechnology, 19(12):496-499.

Rodriguez-Tebar, A. and Barde, Y. A., (1988) Binding characteristics of brain-derived neurotrophic factor to its receptors on neurons from the chick embryo. J Neurosci, 8:3337-42.

Rodriguez-Tebar, A., Jeffrey, P. L., Thoenen, H. and Barde, Y. A., (1989) The survival of chick retinal ganglion cells in response to brain-derived neurotrophic factor depends on their embryonic age. Dev Biol, 136:296-303.

Russo-Neustadt A, T. Ha, R. Ramirez, and J. P. Kesslak. Physical activityantidepressant treatment combination: impact on brain-derived neurotrophic factor and behavior in an animal model. Behaviour Brain Research, 120(1):87-95. BLTC Research. (Jan. 11, 2002.)

Sano, K., Nanba, H., Tabuchi, A., Tsuchiya, T. and Tsuda, M., (1996) BDNF gene can Be activated by Ca2+ signals without involvement of de novo AP-1 synthesis. Biochem Biophys Res Commun 229 IP, 3:788-793.

Sendtner, M., Holtmann, B., Kolbeck, R., Thoenen, H. and Barde, Y. A., (1992) Brain-derived neurotrophic factor prevents the death of motoneurons in newborn rats after nerve section. Nature, 360:757-9.

Shieh, P. B. and Ghosh, A., (1999) Molecular mechanisms underlying activity-dependent regulation of BDNF expression. J Neurobiol 41 IP, 1:127-134.

Shieh, P. B., Hu, S. C., Bobb, K., Timmusk, T. and Ghosh, A., (1998) Identification of a signaling pathway involved in calcium regulation of BDNF expression. Neuron, 20:727-40.

Shintani, A., Ono, Y., Kaisho, Y. and Igarashi, K., (1992) Characterization of the 5'-flanking region of the human brain-derived neurotrophic factor gene. Biochem Biophys Res Commun 182 IP, 1:325-332.

Stainier, D. (2001) Zebrafish Genetics and Vertebrate Heart Formation. Nature Reviews, 2:39-48.

Tao, X., Finkbeiner, S., Arnold, D. B., Shaywitz, A. J. and Greenberg, M. E., (1998) Ca2+ influx regulates BDNF transcription by a CREB family transcription factor-dependent mechanism. Neuron 20 IP, 4:709-726.

Timmusk, T., Belluardo, N., Persson, H. and Metsis, M., (1994a) Developmental regulation of brain-derived neurotrophic factor messenger RNAs transcribed from different promoters in the rat brain. Neuroscience 60 IP, 2:287-291.

Timmusk, T., Lendahl, U., Funakoshi, H., Arenas, E., Persson, H. and Metsis, M., (1995) Identification of brain-derived neurotrophic factor promoter regions mediating tissue-specific, axotomy-, and neuronal activity-induced expression in transgenic mice. J Cell Biol, 128:185-99.

Timmusk, T., Palm, K., Metsis, M., Reintam, T., Paalme, V., Saarma, M. and Persson, H., (1993) Multiple promoters direct tissue-specific expression of the rat BDNF gene. Neuron 10 IP, 3:475-489.

Timmusk, T., Persson, H. and Metsis, M., (1994b) Analysis of transcriptional initiation and translatability of brain-derived neurotrophic factor mRNAs in the rat brain. Neurosci Lett 177 IP, 1-2:27-31.

Vente, A., Korn, B., Zehetner, G., Poustka, A. and Lehrach, H., (1999) Distribution and early development of microarray technology in Europe. Nat Genet, 22:22.

Wixon, J. *Danio rerio*, the zebrafish. Yeast, 17:225-231. (Sep. 19, 2001.)

Zehetner, G. and Lehrach, H., (1994) The Reference Library System—sharing biological material and experimental data. Nature, 367:489.

What is claimed is:

1. A transgenic zebrafish embryo or larva, whose genome comprises: a promoter comprising nucleotides 1777 to 1804 as set forth in SEQ ID NO: 4 operably linked to a reporter gene encoding red fluorescence protein (RFP).

2. A method of screening a substance for regulation of brain-derived neurotrophic factor (BDNF) production, comprising the steps of: a) providing a transgenic zebrafish embryo whose genome comprises a fusion gene, wherein said fusion gene comprises a zebrafish genomic fragment comprising a BDNF promoter and a BDNF exon operably linked to a reporter gene encoding red fluorescence protein (RFP) and b) exposing said transgenic zebrafish embryo to a test substance; and c) detecting the level of RFP protein produced by the transgenic zebrafish embryo, thereby determining regulation of BDNF production by the test substance.

3. The method of claim 2, wherein the reporter gene encoding red fluorescence protein (RFP) comprises nucleotides 2120 to 2815 as set forth in SEQ ID NO: 4.

4. The method of claim 2, wherein the fusion gene comprises nucleotides 15 to 5104 as set forth in SEQ ID NO: 4.

5. The method of claim 2, wherein the fusion gene comprises nucleotides 15 to 5091 as set forth in SEQ ID NO: 5.

* * * * *

UNITED STATES PATENT AND TRADEMARK OFFICE
CERTIFICATE OF CORRECTION

| | |
|---|---|
| PATENT NO. | : 7,615,676 B2 |
| APPLICATION NO. | : 10/742828 |
| DATED | : November 10, 2009 |
| INVENTOR(S) | : Heinrich et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this

Nineteenth Day of October, 2010

David J. Kappos
*Director of the United States Patent and Trademark Office*